US008878002B2

(12) United States Patent
Siddiqi et al.

(10) Patent No.: US 8,878,002 B2
(45) Date of Patent: Nov. 4, 2014

(54) NUCLEIC ACIDS AND METHODS FOR PRODUCING SEEDS WITH A FULL DIPLOID COMPLEMENT OF THE MATERNAL GENOME IN THE EMBRYO

(75) Inventors: Imran Siddiqi, Andhra Pradesh (IN); Maruthachalam Ravi, Andhra Pradesh (IN); Mohan Prem Anand Marimuthu, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 1247 days.

(21) Appl. No.: 11/598,021

(22) Filed: Nov. 13, 2006

(65) Prior Publication Data

US 2007/0136895 A1 Jun. 14, 2007

(30) Foreign Application Priority Data

Dec. 9, 2005 (IN) .......................... 3337/DEL/2005

(51) Int. Cl.
| A01H 1/00 | (2006.01) |
| C12N 15/82 | (2006.01) |
| A01H 5/00 | (2006.01) |
| A01H 5/10 | (2006.01) |
| C07K 14/415 | (2006.01) |
| C12N 15/12 | (2006.01) |
| C12N 15/29 | (2006.01) |
| C12N 15/62 | (2006.01) |
| A01H 1/06 | (2006.01) |

(52) U.S. Cl.
CPC .......... *C12N 15/8287* (2013.01); *C07K 14/415* (2013.01); *C12N 15/829* (2013.01)
USPC ........... 800/271; 800/270; 800/278; 800/288; 800/290; 800/306; 435/69.7; 435/69.8; 536/23.4; 536/23.5; 536/23.6

(58) Field of Classification Search
None
See application file for complete search history.

(56) References Cited

U.S. PATENT DOCUMENTS

| 5,710,367 | A | 1/1998 | Kindiger et al. |
| 5,767,374 | A | 6/1998 | De Greef et al. |
| 5,811,636 | A | 9/1998 | Hanna et al. |
| 5,840,567 | A | 11/1998 | Durzan |
| 5,850,014 | A | 12/1998 | Albertsen et al. |
| 6,028,185 | A | 2/2000 | Ozias-Akins et al. |
| 6,051,752 | A | 4/2000 | Sauton et al. |
| 6,147,282 | A * | 11/2000 | Goff et al. .................... 800/303 |
| 6,229,064 | B1 | 5/2001 | Fischer et al. |
| 6,235,975 | B1 | 5/2001 | Harada et al. |
| 6,239,327 | B1 | 5/2001 | Grossniklaus et al. |
| 6,492,577 | B1 | 12/2002 | Harada et al. |
| 6,750,376 | B1 | 6/2004 | Carman |
| 6,825,397 | B1 | 11/2004 | Lowe et al. |
| 6,906,244 | B2 | 6/2005 | Fischer et al. |

FOREIGN PATENT DOCUMENTS

| WO | WO-97/10704 | 3/1997 |
| WO | WO-98/33374 | 8/1998 |
| WO | WO-98/36090 | 8/1998 |
| WO | WO-99/35258 | 7/1999 |
| WO | WO-99/53083 | 10/1999 |
| WO | WO-00/07434 | 2/2000 |
| WO | WO-00/24914 | 5/2000 |
| WO | WO-01/21785 A2 | 3/2001 |
| WO | WO-01/31017 A2 | 5/2001 |
| WO | WO-01/32001 A1 | 5/2001 |
| WO | WO-02/083912 A2 | 10/2002 |
| WO | WO-03/000923 A2 | 1/2003 |
| WO | WO-03/037072 A2 | 8/2003 |
| WO | WO-2005/039275 A2 | 5/2005 |
| WO | WO-2005/063990 A2 | 7/2005 |

OTHER PUBLICATIONS

Agashe et al. Development 129(16): 3935-3943 (Aug. 2002).*
Agashe et al. Accession No. AF466153 (Jul. 2002).*
Schena et al. Proc. Natl. Acad. Sci. USA 88(23): 10421-10425 (Dec. 1991).*
Rhoades et al. Genetics 54: 505-522 (Aug. 1966).*
Tavoletti et al. Proc. Natl. Acad. Sci. USA 93: 10918-10922 (Oct. 1996).*
Vorea et al. Journal of Heredity 88: 423-426 (1997).*
Crespel et al. Theoretical and Applied Genetics 104: 451-456 (2002).*
Moamayor et al. Sexual Plant Reproduction 12: 209-218 (2000).*
Ravi et al. Nature 451: 1121-1125 (Feb. 2008).*
Parcy et al. Nature 395: 561-566 (1998).*
Maizel et al. Plant Journal 38: 164-171 (2004).*
Ravi et al. Alignment of SEQ ID No. 1 of U.S. Appl. No. 11/598,021, filed Nov. 2006.*
Ravi et al. Alignment of SEQ ID No. 4 of U.S. Appl. No. 11/598,021, filed Nov. 2006.*
Pawlowski et al. (2009) PNAS Early Edition; www.pnas.org/cgi/doi/10.1073/pnas.0810115106, pp. 1-6 and Fig. S4.*
Asker, S., "Progress in Apomixis Research", Hereditas, vol. 91, pp. 231-240, 1979.
Betzner, A.S. et al., "Transfer RNA-mediated suppression of amber stop codons in transgenic *Arabidopsis thaliana*", The Plant Journal, vol. 11, No. 3, pp. 587-595, 1997.
Bohner, S. et al., "Transcriptional activator TGV mediates dexamethasone-inducible and tetracycline-inactivatable gene expression", The Plant Journal, vol. 19, No. 1, pp. 87-95, 1999.
Bohuon, E.J.R. et al, "The Association of Flowering Time Quantitative Trait Loci and Duplicated Regions and Candidate Loci in *Brassica oleracea*", Genetics, vol. 150, pp. 393-401, 1998.

(Continued)

*Primary Examiner* — David T Fox
(74) *Attorney, Agent, or Firm* — Roberts Mlotkowski Safran & Cole, P.C.

(57) ABSTRACT

The present invention relates to DYAD genes, mutants thereof, and use of them for making plants that retain heterozygosity of the female parent plant. The invention also encompasses plants, plant tissues, and seeds of plants that have a dyad phenotype and so retain heterozygosity of the female parent, either constitutively or conditionally. The invention is useful for propagating desired hybrid phenotypes in a manner of an apomictic plant and for increasing the ploidy of a plant genotype, which may result in plants having increased biomass.

13 Claims, 13 Drawing Sheets

(56) References Cited

OTHER PUBLICATIONS

Causse, M.A. et al., "Saturated Molecular Map of the Rice Genome Based on an Interspecific Backcross Population", Genetics, vol. 138, pp. 1251-1274, 1994.
Chan, P. et al., "Triplex DNA: fundamentals, advances, and potential applications for gene therapy", Journal of Molecular Medicine, vol. 75, pp. 267-282, 1997.
Choisne, N. et al., "Transactivation of a target gene using a suppressor tRNA in transgenic tobacco plants", The Plant Journal, vol. 11, No. 3, pp. 597-604, 1997.
Coe, E. e al., "Access to the Maize Genome: An Integrated Physical and Genetic Map", Plant Physiology, vol. 128, pp. 9-12, 2002.
Cole-Strauss, A. et al., "Correction of the Mutation Responsible for Sickle Cell Anemia by an RNA-DNA Oligonucleotide", Science, vol. 273, pp. 1386-1389, 1996.
Conceicao, A.d.S. et al., "A cotyledon regulatory region is responsible for the different spatial expression patterns of *Arabidopsis* 2S albumin genes", The Plant Journal, vol. 5, No. 4, pp. 493-505, 1994.
Couteau, F. et al., "Random Chromosome Segregation without Meiotic Arrest in Both Male and Female Meiocytes of a *dmc1* Mutant of *Arabidopsis*", The Plant Cell, vol. 11, pp. 1623-1634, 1999.
De Koeyer, D.L. et al., "A molecular linkage amp with associated QTLs from a huilness x covered spring oat population", Theor. Appl. Genet., vol. 108, pp. 1285-1298, 2004.
Deveaux, Y. et al., "The ethanol switch: a tool for tissue-specific gene induction during plant development", The Plant Journal, vol. 36, pp. 918-930, 2003.
Doganlar, S. et al., "A Comparative Genetic Linkage Map of Eggplant (*Solanum melongena*) and Its Implications for Genome Evolution in the Solanaceae", Genetics, vol. 161, pp. 1697-1711, 2002.
Esposito, R. et al., "Genetic Recombination and Commitment to Meiosis in *Saccharomyces*" Proc. Nat. Acad. Sci. USA. vol. 71, No. 8, pp. 3172-3176, 1974.
Feng, D. et al., "Progressive Sequence Alignment as a Prerequisite to Correct Phylogenetic Trees", Journal of Molecular Evolution, vol. 25, pp. 351-360, 1987.
Ferreira, A.R. et al., "Soybean Genetic Map of RAPD Markers Assigned to an Existing Scaffold RFLP Map", J. Heredity, vol. 91, pp. 392-396, 2000.
Flavell, R.B., "Inactivation of gene expression in plants as a consequence of specific sequence duplication", Proc. Natl. Acad. Sci. USA, vol. 91, pp. 3490-3496, 1994.
Fraley, R.T. et al., "Expression of bacterial genes in plants", Proc. Natl. Acad. Sci. USA, vol. 80, pp. 4803-4807, 1983.
Fromm, M. et al., "Expression of genes transferred into monocot and dicot plant cells by electroporation", Proc. Natl. Acad. Sci. USA, vol. 82, pp. 5824-5828, 1985.
Giovannangeli, C. et al., "Specific Inhibition of in Vitro Transcription Elongation by Triplex-Forming Oligonucleotide-Intercalator Conjugates Targeted to HIV Proviral DNA", Biochemistry, vol. 35, pp. 10539-10548, 1996.
Grelon, M. et al., "*AtSPO11-1* is necessary for efficient meiotic recombination in plants", The EMBO Journal, vol. 20, No. 3, pp. 589-600, 2001.
Grewal, S.I.S. et al., "A Recombinationally Repressed Region Between mat2 and mat3 Loci Shares Homology to Centromeric Repeats and Regulates Directionality of Mating-Type Switching in Fission Yeast", Genetics, vol. 146, pp. 1221-1238, 1997.
Harushima, Y. et al., "A High-Density Rice Genetic Linkage Map with 2275 Markers Using a Single $F_2$ Population", Genetics, vol. 148, pp. 479-494, 1998.
Haseloff, J. et al., "Simple RNA enzymes with new and highly specific endoribonuclease activities", Nature, vol. 334, pp. 585-591, 1988.
Havre, P.A. et al., "Targeted Mutagenesis of Simian Virus 40 DNA Mediated by a Triple Helix-Forming Oligonucleotide", Journal of Virology, vol. 67, No. 12, pp. 7324-7331, 1993.
Henikoff, S. et al., "TILLING. Traditional Mutagenesis Meets Functional Genomics", Plant Physiology, vol. 135, pp. 630-636, 2004.
Henikoff, S. et al., "Amino acid substitution matrices from protein blocks", Proc. Natl. Acad. Sci. USA, vol. 89, pp. 10915-10919, 1992.
Horsch, R.B. et al., "Inheritance of Functional Foreign Genes in Plants", Science, vol. 223, pp. 496-498, 1984.
Huang, S. et al., "The *Arabidopsis* ACT11 actin gene is strongly expressed in tissues of the emerging inflorescence, pollen, and developing ovules", Plant Molecular Biology, vol. 33, pp. 125-139, 1997.
Hupp, T.R. et al., "Small Peptides Activate the Latent Sequence-Specific DNA Binding Function of p53", Cell, vol. 83, pp. 237-245, 1995.
Josefsson, L. et al., "Structure of a gene Encoding the 1.7 S Storage Protein, Napin, from *Brassica napus*", The Journal of Biological Chemistry, vol. 262, No. 25, pp. 12196-12201, 1987.
Karlin, S. et al., "Application and statistics for multiple high-scoring segments in molecular sequences", Proc. Natl. Acad. Sci. USA, vol. 90, pp. 5873-5877, 1993.
Kempin, S.A. et al., "Targeted disruption in *Arabidopsis*", Nature, vol. 389, pp. 802-803, 1997.
Klee, H. et al., "*Agrobacterium*-mediated plant transformation and its further applications to plant biology", Ann. Rev. Plant Physiol. vol. 38, pp. 467-486, 1987.
Klein, T.M. et al., "High-velocity mircoprojectiles for delivering nucleic acids into living cells", Nature, vol. 327, pp. 70-73, 1987.
Kole, C. et al., "Genetic Linkage Map of a *Brassica rapa* Recombinant Inbred Population", The Journal of Heredity, vol. 88, No. 6, pp. 553-537, 1997.
Koltunow, A.M., "Apomixis: Embryo Sacs and Embryos Formed without Meiosis or Fertilization in Ovules", The Pant Cell, vol. 5, pp. 1425-1437, 1993.
Koltunow, A.M. et al., "Apomixis: A Development Perspective", Annu. Rev. Plant Biol. vol. 54, pp. 547-574, 2003.
Konieczny, A. et al., "A procedure for mapping *Arabidopsis* mutations using co-dominant ecotype-specific PCR-based markers", The Plant Journal, vol. 4, No. 2, pp. 403-410, 1993.
Livingstone, K.D. et al., "Genome mapping in Capsicum and the Evolution of Genome Structure in the Solanaceae", Genetics, vol. 152, pp. 1183-1202, 1999.
Lloyd, A.M. et al., "Epidermal Cell Fate Determination in *Arabidopsis*: Patterns Defined by a Steroid-Inducible Regulator", Science, vol. 266, pp. 436-439, 1994.
Lotfi, M. et al., "Production of haploid and doubled haploid plants of melon (*Cucumis melo* L.) for use in breeding for multiple virus resistance", Plant Cell Rep., vol. 21, pp. 1121-1128, 2003.
Manjunath, S. et al., "Molecular characterization and promoter analysis of the maize cytosolic glyceraldehyde 3-phosphate dehydrogenase gene family and its expression during anoxia", Plant Molecular Biology, vol. 33, pp. 97-112, 1997.
Matzk, F. et al., "The Inheritance of Apomixis in *Poa pratensis* Confirms a Five Locus Model with Differences in Gene Expressivity and Penetrance", The Plant Cell, vol. 17, pp. 13-24, 2005.
Mercier, R. et al., "SWITCH1 (SWI1): a novel protein required for the establishment of sister chromatid cohesion and for bivalent formation at melosis", Genes and Development, vol. 15, pp. 1859-1871, 2001.
Metzlaff, M. et al., "RNA-Mediated RNA Degradation and Chalcone Synthase A Silencing in Petunia", Cell, vol. 89, pp. 845-854, 1997.
Mizukami, Y. et al., "Functional Domains of the Floral Regulator AGAMOUS: Characterization of the DNA Binding Domain and Analysis of Dominant Negative Mutations", The Plant Cell, vol. 8, pp. 831-845, 1996.
Moore, I. et al., "Transactivated and chemically inducible gene expression in plants", The Plant Journal, vol. 45, pp. 651-683, 2006.
Mountford, P. et al., "Dicistronic targeting constructs: Reporters and modifiers of mammalian gene expression", Proc. Natl. Acad. Sci. USA, vol. 91, pp. 4303-4307, 1994.
Napoli, C. et al., "Introduction of a Chimeric Chalcone Synthase Gene into Petunia Results in Reversible Co-Suppression of Homologous Genes in trans", The Plant Cell, vol. 2, pp. 279-289, 1990.
Naumova, T. N. et al., "Reproductive development in apomictic populations of *Arabis holboellii* (Brassicaceae)" Sex Plant Reprod., vol. 14, pp. 195-200, 2001.

(56) References Cited

OTHER PUBLICATIONS

Offringa, R. et al., "Nonreciprocal homologous recombination between *Agrobacterium* transferred DNA and a plant chromosomal locus", Proc. Natl. Acad. Sci. USA, vol. 90, pp. 7346-7350, 1993.
Paszkowski, J. et al., "Direct gene transfer to plants", The EMBO Journal, vol. 3, No. 12, pp. 2717-2722, 1984.
Pearson, W.R. et al., "Improved tools for biological sequence comparison", Proc. Natl. Acad. Sci. USA, vol. 85, pp, 2444-2448, 1988.
Piquemal, J. et al., "Construction of an oilseed rape (*Brassica napus* L.) genetic map with SSR markers", Theor. Appl. Genet., vol. 111, pp. 1514-1523, 2005.
Pradhan, A.K. et al., "A high-density linkage map in *Brassica juncea* (Indian mustard) using AFLP and RFLP markers", Theor. Appl. Genet., vol. 106, pp. 607-614, 2003.
Reddy, T.V. et al., "The *DUET* gene is necessary for chromosome organization and progression during male meiosis in *Arabidopsis* and encodes a PHD finger protein", Development ePress, vol. 130, pp. 5975-5987, 2003.
Reiser, L. et al., "The *BELL1* Gene Encodes a Homeodomain Protein Involved in Pattern Formation in the *Arabidopsis* Ovule Primordium", Cell, vol. 83, pp. 735-742, 1995.
Rong, J. et al., "A 3347-Locus Genetic Recombination Map of Sequence-Tagged Sites Reveals Features of Genome Organization, Transmission and Evolution of Cotton (Gossypium)", Genetics, vol. 166, pp. 389-417, 2004.
Scanlon, K.J. et al., "Oligonucleotide-mediated modulation of mammalian gene expression[1]", The FASEB Journal, vol. 9, pp. 1288-1296, 1995.
Schena, M. et al., "A steroid-inducible gene expression system for plant cells", Proc. Natl. Acad. Sci. USA, vol. 88, pp. 10421-10425, 1991.
Sheehy, R.E. et al., "Reduction of polygalacturonase activity in tomato fruit by antisense RNA", Proc. Natl. Acad. Sci. USA, vol. 85, pp. 8805-8809, 1988.
Sheridan, W.F. et al., "The mac1 Gene: Controlling the Commitment to the Meiotic Pathway in Maize", Genetics, vol. 142, pp. 1009-1020, 1996.
Siddiqi, I. et al., "The *dyad* gene is required for progression through female meiosis in *Arabidopsis*", Development, vol. 127, pp. 197-207, 2000.
Slocombe, S.P. et al., "Temporal and Tissue-Specific Regulation of a *Brassica napus* Stearoyl-Acyl Carrier Protein Desaturase Gene[1]" Plant Physiol., vol. 104, pp. 1167-1176, 1994.
Song, Q.J. et al., "Development and mapping of microsatellite (SSR) markers in wheat", Theor. Appl. Genet., vol. 110, pp. 550-560, 2005.
Spillane, C. et al., "Apomixis in agriculture: the quest for clonal seeds", Sex Plant Reprod., vol. 14, pp. 179-187, 2001.
Stam, M. et al., "The Silence of Genes in Transgenic Plants", Annals of Botany, vol. 79, pp. 3-12, 1997.
Sun, L. et al., "Anti-HIV Ribozymes", Molecular Biotechnology, vol. 7, pp. 241-251, 1997.
Swoboda, P. et al., "Intrachromosomal homologous recombination in whole plants", The EMBO Journal, vol. 13, No. 2, pp. 484-489, 1994.
Tanksley, S.D. et al., "High Density Molecular Linkage Maps of the Tomato and Potato Genomes", Genetics, vol. 132, pp. 1141-1160, 1992.
Qi, X. et al., "An integrated genetic map and a new set of simple sequence repeat makers for pearl millet, *Pennisetum glaucum*", Theor. Appl. Genet., vol. 109, pp. 1485-1493, 2004.
Torada, A. et al., "SSR-bases linkage map with new markers using an intraspecific population of common wheat", Theor. Appl. Genet., vol. 112, pp. 1042-1051, 2006.
Tucker, M.R. et al. "Sexual and Apomictic Reproduction in *Hieracium* subgenus *Pilosella* Are Closely Interrelated Development Pathways", The Plant Cell, vol. 15, pp. 1524-1537, 2003.
Van Dijk, P.J. et al., "Crosses between sexual and apomictic dandelions (*Taraxacum*). II. The breakdown of apomixis", Heredity, vol. 83, pp. 715-721, 1999.
Weising, K. et al., "Foreign Genes in Plants: Transfer, Structure, Expression, and Applications", Annu. Rev. Genet., vol. 22, pp. 421-477, 1988.
Wenzl, P. et al., "A high-density consensus map of barley linking DArT markers to SSR, RFLP and STS loci and agricultural traits", BMC Genomics, vol. 7, pp. 206-227, 2006.
Xu, Y. et al., "Dual roles of ATM in the cellular response to radiation and in cell growth control", Genes and Development, vol. 10, pp. 2401-2410, 1996.
Yang, W. et al., "Genetics of gametophyte biogenesis in *Arabidopsis*", Growth and Development, vol. 3, pp. 53-57, 2000.
Yin, T. et al., "Preliminary interspecific genetic maps of the *Populus* genome constructed from RAPD markers", Genome, vol. 44, pp. 602-609, 2001.
Yoon, K. et al., "Targeted gene correction of episomal DNA in mammalian cells mediated by a chimeric RNA-DNA oligonucleotide", Proc. Natl. Acad. Sci. USA, vol. 93, pp. 2071-2076, 1996.
Zhang, L.P. et al., "A molecular linkage map of tomato displaying chromosomal locations of resistance genes analogs based on *Lycopersicon esculentum*×*Lycopersicon hirsutum* cross", Genome, vol. 45, pp. 133-146, 2002.
Zhao, J,J. et al., "Generating loss-of-function phenotypes of the *fushi tarazu* gene with a targeted ribozyme in *Drosophila*", Nature, vol. 365, pp. 448-451, 1993.
Bashaw, E.C., "Registration of Nueces and Llano Buffelgrass", Crop Science, vol. 9, 396, 1969.
Chittenden, L.M. et al., "A detailed RFLP map of *Sorghum bicolor*×*S. propinquum*, suitable for high density mapping, suggests ancestral duplication of *Sorghum* chromosomes or chromosomal segments", Theor. Appl. Genet., vol. 87, pp. 925-933, 1994.
Dasgupta, S. et al., "Cloning and sequencing of 5' flanking sequence from the gene encoding 2S stroage protein, from two *Brassica* species", Gene, vol. 133, pp. 301-302, 1993.
Haig, D. et al., "Parent-Specific Gene Expression and the Triploid Endosperm", The American Naturalist, vol. 134, No. 1, pp, 147-155, 1989.
Pepin, G.W. et al., "Intraspecific Hybridization as a Method of Breeding Kentucky Bluegrass (*Poa pratensis* L.) for Turf", Crop Science, vol. 11, pp. 445-448, 1971.
Puchta, H. et al., "Homologous recombination in plants", Experientia, vol. 50, pp. 277-284, 1994.
GENBANK Accession XP_469018; GI: 50917243, 2004.
GENBANK Accession AAX95531; GI: 62733414, 2005.
GENBANK Accession AB025621 BA000015; GI: 4589427, 2004.
GENBANK Accession M63985; GI: 167128, 1993.
GENBANK Accession U09119; GI: 476215, 2001.
GENBANK Accession U93215; GI: 20198323, 2002.
GENBANK Accession Z17657; GI: 16823, 1992.
Hamant, O. et al., "Genetics of Meiotic Prophase I in Plants", Annu. Rev. Plant Biol. vol. 57, pp. 267-302, 2006.
Pawlowski, W.P. et al., "Maize AMEIOTIC1 is essential for multiple early meiotic processes and likely required for the initiation of meiosis", PNAS, vol. 106, No. 9, pp. 3603-3608, 2009.
Scott, R.J. et al., "Parent-of-origin effects on seed development in *Arabidopsis thaliana*", Development, vol. 125, pp. 3329-3341, 1998.
Pandey, K.K. et al., "'Hertwig Effect' in Plants: Induced Parthenogenesis Through the Use of Irradiated Pollen", Theor. Appl. Genet. vol. 62, pp. 295-300, 1982.
Crespel, L. et al., "AFLP-based estimation of 2n gametophytic heterozygosity in two parthenogenetically derived dihaploids of *Rosa hybrida* L.", Theor. Appl. Genet., vol. 104, pp. 451-456, 2002.
Eenink, A.H. et al., "Matromorphy in *Brassica oloracea* L. I. Terminology, Parthenogenesis in Cruciferae and the Formation and Usability of Matromorphic Plants", Euphytica, vol. 23, pp. 429-433, 1974.
Consiglio, F. et al., "Exploitation of genes affecting meiotic non-reduction and nuclear restitution: *Arabidopsis* as a model?", Sex Plant Reprod., vol. 17, pp. 97-105, 2004.
Guitton, A. et al., "Loss of Function of Multicopy Suppressor of IRA 1 Produces Nonviable Parthenogenetic Embryos in *Arabidopsis*", Current Biology, vol. 15, pp. 750-754, 2005.
Bicknell, R.A. et al., "Understanding Apomixis: Recent Advances and Remaining Conundrums", The Plant Cell, vol. 16, pp. S228-S245, 2004.

(56) References Cited

OTHER PUBLICATIONS

Grimanelli, D. et al., "Development genetics of gametophytic apomixis", Trends in Genetics, vol. 17, No. 10, pp. 597-604, 2001.

Mercier, R. et al., "The meiotic protein SWI1 is required for axial element formation and recombination initiation in *Arabidopsis*", Development, vol. 130, pp. 3309-3318, 2003.

Shonn, M.A., "Spo13 protects meiotic cohesin at centromeres in meiosis I", Genes and Development, vol. 16, pp. 1659-1671, 2002.

Abler, M.L. et al., "Isolation and characterization of a genomic sequence encoding the maize *Cat3* catalase gene", Plant Molecular Biology, vol. 22, pp. 1031-1038, 1993.

Altmann, T. et al., "Easy determination of ploidy level in *Arabidopsis thaliana* plants by means of pollen size measurement", Plant Cell Reports, vol. 13, pp. 652-656, pp. 1994.

Altschul, S.F. et al., "Basic Local Alignment Search Tool", J. Mol. Biol., vol. 215, pp. 403-410, 1990.

Assaad, F.F. et al., "Epigenetic repeat-induced gene silencing (RIGS) in *Arabidopsis*", Plant Molecular Biology, vol. 22, pp. 1067-1085, 1993.

Baulcombe, D.C., "RNA as a target and initiator of post-transcriptional gene silencing in transgenic plants", Plant Molecular Biology, vol. 32, pp. 79-88, 1996.

Bechtold, N. et al., "In *Planta Agrobacterium*-Mediated Transformation of Adult *Arabidopsis thaliana* Plants by Vacuum Infiltration", Methods in Molecular Biology, vol. 82, pp. 259-266, 1998.

Bourque, J.E., "Antisense strategies for genetic manipulations in plants", Plant Science, vol. 105, pp. 125-149, 1995.

Choi, Y. et al., "Tissue-specific and developmental regulation of a gene encoding a low molecular weight sulfur-rich protein in soybeans seeds", Mol. Gen. Genet., vol. 246, pp. 266-268, 1995.

Dellaporta, S.L., et al., "A Plant DNA Minipreparation: Version II", Plant Molecular Biology Reporter, vol. 1, No. 4, pp. 19-21, 1983.

Eastham, J.A. et al., "Use of an anti-ras ribozyme to alter the malignant phenotype of a human bladder cancer cell line", Journal of Urology, vol. 156, pp. 1186-1188, 1996.

Heiser, V. et al., "Antisense repression of the mitochondrial NADH-binding subunit of complex I in transgenic potato plants affects maile fertility", Plant Science, vol. 127, pp. 61-69, 1997.

Higgins, D.G. et al., "Fast and sensitive multiple sequence alignments on a microcomputer", CABIOS Communications, vol. 5, No. 2, pp. 151-153, 1989.

Lee, K. et al., "Genes encoding oleosins in maize kernel of inbreds Mo17 and B73", Plant Molecular Biology, vol. 26, pp. 1981-1987, 1994.

Martinez, P. et al., "Structure, Evolution and Anaerobic Regulation of a Nuclear Gene Encoding Cytosolic Glyceraldehyde-3-phosphate Dehydrogenase from Maize", J. Mol. Biol., vol. 208, pp. 551-565, 1989.

Myers, E.W. et al., "Optimal alignments in linear space" CABIOS, vol. 4, No. 1, pp. 11-17, 1988.

Needleman, S.B. et al., "A General Method Applicable to the Search for Similarities in the Amino Acid Sequence of Two Proteins", J. Mol. Biol., vol. 48, pp. 443-453, 1970.

Prins, M. et al., "RNA-mediated virus resistance in transgenic plants", Archives of Virology, vol. 141, pp. 2259-2276, 1996.

Sjodahl, S. et al., "Deletion analysis of the *Brassica napus* cruciferin gene *cru 1* promoter in transformed tobacco: promoter activity during early and late stages of embryogenesis is influenced by *cis*-acting elements in partially separate regions", Planta, vol. 197, pp. 264-271, 1995.

Smith, T.F. et al., "Comparison of Biosequences", Advances in Applied Mathematics, vol. 2, pp. 482-489, 1981.

Sokol, D. et al., "Antisense and ribozyme constructs in transgenic animals", Transgenic Research, vol. 5, pp. 363-371, 1996.

Tuskan, G.A. et al., "Characterization of microsatellites revealed by genomic sequencing of *Populus trichocarpa*", Can J. For. Res., vol. 34, pp. 85-93, 2004.

Urao, T. et al., "Molecular cloning and characterization of a gene that encodes a MYC-related protein in *Arabidopsis*", vol. 32, pp. 571-576, 1996.

Vaulont, S. et al., "Disruption of the adenosine deaminase (ADA) gene using a dicistronic promoterless construct: production of an ADA-deficient homozygote ES cell line", Transgenic Research, vol. 4, pp. 247-255, 1995.

Zhong, H.H. et al., "The circadian clock gates expression of two *Arabidopsis* catalase genes to distinct and opposite circadian phases", Mol. Gen. Genet., vol. 251, pp. 196-203, 1996.

* cited by examiner

Figure.2: Pollen is viable in the *dyad* mutant

Figure 3: Male and female meiosis in wild type and dyad

Figure 4: *dyad* mutant progeny are triploid

Figure 5: Complementation of the *dyad* mutant by *BhDYAD*

| Rice | MDAEMAAPALAAAHLLDSPMRPQVSRYYSKKRGSS-HSRNGKDDANHDESKNQSPGLPLS |
| Maize | ----------MSLFISKPQVKKYYFKKKTSSHSRNGKDDVNHDSTIQ--PRSPLS |
|  | :   *. :  : :  ****.  **  *  *** |

| Rice | RQSLSSSATHTYHTGGFYEIDHEKLPPKSPIHLKSIRVVKVSGYTSLDVTVSFPSLLALR |
| Maize | RQSLTFDAIPTYHAGAFYEIDHDKLPPKSPIHLKSIRVVKVSECTNLDITVKFPSLQALR |
|  | ****: .* .** .**:****************: *.*: .* *** |

| Rice | SFFSSSPRSCTGPELDERFVMSSNHAAR |
| Maize | SFFSSYPAPGTGPELDERFVMSSNHAAR |
|  | ***** . *.*************** |

B

| Rice | EAKQGDPRRGKDRWSAERYAAAERSLLDIMRSHGACFGAPVMRQALREEARKHIGDTGLL |
| Maize | ESKQGDPRHGKDRWSAERYAAAEKSLLNIMRSRDARFGAPVMRQVLREEARKHIGDTGLL |
|  | *.****:********:*:****..* *******:************ |

| Rice | DHLLKHMAGRVPEGSADRFRRRHNADGAMEYWLEPAELAEVRRLAGVSDPYWVPPPGWKP |
| Maize | DHLLKHMAGRVPEGSVHRFRRRHNADGAMEYWLEPAELAEVRKQAGVSDPYWVPPPGWKP |
|  | *************..*****************..******** |

| Rice | GDDVSAVAGDLLVKKVEELAEEVDGVKRHIEQLSSNLVQLEKETKSEAERSYSSRKEKY |
| Maize | GDDVSLVAGDILVKRQVEELTEEVNGVKRYIEQLLC-----KDDGDFGAERDYSSLKEKY |
|  | *** *:*::**.:**         *:* * .* **** |

| Rice | QKLMKANEKLEKQVLSMKDMYEHLVQKKGKLKKEVLSLKDKYKLVLEKNDKLEEQMASLS |
| Maize | QRAVRANEKLEKQVL-CLDMCENVVQMNGELKKEVSSFEKEYEHIADKNDKLEEQVTYLS |
|  | *:  .*********  *: :: .****** . *::*:: *:****** :  |

| Rice | SSFLSLKEQLLLPRNGDNLNMERERVEVTLGKQEGLVPGEPLYVDGGDRISQQADATVVQ |
| Maize | SSFLSFKVAPDQLVVALKLELAP----------SEAVPRCALFVASGE-----QMTGTVIQ |
|  | *****:*.  ::* :  **:.: : :         ** **: ** *.*: * .**.*: |

| Rice | VGEKRTARKSSFRICKPQGTFMWPHMASGTSMAISGGGSSSCPVASGPEQLPRSSSCPSI |
| Maize | GGQDRAERKSSFRVCKPQGKFLLPSMASG--MTIGRGASSTCPAAATPGPGIPRSTSFPS |
|  | .*::* **** .**.*:*. *****  *:   .:. :.: *:  *** * . |

| Rice | GPGGLPPSSRAPAEVVVASPLDEHVAFRGGFNTPSASSTNAAAAAKLPPLPSPTSPLQT |
| Maize | MPGLPRSSRGPVEVVAAASGLDEHVMFGAHFSTPPSASSTNDAAKLQLS-LPSPRSPLQP |
|  |    *.*.**..**** *..*:.**.*:*:*  ** ** . |

| Rice | R------ALFAAGFTVPALHNFSGLTLRHVDSSSSPSSAPCG--AREKMVTLFDGDCRGIS |
| Maize | QKLFDTVTAAASGFSPQKLMHFSGLTRRDVDTSSSSGACCGSLLEGKRVLFDADAGGIS |
|  | :      : .*.** *. :::***  .:****.: *    .*::.* **.* *** |

| Rice | VVGTELALATPSYC |
| Maize | AVGTELALATPSYC |
|  | .************* |

Figure 12

NUCLEIC ACIDS AND METHODS FOR PRODUCING SEEDS WITH A FULL DIPLOID COMPLEMENT OF THE MATERNAL GENOME IN THE EMBRYO

FIELD OF THE INVENTION

The present invention relates to the use of alleles of the DYAD gene and gene product of *Arabidopsis, Boechera*, rice and other plants to manipulate gametogenesis and seed development for the purpose of producing seeds that carry a full diploid complement of the maternal genome in the embryo. The present invention also relates to use of an altered DYAD gene for producing an unreduced female gametophyte without substantial effect on pollen development.

BACKGROUND OF THE INVENTION

The plant life cycle alternates between a diploid sporophyte generation and a haploid gametophyte generation. Meiosis represents the transition between the diploid sporophyte and haploid gametophyte phases of the plant life cycle. Meiosis leads to the formation of haploid spores. In plants, unlike animals, the meiotic products undergo additional divisions to form a multicellular haploid gametophyte. Differentiation of the gametes occurs towards the later stages of gametophyte development, following division of the meiotic products. The sexual process prior to fertilization therefore comprises two distinct stages: sporogenesis which includes meiosis and the formation of haploid spores; and gametogenesis which refers to the development of the spores into a gametophyte, comprising the gamete and associated cells required for fertilization and for supporting growth of the embryo.

Most plant species undergo sexual reproduction; however some plant species are capable of asexual reproduction. The term apomixis is generally accepted as the replacement of sexual reproduction by any of certain forms of asexual reproduction (Koltunow A. and Grossniklauss U. Annu. Rev. Plant Biol. Vol. 54: 547-74, 2003). Apomixis is a genetically controlled method of reproduction in plants, involving seed formation in which the embryo is formed without union of an egg and a sperm. There are three basic types of apomictic reproduction: 1) apospory, in which the embryo develops parthenogenetically from a chromosomally unreduced egg in an embryo sac derived from the nucellus, 2) diplospory, in which an embryo develops parthenogenetically from an unreduced egg in an embryo sac derived from the megaspore mother cell, and 3) adventitious embryony, in which an embryo develops directly from a somatic cell. The first two types of apomixis are together classified under gametophytic apomixis because in both cases the embryo develops from a female gametophyte or embryo sac, whereas in adventitious embryony the embryo develops directly from a somatic cell without an intermediate female gametophyte stage. Gametophytic apomixis therefore involves two components: i) apomeiosis, or the production of an unreduced female gametophyte (embryo sac) that retains the parental genotype, and ii) parthenogenetic development of the embryo, with or without fertilization of the central cell which develops into the endosperm.

Apomixis is thus a reproductive process that bypasses female meiosis and syngamy to produce embryos genetically identical to the maternal parent. The three types of apomixis have economic potential because they can cause any genotype, regardless of how heterozygous, to breed true. With apomictic reproduction, progeny of especially adaptive or hybrid genotypes would maintain their genotype throughout repeated life cycles. In addition to fixing hybrid vigour, apomixis can make possible commercial hybrid production in crops where efficient male sterility or fertility restoration systems for producing hybrids are not known or developed. Apomixis can therefore make hybrid development more efficient. Apomixis also simplifies hybrid production and increases genetic diversity in plant species with good male sterility systems. It would be highly desirable to introduce genes controlling obligate or a high level of apomixis into cultivated species and to be able to readily hybridize cross-compatible sexual and apomictic genotypes to produce true-breeding F1 hybrids. The transfer of apomixis to important crops would make possible development of true-breeding hybrids and commercial production of hybrids without a need for cytoplasmic-nuclear male sterility and high cost, labor-intensive production processes. An obligately apomictic F1 hybrid would breed true through the seed indefinitely and could be considered to provide a vegetative or clonal method of reproduction through the seed. The development of apomictically reproducing cultivated crops would also provide a major contribution toward the food security in developing nations (Spillane C, Steimer A, and Grossniklaus U, Sex. Plant Reprod. 14: 179-187, 2001).

In reality, most known genes controlling apomixis are found in the wild species, which are distantly related to the cultivated species. Although interspecific crosses may be possible between the cultivated and wild species, chromosome pairing between genomes is usually low or nonexistent, leading to failure of this approach.

BRIEF DESCRIPTION OF THE DRAWINGS

(FIG. 2A) Wild type. (FIG. 2B) dyad.

(FIG. 3A-C) Wild type. (FIG. 3D-F) dyad. (FIG. 3A, D) Male meiocytes at the end of meiosis 1 (telophase). (FIG. 3B, E) Male meiocyte at the tetrad stage. (FIG. 3C, F) Female meiocyte at anaphase 1. dyad undergoes an equational female meiosis.

(FIG. 4A) Somatic cell of a triploid progeny plant showing 15 chromosomes. (FIG. 4B) Male meiosis 1 in a triploid progeny plant carrying 15 chromosomes showing 9:6 segregation. (FIG. 4C) Somatic cell of a diploid progeny plant showing 10 chromosomes.

(FIG. 5A) dyad mutant showing unelongated siliques. (FIG. 5B) dyad mutant transformed with the BhDYAD gene showing elongated siliques containing seeds. (FIG. 5C) Comparison of siliques from a dyad mutant plant (1), a complemented plant (2) and a wild type plant (3). (FIG. 5D) Dissected silique from a complemented plant, showing full seed set. (FIG. 5E) Dissected silique from a wild type plant.

FIG. 7A: Resolved HinF1 digested fragments from KNEF/KNER primers amplified products. FIG. 7B: Resolved HinF1 digested fragments from KKF/KKR primers amplified products.

FIG. 8A: Inflorescence showing non-elongated silique (dyad phenotype) before and after dexamethasone treatment. The arrow indicates the position of the youngest open flower at the start of treatment. 5-7 days after the start of treatment siliques showed elongation (wild type phenotype). FIG. 8B: Isolated siliques showing sterile (dyad) phenotype before dexamethasone treatment. FIG. 8C: shows restored wild type phenotype after conditional complementation by dexamethasone treatment. FIG. 8D: Split open silique showing full seed set after dexamethasone treatment.

FIG. 9A: Cleared ovule showing dyad phenotype and absence of embryo sac at the mature ovule stage before dexamethasone treatment. FIG. 9B: Embryo sac restored after dexamethasone treatment.

FIG. 10A: Seeds from selfed wild type diploid Col-O plants are uniformly normal in size. FIG. 10B: Seeds from a tetraploid plant. FIG. 10C: Size of seeds from selfed dyad plants varies between large (L), normal (N), and shrunken (S). FIG. 10D: Maternal excess—seeds from a tetraploid female crossed to a diploid male are shrunken. FIG. 10E: Paternal excess—seeds from a tetraploid male crossed to a diploid female are larger in size when compared to seeds from a maternal excess cross.

FIG. 11 shows an alignment of the protein sequences of the DYAD protein from *Arabidopsis* (SEQ ID NO: 5), *Boechera* (SEQ ID NO: 18), rice (SEQ ID NO: 51), and from poplar (*Populus trichocarpa*) (SEQ ID NO: 26), using Clustal W as in http://www.ebi.ac.uk/clustalw with default parameters.

FIGS. 12A and 12B show alignment of the rice DYAD polypeptide sequences (SEQ ID NO: 51) with putative maize DYAD polypeptide sequences (SEQ ID NOS: 55 and 54) using Clustal W (1.82). FIG. 12A: Alignment of rice DYAD amino acids 1-147. FIG. 12B: Alignment of rice DYAD amino acids 317-803.

DISCLOSURE OF THE INVENTION

Figure 1:
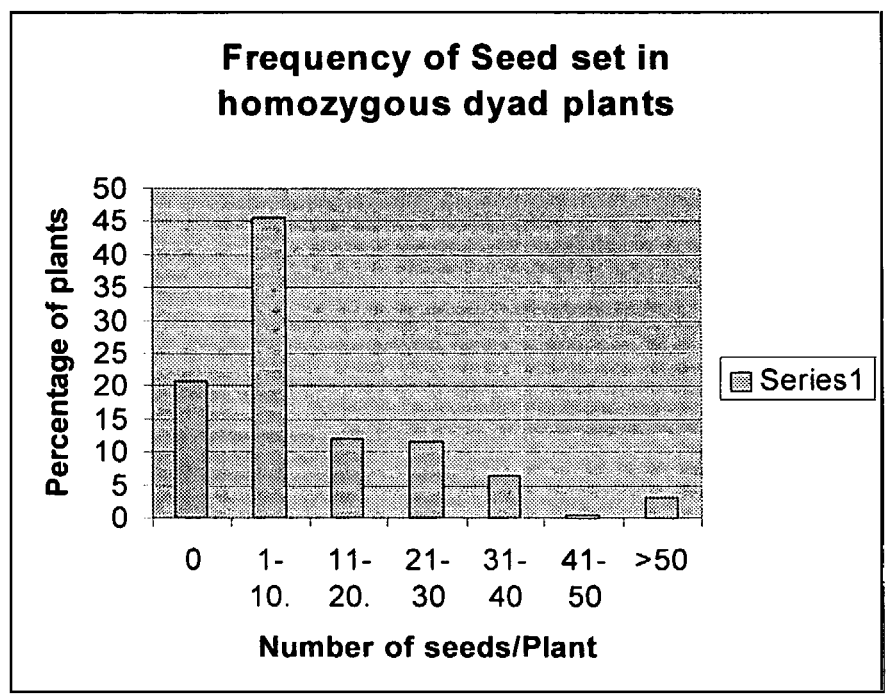
FIG. 1 represents reduced seed set in dyad mutants plants. The modal range is 1-10 seed per plant.

There are two general strategies that may be considered in order to introduce apomixis into cultivated crops. The first is by introgression from wild relatives into cultivated species. The second is by identification of genes from sexual species that can confer aspects of apomixis, followed by pyramiding these genes to produce the full repertoire of apomixis. These genes could then be introduced into cultivated crops using transgenic methods. Thus for instance, expression of one or more genes could be used to engineer apomeiosis, and these genes could be combined with another set of genes or other treatments to induce parthenogenetic embryo development. Methods for inducing parthenogenesis in plants are known in the art (See, e.g. U.S. Pat. No. 5,840,567). A preferred method for inducing parthenogenetic development for use with the present invention is to pollinate a plant using pollen that has been irradiated, thereby inactivating it for fertilization. (Pandey K. K. and Phung M., Theoret. Appl. Genet., Vol. 62:295-300, 1982; Lofti M. et al., Plant Cell Reprod., Vol. 21:1121-1128, 2003).

This method is preferred in that it has been used in a number of plant species and appears to be generally applicable, most easily to plants having incomplete flowers (monoecious and dioecious). However, it can be applied to hermaphroditic plants having complete flowers that have been made male-sterile or from which the fertile pollen has been mechanically removed or segregated.

The specific dose of radiation for sterilizing the pollen will vary depending upon the particulars of the species. In general, a dose of about 10 to 2000 Gray is sufficient. Preferably, the dose is about 100 to 500 Gray, more preferably from 200 to 250 Gray.

Successful induction of parthenogenesis can be detected by screening of seeds for the presence of embryos, for instance by dissection or by observation of the seeds on a light box after culture in liquid medium as described by Lofti M. et al., Plant Cell Reprod., Vol. 21: 1121-1128, 2003.

Introducing the apomictic trait into normally sexual crops has been attempted. Asker S. (Hereditas, Vol. 91: 231-241, 1979) reports that attempts have been unsuccessful with wheat, sugar beets, and maize. PCT publication WO 89/00810 (Maxon et al, 1989) discloses inducing an apomictic form of reproduction in cultivated plants using extracts from nondomesticated sterile alfalfa plants. When induction of male sterility was evaluated in sorghum, sunflower, pearl millet, and tomato it was reported that there was reduced seed set in sorghum, pearl millet, and sunflower and reduced fruit set in tomato.

Although apomixis is effectively used in Citrus to produce uniform and disease- and virus-free rootstock (Parlevliet J. E. et al., in Citrus. Proc. Am. Soc. Hort. Sci., Vol. 74: 252-260, 1959) and in buffelgrass (Bashaw, Crop Science, Vol. 20: 112, 1980) and Poa (Pepin et al., Crop Science, Vol. 11: 445-448, 1971) to produce improved cultivars, it has not been successfully transferred to a cultivated crop plant.

The second approach towards engineering apomixis involves the identification and manipulation of apomixis related genes from sexual species. A developmental view of apomixis has suggested that apomixis is related to sexual reproduction and involves the action of genes that also play a role in the sexual pathway (Tucker M. R. et al., Plant Cell, Vol. 15(7):1524-1537, 2003). In sexual reproduction, usually a megaspore mother cell arising from the hypodermal layer towards the apex of the developing ovule enlarges and goes through meiosis and two cell divisions to form a linear tetrad of megaspores each with a haploid chromosome number. Most commonly among different plant species, the three most apical spores degenerate while the functional chalazal spore undergoes three rounds of nuclear division accompanied by cell expansion to form an embryo sac with an egg, two polar nuclei, two synergids, and three antipodal cells. Apomixis is a process that requires multiple steps and the control of the complete pathway of apomixis as has been shown in certain species to require the action of multiple genes (van Dijk et al., Heredity, Vol. 83: 715-721, 1999; Matzk F., et al., Plant Cell, 17(1):13-24, 2005). It has been considered that individual component steps controlled by one or a subset of genes in the pathway operating in isolation would have a negative effect on fertility (Spillane, C., Steimer A. and Grossniklaus U., Sex. Plant Reprod. Vol. 14: 179-87, 2001), and that it is only the concerted action of the complete set of genes comprising the entire pathway that is able to efficiently promote apomixis. Genetic and molecular analysis of *Arabidopsis* mutants has led to the identification of a number of genes that play a role in stages of sporogenesis and gametogenesis (Yang W. C. and Sundaresan V., Curr. Opin. Plant Biol. Vol. 3(1): 53-57, 2000). The dyad mutant of *Arabidopsis* was identified as causing female sterility (Siddiqi I. et al., Development, Vol. 127(1):197-207, 2000) and its analysis showed that dyad mutant plants are defective in female meiosis. The majority of female meiocytes in the dyad mutant undergo single division meiosis to give two cells instead of four, followed by an arrest in further stages of development including gametogenesis. Male meiosis, pollen development, and male fertility in the dyad mutant was found to be normal (Siddiqi I. et al., Development, Vol. 127(1):197-207, 2000; Reddy T. V., et al., Development, Vol. 130 (24):5975-5987, 2003). Analysis of meiotic chromosomes during female meiosis indicated that homologous chromosomes do not undergo synapsis and that the reductional meiosis 1 division is replaced by an equational one (Agashe B., Prasad C. K., and Siddiqi I., Development, Vol. 129(16), 3935-3943, 2002). An independent study has led to identification of the SWI1 gene (Motamayor J. C., et al., Sex. Plant Reprod. Vol. 12:209-218, 2000; Mercier R., et al., Genes and Dev. Vol. 15: 1859-1871, 2001), which is identical to DYAD. The gene identified by these studies is hereafter referred to as the DYAD gene. The wild type DYAD gene from *Arabidopsis* encodes a protein of 639 amino acids (SEQ ID NO:5). Three alleles of the DYAD gene in *Arabidopsis* have been described. These are: i) dyad, having a truncation at amino acid 508; the resulting protein is therefore missing the C-terminal 130 amino acids present in the wild type protein; ii) swi1.1 which results in production of reduced amounts of the wild type protein causing some female meiocytes to undergo an equational meiosis 1 division whereas others undergo a reductional division; and iii) swi1.2 which creates a stop codon at position 394 and causes a female phenotype similar to dyad but in addition also causes defects in male meiosis resulting in male sterility. The position corresponding to the dyad allele in *Boechera* would be a mutation that causes a frameshift at position 508 of the amino acid sequence and results in a stop codon after ten additional codons (i.e. position 518). The corresponding positions in rice are at 563 and 572, respectively.

Without being bound by any theory of the invention, the inventors suggest that a reduction in the amount of DYAD protein having the portion of the polypeptide carboxy-terminal to position 394 (in *Arabidopsis*, and corresponding positions in other species) produces a phenotype in which female meiocytes undergo an equational meiosis 1 division, resulting in retention of the female genotype (and hence heterozygosity) in female gametes. Retention of a normal (or approximately so) amount of the DYAD protein having the domain from position 394 to position 508 (in *Arabidopsis* and corresponding positions in other species) provides for normal pollen development, whereas elimination of this domain in the plant produces a male sterile phenotype.

Prior to the making of the present invention, plants homozygous for the dyad or swi1.2 alleles had not been reported to show seed set. Plants carrying the swi1.1 allele have been reported to show reduced seed set when homozygous but the seeds that are produced have been analyzed with respect to their chromosomal constitution and found to be diploid, thereby showing that the seeds arise from a normal megasporogenesis and megagametogenesis (Motamayor J. C., et al., Sex. Plant Reprod. Vol. 12:209-218, 2000). As described previously, the spores produced as a result of the equational, single division meiosis in dyad, swi1.1, and swi1.2 remain arrested and until the making of the present invention, it was not known whether any of these had the potential to develop into female gametes. It was also not known until the making of the present invention whether the chromosomes experienced recombination during the equational single division female meiosis and as a result the products of division lost parental heterozygosity. The plausibility of recombination accompanying an equational division is supported by studies in yeast which demonstrate that diploid cells can enter meiosis, experience meiotic recombination, then withdraw from meiosis upon transfer to growth medium and divide mitotically. Such a mitotic division can lead to loss of heterozygosity for a genetic marker if recombination has taken place between the gene and the centromere (Esposito R. E. and Esposito M. S., Proc. Natl. Acad. Sci. USA Vol. 71(8): 3172-3176 1974). The present invention relates to the finding that the products of the equational meiosis 1 division seen in different dyad homozygous mutant plants are capable of giving rise to a functional unreduced embryo sac, which has the characteristic features of apomeiosis, an important component of apomixis.

The present invention relates to the use of the DYAD gene, especially mutant alleles thereof, and their gene products, of *Arabidopsis, Boechera, Rice, Populus* and other plants to manipulate gametogenesis and seed development to produce seeds whose embryonic genotype contains a full diploid complement of the maternal genome. In one embodiment triploid seeds are produced in *Arabidopsis* and other plant types.

The present invention also provides a method for the production of a heterotic plant using mutant alleles of the DYAD gene and gene product. In some embodiments, the plants and seed contain a full diploid complement of the maternal genome, and no contribution from the paternal genome, and thus represent true apomicts. In some instances of these embodiments, the plant contributing the maternal genome is a hybrid having an assortment of alleles having a desirable phenotype, and the method of the invention allows for fixation and easy propagation of that combination of alleles.

The present invention relates to the use of the DYAD gene and its gene product which leads to the formation of seeds containing a full diploid complement of the maternal genome. This invention is useful for making triploid plants which can be used for producing seedless fruit, for constructing trisomic lines for mapping studies, and for maintenance of heterozygosity of the parent plant and apomixis. The alleles of DYAD used in the present invention cause formation of an unreduced (diploid) embryo sac. The invention also relates to the use of the DYAD gene for causing formation of an unreduced embryo sac without substantially affecting pollen development. The invention further relates to the use of the DYAD gene for producing higher order polyploids by selfing of triploids, which would be useful for the purpose of generating plants with increased biomass.

It should be understood that various embodiments of the invention will exhibit different aspects of the invention, and may provide different advantages of the invention. Not every embodiment will enjoy all of the advantages of the invention Definitions The phrase "nucleic acid sequence" refers to the structure of a polymer of deoxyribonucleotide or ribonucleotide bases read from the 5' to the 3' end. In instances of a double-stranded nucleic acid, a "nucleic acid sequence" includes its complement on the other strand.

A "nucleic acid" or "polynucleotide" refers to a single-stranded or double-stranded polymer of DNA or RNA (or in some instances analogs of deoxyribonucleotides or ribonucleotides such as thiophosphate or PNA analogs, or nucleotides having derivatives of the nucleotide base) and includes chromosomal DNA, self-replicating plasmids, infectious polymers of DNA or RNA (or analogs) and DNA or RNA (or analogs) that performs a primarily structural role.

The term "polynucleotide sequence" is often interchangeable with "polynucleotide", but sometimes may refer to the information of the sequence of the molecule, rather than to the molecule per se.

A "promoter" is defined as an array of nucleic acid control sequences that direct transcription of an operably linked nucleic acid. As used herein, a "plant promoter" is a promoter that functions in plants. Promoters include necessary nucleic acid sequences near the start site of transcription, such as, in the case of a basal polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter or array of transcription factor binding sites) and a second nucleic acid sequence, wherein the expression control sequence directs transcription of the nucleic acid corresponding to the second sequence.

An "expression cassette" comprises three main elements: i) a promoter; ii) a second polynucleotide, which may be called a "coding polynucleotide" or "coding sequence" that is operably linked to the promoter and whose transcription is directed by the said promoter when the expression cassette is introduced into a cell; and iii) a terminator polynucleotide that directs cessation of transcription and is located immediately downstream of the said second polynucleotide.

The term "plant" includes whole plants, plant organs (e.g., leaves, stems, flowers, roots, etc.), seeds and plant cells and progeny of same. The class of plants which can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, and haploid. In some embodiments of the invention, it is preferred that the plant be a monoecious plant.

A polynucleotide is "heterologous to" an organism or a second polynucleotide if it has a different sequence and originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as an R1 generation transgenic plant. Transgenic plants which arise from sexual cross or by selfing are descendants of such a plant.

A "DYAD nucleic acid" or "DYAD polynucleotide sequence" used in the invention is a subsequence or full length polynucleotide sequence of a nucleic acid that encodes a polypeptide involved in control of meiosis and which, when mutated, allows for aspects of apomixis with respect to unreduced female gametophyte formation.

A "DYAD gene" comprises a DYAD nucleic acid together with a promoter and other transcription and translation control sequences that provide for expression of a DYAD gene product in a host cell, preferably in a plant.

DYAD genes are a class of plant genes that produce transcripts comprising protein-coding portions that encode polypeptides that have substantial sequence identity to the polypeptide encoded by the *Arabidopsis* DYAD gene (SEQ ID NO: 1) and have been identified in rice (Genbank ID: 62733414) and other plants. A DYAD gene has also been identified in *Populus trichocarpa* and *Zea mays* (Example 9). The DYAD gene is present in a single copy in wild-type *Arabidopsis*. Moreover the abundance of the transcript is very low as it is expressed only in the sporocytes, which make up a very small population of cells in the reproductive tissues. The *Arabidopsis* DYAD gene has previously been shown to play a critical role in meiotic chromosome organization (Agashe B., Prasad C. K., and Siddiqi I., Development Vol. 129(16): 3935-39432002). Hence its function is highly likely to be conserved in other plant species as indicated by the presence of a closely related gene in rice. Data in the present application establish that *Boechera* also has a DYAD gene closely related in sequence to the *Arabidopsis* DYAD gene.

In the case of both expression of transgenes and inhibition of endogenous genes (e.g., by RNA interference, antisense, or sense suppression) one of skill will recognize that the polynucleotide sequence used need not be identical, but may be only "substantially identical" to a sequence of the gene from which it was derived or of the polynucleotide that is to be inhibited. As explained below, these substantially identical variants are specifically covered by the term DYAD nucleic acid.

In the case where a polynucleotide sequence is transcribed and translated to produce a functional polypeptide, one of skill will recognize that because of codon degeneracy a number of polynucleotide sequences will encode the same polypeptide. These variants are specifically covered by the terms "DYAD nucleic acid". In addition, the term specifically includes those sequences substantially identical (determined as described below) with a DYAD polynucleotide sequence disclosed herein and that encode polypeptides that are either mutants of wild type DYAD polypeptides or retain the function of the DYAD polypeptide (e.g., resulting from conservative substitutions of amino acids in the DYAD polypeptide). In addition, variants can be those that encode dominant negative mutants as described below as well as nonsense mutants or frameshift mutants that result in premature translation termination.

Two nucleic acids or polypeptides are said to be "identical" if the sequence of nucleotides or amino acid residues, respectively, in the two molecules is the same when aligned for maximum correspondence as described below. The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 80%, most preferably 90-95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default values for program parameters are usually used, but alternative values for parameters can be designated. The sequence comparison algorithm then calculates the percent sequence identities for the test sequences relative to the reference sequence, based on the program parameters.

A "comparison window", as used herein, includes reference to a segment of contiguous positions, typically from 20 to 600, usually about 50 to about 200, more usually about 100 to about 150 contiguous positions, in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng D. F., & Doolittle, R. F., J. Mol. Evol. Vol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described in Altschul S. F., et al., J. Mol. Biol. Vol. 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul S. F., et al., J. Mol. Biol. Vol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. "Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid, which encodes a polypeptide, is implicit in each described sequence.

An "essentially identical sequence" is one in which the variation in sequence does not affect the intended function of the molecule.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays", Elsevier (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising DYAD nucleic acids to be used in the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1M NaCl, 1% SDS at 37° C., and at least one wash in 0.1× to 1×SSC, preferably 0.5×SSC, more preferably 0.2×SSC at a temperature of at least about 50° C., usually about 55° C., up to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

A "plant hybrid" is defined as a plant obtained by crossing two cultivars of the same plant species.

An "interspecific hybrid" is defined as a plant obtained by crossing two plants of different species.

A "female parent" in a reproductive event is defined as the plant which bears the seed.

The present invention provides the DYAD gene and its product and methods involving the application of molecular genetic approaches for the control of seed development and apomixis. The invention further relates to mutant alleles of the DYAD gene that express a truncated form of the DYAD polypeptide lacking the C-terminal portion of the native protein, and causes the development of an unreduced female gametophyte while at the same time leaving pollen development substantially unaltered as determined by pollen viability assays and microscopic examination of chromosome segregation in male meiosis. It also relates to nucleotide sequences for a female specific mutant allele of the DYAD gene, that encodes a DYAD polypeptide lacking a C-terminal portion of the native DYAD polypeptide, and such that expression of the mutant polypeptide in plants specifically leads to unreduced female gametophyte development but does not substantially affect pollen development. Such a mutant allele would express a DYAD polypeptide that, for example in the instance of a mutant allele from *Arabidopsis*, lacks all or part of the portion of the native polypeptide sequences between amino acid 509 and amino acid 639 in SEQ ID NO:5 but does contain all the region encoding polypeptide sequences up to amino acid 394. Further it also provides the nucleotide sequences that hybridize under stringent conditions to the sequence given in SEQ ID NO: 4 and which encode C-terminal deletion derivatives of native DYAD polypeptides wherein the deletion corresponds to a region between amino acid 509 and 639 in SEQ ID NO:5 as determined by comparison with SEQ ID NO:5 using a comparison window. Corresponding portions of Boechera, Rice, and Populus DYAD proteins can be identified by reference to FIG. 11. Compositions of the invention also comprise C-terminal deletion derivatives of native DYAD polypeptide sequences, and fusion proteins and the nucleic acids that encode them, formed from the above DYAD polypeptides and protein sequences, such as glucocorticoid hormone receptor proteins, that conditionally transport the fusion protein into the nucleus of a plant cell.

The methods of the invention comprise expression of DYAD polynucleotide sequences in plants to produce unreduced female gametes that retain the genotype of the parent. Production of such unreduced female gametes is useful for engineering apomixis and for fixing heterosis, as well as for production of triploid plants. In one embodiment of the invention a DYAD polynucleotide sequence may be introduced into the genome of a plant by any of several well known methods for transformation wherein it is expressed in the plant as antisense or as double-stranded RNA thereby leading to the inhibition of the endogenous DYAD gene and causing production of unreduced female gametes. In another embodiment of the invention a C-terminal deletion of DYAD polynucleotide sequences is introduced into the genome of a plant as part of an expression cassette and leads to the formation of unreduced female gametophytes, while at the same time leaving the development of pollen substantially unaffected. The expression of DYAD polynucleotide sequences in plants leading to unreduced female gametophyte formation can then be used to generate apomictic seeds by parthenogenetic development of the egg cell into an embryo. The expression of such DYAD polynucleotide sequences in plant hybrids leads to the formation of unreduced female gametes that retain the genotype of the parent thereby leading to the fixation of heterosis in the next generation. Fixation of heterosis is very useful as it would allow the multiplication of hybrid seeds by selfing without having to resort to crosses between two parent cultivars of differing genotype.

Still another embodiment of the invention is the expression of DYAD polynucleotide sequences in interspecific hybrids of plant species leading to the formation of an unreduced female gamete, which can be used for generating apomictic seed. The generation of such apomictic seeds is useful for introgressing agronomically useful genes from one plant species into another species. Yet another embodiment of the invention involves conditional or controlled expression of DYAD polynucleotide sequences or DYAD polypeptide sequences and/or the activities thereof. Such conditional expression may be used to promote the generation of unreduced female gametes and hence apomictic seeds only when desired. Methods for effecting conditional expression or activity of polynucleotide and polypeptide sequences in plants are well known in the art and include but are not limited to ethanol inducible gene expression (Devaux et al., Plant J., Vol. 36(6): 918-930, 2003), steroid hormone inducible control of activity (Schena M., Lloyd A. M. and Davis R. W., Proc. Natl. Acad. Sci. USA Vol. 88(23): 10421-10425, 1991), and Tetracycline mediated control of expression (Bohner S. et al., Plant J. Vol. 9(1): 87-95, 1999).

Example 6 below describes one embodiment of the invention wherein a homogenous population of plants showing the dyad mutant phenotype may be developed. The same may be accomplished by employing conditional DYAD RNAi or antisense in which the DYAD RNAi or antisense construct is expressed under control of a conditional promoter. Another manifestation of the invention is one in which a complementing copy of the DYAD gene is expressed in a plant under control of a conditional promoter, in a genetic background that is homozygous for a mutant allele of dyad. Still another manifestation of the invention would employ crossing a first plant carrying a DYAD RNAi or antisense construct expressed under control of a promoter that is expressed under control of a transactivator and wherein the first plant lacks the transactivator, to a second plant that expresses the transactivator.

The isolated sequences prepared as described herein can be used in a number of techniques, for example, to suppress or alter endogenous DYAD gene expression. Modulation of DYAD gene expression or DYAD activity in plants is particularly useful, for example as part of a system to generate apomictic seed.

Isolation of DYAD Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, Cold Spring Harbor Laboratory, Cold Spring Harbor, N.Y., (1989).

The isolation of DYAD nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as ovules, and a cDNA library, which contains the DYAD gene transcript, is prepared from the mRNA. Alternatively, cDNA may be prepared from mRNA extracted from other tissues in which DYAD genes or homologs are expressed.

The cDNA or genomic library can then be screened using a probe based upon the sequence of a cloned DYAD gene disclosed here. Probes may be used to hybridize with genomic DNA or cDNA sequences to isolate homologous genes in the same or different plant species. Alternatively, antibodies raised against a DYAD polypeptide can be used to screen an mRNA expression library.

Alternatively, the nucleic acids of interest can be amplified from nucleic acid samples using amplification techniques. For instance, polymerase chain reaction (PCR) technology can be used to amplify the sequences of the DYAD genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR see PCR Protocols: A Guide to Methods and Applications. (Innis, M, Gelfand, D., Sninsky, J. and White, T., eds.), Academic Press, San Diego (1990).

Appropriate primers and probes for identifying DYAD sequences from plant tissues are generated from comparisons of the sequences provided here with other DYAD related genes or the proteins they encode. For instance, *Boechera holboelli* DYAD can be compared to the closely related gene from rice (Genbank ID No. 50917243). Using these techniques, one of skill can identify conserved regions in the genes or polypeptides disclosed here to prepare the appropriate primer and probe sequences. Primers that specifically hybridize to conserved regions in DYAD related genes can be used to amplify sequences from widely divergent plant species. Standard nucleic acid hybridization techniques using the conditions disclosed above can then be used to identify full length cDNA or genomic clones.

Control of DYAD Activity or Gene Expression

Since DYAD genes are involved in controlling meiosis and ploidy of the female gametophyte, inhibition of endogenous DYAD activity or gene expression is useful in a number of contexts. For instance, inhibition of expression or modification of DYAD activity by use of an allele carrying a C-terminal deletion as described above can be used for production of fruit with absent or small/degraded seed (referred to here as "seedless fruit"). In most plant species the creation of triploids causes defects in the formation of germ cells due to unbalanced segregation of chromosomes in meiosis and leads to absence of seeds or the formation of small/degraded seeds. Inhibition of endogenous DYAD expression or activity can allow control of ploidy. Thus, in some embodiments of plants of the invention in which DYAD activity is inhibited or modified, seeds are absent or degraded and seedless fruit are produced.

Another use of nucleic acids of the invention is in the development of apomictic plant lines (i.e., plants in which asexual reproductive processes occur in the ovule, see, Koltunow A., Plant Cell, Vol. 5: 1425-1437 (1993) for a discussion of apomixis). Apomixis provides a novel means to select and fix complex heterozygous genotypes that cannot be easily maintained by traditional breeding. Thus, for instance, new hybrid lines with desired traits (e.g., hybrid vigor) can be obtained and readily maintained. One of skill will recognize that a number of methods can be used to modulate DYAD activity or gene expression. DYAD activity can be modulated in the plant cell at the gene, transcriptional, posttranscriptional, translational, or posttranslational, levels. Techniques for modulating DYAD activity at each of these levels are generally well known to one of skill and some are discussed briefly below.

Methods for introducing genetic mutations into plant genes are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, for example, X-rays, gamma rays, or fast neutrons can be used. Plants carrying mutations in DYAD gene sequences can be identified by molecular screening of pooled populations of mutagenized plants using PCR primers to amplify DYAD nucleotide sequences followed by analysis of PCR products to identify plants carrying genetic mutations in DYAD polynucleotide sequences. Methods for screening and identifying plants carrying mutations in specific gene sequences have been described (Henikoff S., Bradley T. J. and Comai L., Plant Physiol. Vol. 135(2): 630-636, 2004).

Alternatively, homologous recombination can be used to induce targeted gene disruptions by specifically deleting or altering the DYAD gene in vivo (see, generally, Grewal and Klar, Genetics 146: 1221-1238 (1997) and Xu et al., Genes Dev. 10: 2411-2422 (1996)). Homologous recombination has been demonstrated in plants (Puchta et al., Experientia 50: 277-284 (1994), Swoboda et al., EMBO J. 13: 484-489 (1994); Offtinga et al., Proc. Natl. Acad. Sci. USA 90: 7346-7350 (1993); and Kempin et al. Nature 389:802-803 (1997)).

In applying homologous recombination technology to the genes of the invention, mutations in selected portions of DYAD gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al. Proc. Natl. Acad. Sci. USA 91: 4303-4307 (1994); and Vaulont et al. Transgenic Res. 4: 247-255 (1995) are conveniently used to increase the efficiency of selecting for altered DYAD gene expression in transgenic plants. The mutated gene will interact with the target wild-type gene in such a way that homologous recombination and targeted replacement of the wild-type gene will occur in transgenic plant cells, resulting in suppression of DYAD activity. Alternatively, oligonucleotides composed of a contiguous stretch of RNA and DNA residues in a duplex conformation with double hairpin caps on the ends can be used. The RNA/DNA sequence is designed to align with the sequence of the target DYAD gene and to contain the desired nucleotide change. Introduction of the chimeric oligonucleotide on an extrachromosomal T-DNA plasmid results in efficient and specific DYAD gene conversion directed by chimeric molecules in a small number of transformed plant cells. This method is described in Cole-Strauss et al. Science 273:1386-1389 (1996) and Yoon et al. Proc. Natl. Acad. Sci. USA 93: 2071-2076 (1996).

Gene expression can be inactivated using recombinant DNA techniques by transforming plant cells with constructs comprising transposons or T-DNA sequences. DYAD mutants prepared by these methods are identified according to standard techniques. For instance, mutants can be detected by PCR or by detecting the presence or absence of DYAD mRNA, e.g., by Northern blots or Reverse Transcription followed by PCR (RT-PCR). Mutants can also be selected by assaying for alterations in fertility, female meiosis, and megaspore development.

The isolated nucleic acid sequences prepared as described herein can also be used in a number of techniques to control endogenous DYAD gene expression at various levels. Subsequences from the sequences disclosed here can be used to control transcription, RNA accumulation, translation, and the like.

A number of methods can be used to inhibit gene expression in plants. For instance, RNA interference (RNAi) technology can be conveniently used. To achieve this, a nucleic acid segment from the desired gene is cloned as an inverted repeat in which the two copies are separated by a spacer which may be commonly between 5 and 2000 nucleotides in length, preferably between 30 and 500 nucleotides, and more preferably between 50 and 200 nucleotides. The inverted repeat is operably linked to a promoter followed by a terminator such that both copies will be transcribed and give rise to an RNA species that is self-complementary along all or part of its length. The construct is then transformed into plants and double stranded RNA is produced.

As another instance, antisense technology can be conveniently used to inhibit DYAD gene expression. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque Plant Sci. (Limerick) 105: 125-149 (1995); Pantopoulos In Progress in Nucleic Acid Research and Molecular Biology, Vol. 48. Cohn, W. E. and K. Moldave (Ed.). Academic Press, Inc.: San Diego, Calif., USA; London, England, UK. p. 181-238; Heiser et al. Plant Sci. (Shannon) 127: 61-69 (1997)) and by preventing the accumulation of mRNA which encodes the protein of interest, (see, Baulcombe Plant Mol. Bio. 32:79-88 (1996); Prins and Goldbach Arch. Virol. 141: 2259-2276 (1996); Metzlaff et al. Cell 88: 845-854 (1997), Sheehy et al., Proc. Nat. Acad. Sci. USA, 85:8805-8809 (1988), and Hiatt et al., U.S. Pat. No. 4,801,340).

The nucleic acid segment to be introduced generally will be substantially identical to at least a portion of the endogenous DYAD gene or genes to be repressed. The sequence, however, need not be perfectly identical to inhibit expression. The vectors of the present invention can be designed such that the inhibitory effect applies to other genes within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full-length nucleotides should be used, though a sequence of at least about 100 nucleotides is preferred, a sequence of at least about 200 nucleotides is more preferred, and a sequence of about 500 to about 1700 nucleotides is especially preferred.

A number of gene regions can be targeted to suppress DYAD gene expression. The targets can include, for instance, the coding regions, introns, sequences from exon/intron junctions, 5' or 3' untranslated regions, and the like. In some embodiments, the constructs can be designed to eliminate the ability of regulatory proteins to bind to DYAD gene sequences that are required for its cell- and/or tissue-specific expression. Such transcriptional regulatory sequences can be located either 5'-, 3'-, or within the coding region of the gene and can be either promote (positive regulatory element) or repress (negative regulatory element) gene transcription. These sequences can be identified using standard deletion analysis, well known to those of skill in the art. Once the sequences are identified, an antisense construct targeting these sequences is introduced into plants to control gene transcription in particular tissue, for instance, in developing ovules and/or seed.

Oligonucleotide-based triple-helix formation can be used to disrupt DYAD gene expression. Triplex DNA can inhibit DNA transcription and replication, generate site-specific mutations, cleave DNA, and induce homologous recombination (see, e.g., Havre and Glazer J. Virology 67:7324-7331 (1993); Scanlon et al. FASEB J. 9:1288-1296 (1995); Giovannangeli et al. Biochemistry 35:10539-10548 (1996); Chan and Glazer J. Mol. Medicine (Berlin) 75: 267-282 (1997)). Triple helix DNAs can be used to target the same sequences identified for antisense regulation.

Catalytic RNA molecules or ribozymes can also be used to inhibit expression of DYAD genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. Thus, ribozymes can be used to target the same sequences identified for antisense regulation. A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, luceme transient streak virus, velvet tobacco mottle virus, solanum nodiflorum mottle virus and subterranean clover mottle virus. The design and use of target RNA-specific ribozymes is described in Zhao and Pick Nature 365:448-451 (1993); Eastham and Ahlering J. Urology 156:1186-1188 (1996); Sokol and Murray Transgenic Res. 5:363-371 (1996); Sun et al. Mol. Biotechnology 7:241-251 (1997); and Haseloff et al. Nature, 334:585-591 (1988).

Another method of suppression is sense cosuppression. Introduction of nucleic acid configured in the sense orientation has been shown to be an effective means by which to block the transcription of target genes. For an example of the use of this method to modulate expression of endogenous genes (see, Assaad et al. Plant Mol. Bio. 22: 1067-1085 (1993); Flavell Proc. Natl. Acad. Sci. USA 91: 3490-3496 (1994); Stam et al. Annals Bot. 79: 3-12 (1997); Napoli et al., The Plant Cell 2:279-289 (1990); and U.S. Pat. Nos. 5,034,323, 5,231,020, and 5,283,184).

The suppressive effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used. In addition, the same gene regions noted for antisense regulation can be targetted using cosuppression technologies.

Alternatively, eliminating the proteins that are required for DYAD cell-specific gene expression may modulate DYAD activity. Thus, expression of regulatory proteins and/or the sequences that control DYAD gene expression can be modulated using the methods described here.

Another method is use of engineered tRNA suppression of DYAD mRNA translation. This method involves the use of suppressor tRNAs to transactivate target genes containing premature stop codons (see, Betzner et al. Plant J. 11:587-595 (1997); and Choisne et al. Plant J. 11: 597-604 (1997). A plant line containing a constitutively expressed DYAD gene that contains an amber stop codon is first created. Multiple lines of plants, each containing tRNA suppressor gene constructs under the direction of cell-type specific promoters are also generated. The tRNA gene construct is then crossed into the DYAD line to activate DYAD activity in a targeted manner. These tRNA suppressor lines could also be used to target the expression of any type of gene to the same cell or tissue types.

The production of dominant-negative forms of DYAD polypeptides that are defective in their abilities to bind to other proteins is a convenient means to inhibit endogenous DYAD activity. This approach involves transformation of plants with constructs encoding mutant DYAD polypeptides that form defective complexes with endogenous proteins and thereby prevent the complex from forming properly. The mutant polypeptide may vary from the naturally occurring sequence at the primary structure level by amino acid substitutions, additions, deletions, and the like. These modifications can be used in a number of combinations to produce the final modified protein chain. Use of dominant negative mutants to inactivate target genes is described in Mizukami et al. Plant Cell 8:831-845 (1996).

Another strategy to affect the ability of a DYAD protein to interact with itself or with other proteins involves the use of antibodies specific to DYAD. In this method cell-specific expression of DYAD-specific Abs is used inactivate functional domains through antibody:antigen recognition (see, Hupp et al. Cell 83:237-245 (1995)).

Use of Nucleic Acids of the Invention to Enhance DYAD Gene Expression

Isolated sequences prepared as described herein can also be used to introduce expression of a particular DYAD nucleic acid to enhance or increase endogenous gene expression. Enhanced expression can also be used, for instance, to increase vegetative growth by preventing the plant from setting seed. Where overexpression of a gene is desired, the desired gene from a different species may be used to decrease potential sense suppression effects.

One of skill will recognize that the polypeptides encoded by the genes of the invention, like other proteins, have different domains that perform different functions. Thus, the gene sequences need not be full length, so long as the desired functional domain of the protein is expressed.

Modified protein chains can also be readily designed utilizing various recombinant DNA techniques well known to those skilled in the art and described in detail, below. For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. Ann. Rev. Genet. 22:421-477 (1988). A DNA sequence coding for the desired polypeptide, for example a cDNA sequence encoding a full-length protein, or a fusion protein of DYAD to an intracellular localization sequence, or a truncated DYAD protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region. The 1'- or 2'-promoter derived from T-DNA of *Agrobacterium tumafaciens*, and other transcription initiation regions from various plant genes known to those of skill. Such genes include for example, ACT11 from *Arabidopsis* (Huang et al. Plant Mol. Biol. 33:125-139 (1996)), Cat3 from *Arabidopsis* (GenBank No. U43147, Zhong et al., Mol. Gen. Genet. 251:196-203 (1996)), the gene encoding stearoyl-acyl carrier protein desaturase from *Brassica napus* (Genbank No. X74782, Solocombe et al. Plant Physiol. 104:1167-1176 (1994)), GPc1 from maize (GenBank No. X15596, Martinez et al. J. Mol. Biol 208:551-565 (1989)), and Gpc2 from maize (GenBank No. U45855, Manjunath et al., Plant Mol. Biol. 33:97-112 (1997)).

Alternatively, the plant promoter may direct expression of the DYAD nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers. Promoters that direct expression of nucleic acids in ovules, flowers, or seeds are particularly useful in the present invention. As used herein a seed-specific promoter is one that directs expression in seed tissues. Such promoters may be, for example, ovule-specific (which includes promoters which direct expression in maternal tissues or the female gametophyte, such as egg cells or the central cell), embryo-specific, endosperm-specific, integument-specific, seed coat-specific, or some combination thereof. Examples include a promoter from the ovule-specific BEL1 gene described in Reiser et al. Cell 83:735-742 (1995) (GenBank No. U39944), and the promoter from the male meiocyte specific DUET gene (Reddy T. V., et al., Development, Vol. 130 (24):5975-5987, 2003). Other suitable seed specific promoters are derived from the following genes: MAC1 from maize (Sheridan et al. Genetics 142:1009-1020 (1996), Cat3 from maize (GenBank No. L05934, Abler et al. Plant Mol. Biol. 22:10131-1038 (1993), the gene encoding oleosin 18 kD from maize (GenBank No. J05212, Lee et al. Plant Mol. Biol. 26:1981-1987 (1994)), viviparous-1 from *Arabidopsis* (Genbank No. U93215), the gene encoding oleosin from *Arabidopsis* (Genbank No. Z17657), Atmyc1 from *Arabidopsis* (Urao et al. Plant Mol. Biol. 32:571-576 (1996), the 2S seed storage protein gene family from *Arabidopsis* (Conceicao et al. Plant J. 5:493-505 (1994)) the gene encoding oleosin 20 kD from *Brassica napus* (GenBank No. M63985), napA from *Brassica napus* (GenBank No. J02798, Josefsson et al. JBL 26:12196-1301 (1987), the napin gene family from *Brassica napus* (Sjodahl et al. Planta 197:264-271 (1995), the gene encoding the 2S storage protein from *Brassica napus* (Dasgupta et al. Gene 133:301-302 (1993)), the genes encoding oleosin A (Genbank No. U09118) and oleosin B (Genbank No. U09119) from soybean and the gene encoding low molecular weight sulphur rich protein from soybean (Choi et al. Mol. Gen., Genet. 246:266-268 (1995)).

In addition, the promoter sequences from the DYAD genes disclosed here can be used to drive expression of the DYAD polynucleotides of the invention or heterologous sequences. If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene, which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. Embo J. 3:2717-2722 (1984). Electroporation techniques are described in Fromm et al. Proc. Natl. Acad. Sci. USA 82:5824 (1985). Ballistic transformation techniques are described in Klein et al. Nature 327:70-73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. Science 233:496-498 (1984), and Fraley et al. Proc. Natl. Acad. Sci. USA 80:4803 (1983).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. Ann. Rev. of Plant Phys. 38:467-486 (1987).

The nucleic acids of the invention can be used to confer desired traits on essentially any plant. Thus, the invention has use over a broad range of plants, including species from the genera *Anacardium, Arachis, Asparagus, Atropa, Avena, Brassica, Citrus. Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna*, and *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Seed obtained from plants of the present invention can be analyzed according to well known procedures to identify plants with the desired trait. If antisense or other techniques are used to control DYAD gene expression, RT-PCR or Northern blot analysis can be used to screen for desired plants. In addition, the presence of fertilization independent reproductive development can be detected. Plants can be screened, for instance, for the ability to form embryo-less seed, form seed that abort after fertilization, or set fruit in the absence of fertilization. These procedures will depend in part on the particular plant species being used, but will be carried out according to methods well known to those of skill.

The following examples are given by way of illustration of the present invention and should not be construed to limit the scope of present invention.

EXAMPLE 1

The Dyad Mutant Shows Defective Female Fertility and Reduced Seed Set

The dyad mutant was isolated in a screen for sterile mutants of *Arabidopsis* among a population of EMS mutagenized M2 plants (Siddiqi I. et. al. Development Vol. 127(1): 197-207 (2000)) Analysis of fertility by reciprocal crosses indicated that the mutant was female sterile but male fertile. Analysis of female sporogenesis and ovule development indicated that dyad underwent a defective female meiosis resulting in a single meiotic division due to defective progression through the meiotic cell cycle, followed by arrest and failure to develop female gametes in the majority of ovules. Analysis of female meiosis by observations of chromosome spreads of meiocytes indicated that female meiosis was abnormal in the dyad mutant: chromosomes failed to synapse and underwent an equational division instead of a reductional division, which would normally take place at meiosis 1 (Agashe B., Prasad C. K., and Siddiqi I., Development Vol. 129(16): 3935-3943 (2002)).

As shown in FIG. 1, seed set in the dyad mutant is highly reduced when compared to wild type and variation was observed in the degree of seed set among different dyad mutant plants. The seed set was sporadic and random such that no uniformity in terms of number was observed among the plants in the population. The mode for seed set was 1-10 per plant but ranged upto a maximum of about 275 that was observed rarely (1 in 500 plants).

EXAMPLE 2

Male Meiosis and Fertility are Normal in the Dyad Mutant

Figure 2:
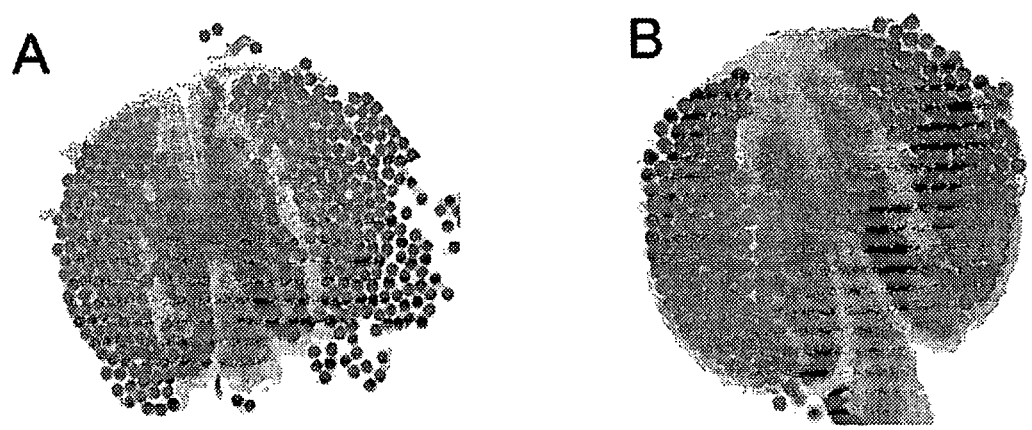
FIGS. 2A and 2B show normal pollen viability in dyad mutant plants using Alexander staining.
Figure 3:
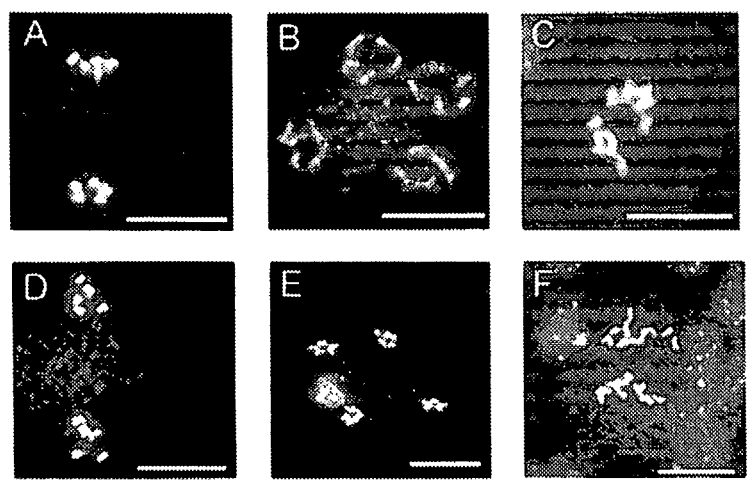
FIGS. 3A to 3F show male and female meiosis in wild type and the dyad mutant.

Pollen viability was examined using Alexander staining and pollen were found to be fully viable and comparable to wild type (FIG. 2). Examination of male meiosis by analysis of chromosome spreads of meiocytes indicated that male meiosis was normal and resulted in the production of a tetrad of haploid spores (FIG. 3). Male meiosis, male fertility, and pollen development as well as function were therefore normal in the dyad mutant. On the other hand female meiosis is abnormal in dyad. Synapsis of homologous chromosomes is not seen to occur and the reductional meiosis 1 division of wild type female meiosis (FIG. 3C) is replaced by an equational one in dyad (FIG. 3E).

EXAMPLE 3

Seeds Obtained from the Dyad Mutant Germinate to Give Triploid Plants

Figure 4:
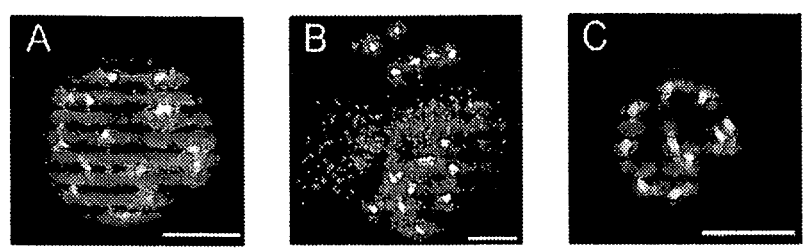
FIGS. 4A to 4C show chromosome ploidy of representative progeny of a diploid dyad mutant plant.

It is possible that the seeds produced in the dyad mutant arise from a normal meiosis in a small minority of female meiocytes, which go on to give rise to a normal functional embryo sac that is then fertilized by haploid pollen to develop into seed. If this was the case, these seeds would represent escapees from the abnormal female meiosis which takes place in the dyad mutant. To examine this possibility, seeds (n=169) from dyad plants were germinated and found to germinate with high efficiency (>90%) and produce morphologically normal seedlings except a few that gave abnormal seedlings (10%). No instances of variations in shape, symmetry and number of cotyledons were observed in the germinating seedlings. This is in contrast to seedlings derived from other meiotic mutants such as AtSpo11-1 and AtDmc1 which undergo random segregation of chromosomes in meiosis 1, resulting in higher proportion of aneuploid progeny that show a range of developmental abnormalities at the seedling stage (Grelon M. et al., The EMBO J., Vol 20: 589-600, 2001, Couteau F. et al., Plant Cell, Vol. 11(9): 1623-1634, 1999). Subsequent vegetative growth of seedlings on transferring to soil also was normal and gave rise to plants in which vegetative growth was similar to wild type as well as the parent dyad mutant plants. The main difference observed was in flower size when the plants started bolting. In a majority of the plants (n=41/52) a comparative increase in flower size was observed as to wild type. The increased flower size could possibly be attributed to increase in vigour or favourable environmental influences. Since the plants are grown in controlled environment we ruled out the latter possibility. The other possible reason for increase in floral organ size might be increase in ploidy. Increase in ploidy is manifested by the increase in size of vegetative and floral structures, particularly the pollen grains (Altmann T., et al., Plant Cell Reports. Vol. 13: 652-656, 1994). Flower buds from randomly picked plants were examined for their ploidy level by analysis of chromosomes in somatic cells and in male meiocytes. It was found by examination of meiotic chromosome spreads that in 17/19 cases the plants were triploid and the remaining 2 were found to be diploid (FIG. 4). Since pollen development and male meiosis are normal in the dyad mutant whereas a reductional female meiosis is replaced by an equational division, these results suggest that the majority of the seeds which are triploid arise from fertilization of an unreduced (diploid) egg cell by a normal haploid sperm and do not arise from a normal female meiosis in a minority of ovules. i.e. the majority of seeds do not represent escapees from the abnormal meiosis.

EXAMPLE 4

Triploid Plants Derived from Dyad Show Retention of all Heterozygous Markers The triploid seeds formed in the dyad mutant could be the product of fertilization of an unreduced embryo sac by a normal haploid pollen which would be consistent with the equational female meiosis that takes place in dyad. If such an unreduced embryo sac is formed from an unreduced megaspore that arises from the product of an equational, division of the megaspore mother cell wherein chromosomes remain as univalents and fail to undergo recombination, then the genotype of the unreduced embryo sac would be identical to that of the diploid parent plant. Hence if the parent plant is heterozygous for a molecular marker then the triploid progeny will also be heterozygous for that marker. If a marker unlinked to the centromere is considered in a heterozygous condition, then in the complete absence of recombination 100% transmission of parental heterozygosity will be achieved in the resultant female gamete and the triploid progeny. If recombination and crossing over take place then 100% heterozygosity will not be maintained in the resultant triploid progenies. For a marker that is unlinked to the centromere, one can expect homozygosity in the unreduced embryo sac at a frequency of 33% and in the triploid progeny at a frequency of 16.7% whereas in the complete absence of recombination there will be no homozygotes. The formation of unreduced embryo sacs without loss of heterozygosity is highly desirable for engineering apomixis and fixation of heterosis. We used microsatellite to measure loss of heterozygosity among the triploid progeny of dyad mutant plants. The dyad mutant plants were identified in a segregating F2 population of a cross between wild type Nossen (No-O) and dyad mutant Columbia (Col) ecotypes. Candidate markers distributed across each of the five *Arabidopsis* chromosomes and unlinked to the centromere (>35 cM) were obtained from the TAIR database (www.arabidopsis.org). The parent plants used to generate the F2 population were examined to ascertain the polymorphism and based on the results we choose 5 different markers (Table 1) on 4 different chromosomes to genotype 50 F2 dyad mutant plants and identify those markers for which each plant was heterozygous. Selfed seeds were collected from the 50 F2 plants individually and grown as 50 different families consisting of a variable number of siblings. This gave a total of 196 plants distributed across 50 families. All members of each family were genotyped with respect to those markers for which the parent plant was heterozygous so as to give between 74-119 plants distributed across all the 50 F2 families for each marker.

TABLE 1

Marker analysis of progeny of dyad plants to measure loss of heterozygosity and recombination.

| Marker | Chromosome No. | Position in linkage map (cM) | Centromere position (approx) (cM) | No. of plants analysed | No of homozygotes[a] |
|---|---|---|---|---|---|
| nga168 | 2 | 73.77 | 15 | 119 | 11 (9.24) |
| nga6 | 3 | 86.41 | 49 | 108 | 7 (6.48) |
| nga162 | 3 | 20.5 | 49 | 74 | 8 (10.81) |
| nga1107 | 4 | 104.73 | 28 | 107 | 11 (10.28) |
| nga225 | 5 | 14.32 | 71 | 103 | 9 (8.73) |

[a]Figure in brackets in the column 6 represents the percentage homozygotes of the total plants analysed for that marker.

Out of 196 plants screened we obtained 35 plants that were homozygous for at least one marker for which the parent plant was heterozygous. The ploidy of 22 of these 35 plants was determined by carrying out meiotic chromosome spreads. It was found that 21 were diploid and another a hyperdiploid having 13 chromosomes. Hence according to the analysis loss of heterozygosity was found almost exclusively only in diploids. Of the plants that did not show loss of heterozygosity, 15 plants were chosen at random from separate F2 families and examined for their ploidy. All 15 were found to be triploid.

The results therefore indicate that there is no loss of heterozygosity in triploids which make up the majority class of progeny from a diploid dyad mutant plant. The failure to find loss of heterozygosity in triploids also rules out an alternative possible mechanism for their formation, namely polyspermy, i.e. fertilization of a haploid female gamete by two separate male gametes, which would also predict loss of heterozygosity. Our findings show that the triploid progeny of dyad mutant plants arise from fertilization of an unreduced embryo sac that retains the genotype of the parent plant. The formation of an unreduced embryo sac is a key aspect of apomixis.

EXAMPLE 5

Isolation and Functional Characterization of the DYAD Homologue from *Boechera holboelli*

Figure 5:
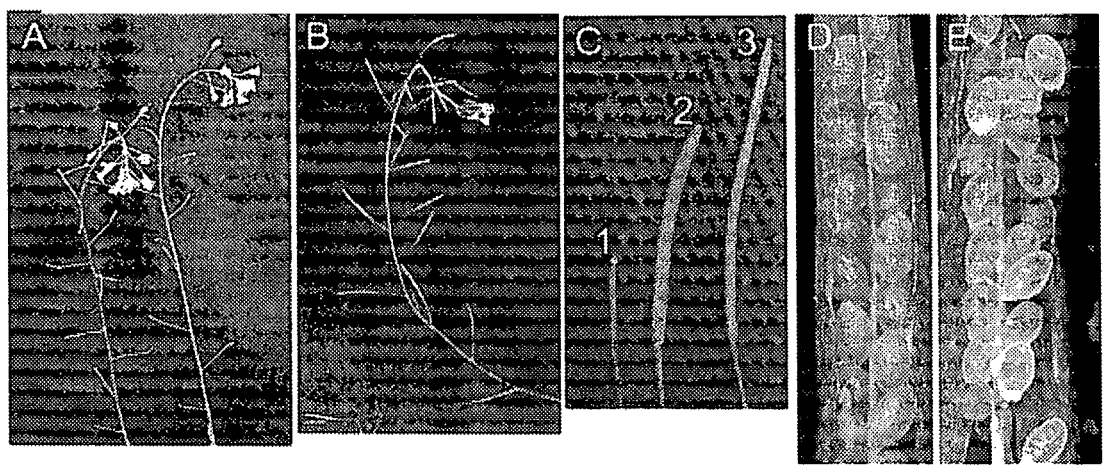
FIGS. 5A to 5E show complementation of the dyad mutant by the *Boechera holboelli* DYAD homologue.

The 3 kB genomic coding region of the DYAD homolog from the facultatively apomictic *Boechera holboellii* accessions Diploid Greenland and Triploid Colorado (Naumova T. N., et al., Sex. Plant Reprod. Vol. 14: 195-200, 2001) were cloned using Bho5Bam (SEQ ID NO:39) and Bho3Bam (SEQ ID NO:40) primers. The BhDYAD genomic clone (SEQ ID NO:16) was operably linked to the *Arabidopsis* DYAD promoter and used to transform dyad mutant plants to test for complementation. The BhDYAD cDNA was also amplified and sequenced (SEQ ID NO: 17). *Agrobacterium* mediated in planta vacuum infiltration transformation mobilized the expression construct to F1 plants that were heterozygous for dyad. We obtained 42 transformants out of which 9 transformants were homozygous for the dyad mutant allele as determined by the CAPS and microsatellite markers that flank the dyad locus (Agashe B, Prasad C. K., and Siddiqi I., Development Vol. 129(16): 3935-3943 (2002)). Of the 9 transformants 4 transformants showed complementation of the dyad mutant phenotype, which can be judged by the well elongated siliques (FIG. 5) which were found to contain full seed set. The remaining 5 plants were sterile possibly due to cosuppression.

Growth of *Arabidopsis* Plants

The *Arabidopsis* strain harboring the dyad mutant was as described earlier (Siddiqi I., et. al., Development. Vol. 127(1): 197-207 (2000)). F2 population used for microsatellite marker analysis was derived from a cross between the strain No-O (Nossen ecotype) and dyad mutant in the Col-0 ecotype background as described (Siddiqi I., et. al., Development. Vol. 127(1): 197-207 (2000)). Plants were grown in a controlled environment as described (Siddiqi I., et. al., Development. Vol. 127(1): 197-207 (2000)).

For germinating seeds in Petri plates, the seeds were surface sterilized with ethanol for 10 min followed by treating them with 0.025% mercuric chloride for 5 min. Further the seeds were washed three times with sterile water to remove any traces of mercuric chloride. The seeds were resuspended in lukewarm 0.5% top agar and evenly spread on MS agar plates (0.7%) supplemented with 2% Sucrose. The plates were allowed to dry for an hour in a laminar flow hood and the plates were sealed with parafilm and kept in a cold room at 4° C. for stratification for 3 days. After that the plates were shifted to a growth chamber. Germination frequencies were counted after two weeks thereafter.

For growing seeds in the pots, the synthetic medium used for growing plants was prepared by mixing an equal proportion of Soilrite: Perlite: Vermiculite (Keltech Energies Ltd., Karnataka 574 108, India). The pot mixture was evenly applied to the pots perforated at the bottom allowing capillary rise and the pots were soaked in 1× MS Solution containing Major Salts: $CaCl_2$ (4 mM), $MgSo_4$ (1.5 mM), $KNO_3$ (18.8 mM), $NH_4NO_3$ (20.6 mM), $KH_2Po_4$ (1.25 mM pH 5.6), Fe-EDTA (20 mM) to which 1 ml (1000×) Minor Salts: ($H_3BO_3$ (70 mM), $MnCl_2$ (14 mM), $CuSO_4$ (0.5 mM), $ZnSO_4$ (1 mM), $NaMoO_4$ (0.2 mM), NaCl (10 mM), $CoCl_2$ (0.01 mM)) was added per liter. The seeds were evenly spread on the surface of the pot and covered with Saran wrap and kept at 4-8° C. for 3 days for stratification and then shifted to a growth chamber. In case of transplantation, the pots were covered with Saran wrap after the seedlings were transferred to the soil medium and directly placed in the growth chamber. The Saran wrap was removed once the plants were established in the potting mix. Watering was done at regular intervals using distilled water.

Seed Set Analysis

The F2 segregating population harbouring a dyad mutation in the Col-0 ecotype background was used for scoring the frequency of seed set in the dyad homozygous plants dyad mutant plants were allowed to grow till their final stage when the plant ceased to flower. After this stage watering was withheld to allow the siliques to reach harvest maturity. Meanwhile the lowest siliques that turn yellow and were about to shatter were individually split open and the seeds if any were harvested on a single plant basis. Likewise necessary seeds were harvested at regular intervals to avoid possible seed loss. Finally the seeds collected were pooled on a single plant basis to count for the total number of seeds per plant.

Pollen Viability

Vital staining for microspores in the anther was done as described (Alexander M. P., Stain Technol. Vol. 44(3): 117-122, 1971).

Meiotic Spreads

Analyses of male and female meiotic spreads are as described (Agashe B, Prasad C. K., and Siddiqi I., Development Vol. 129(16): 3935-3943 (2002))

Plant DNA Isolation

Genomic DNA for microsatellite marker analysis was isolated according to the method described by Dellaporta S. L., et al., Plant Mol. Bio. Rep., Vol. 1: 19-21 (1983) with minor modifications. About 500 mg of leaf tissue was collected from an individual plant in 1.5 ml eppendorf tubes and snap frozen in liquid nitrogen. Then the tissue was ground to a fine powder using a micropestle. To this powder was added 200 µl of freshly prepared extraction buffer (100 mM Tris (pH 8), 50 mM EDTA, 500 mM NaCl, 1.4% SDS, and 10 mM β-mercaptoethanol) and was finely homogenized with the micropestle. Then equal volume of 2×CTAB was added and the mixture was gently vortexed. Then the mixture was incubated at 65° C. for 5 minutes in a shaking water bath. After that the sample was allowed to cool and an equal volume of 24:1 chlorofom: isoamyl alcohol was added and mixed gently and centrifuged for 10 min at 13000 rpm. The aqueous phase containing the DNA was transferred to a fresh eppendorf tube and ⅔ volumes of ice-cold isopropanol was added to precipitate the DNA. The DNA was pelleted down by centrifugation at 4° C. at 13000 rpm for 20 min. The DNA pellet was given a 70% ethanol wash and the pellet was air dried for 30 minutes and suspended in 50 µl of sterile water or TE buffer (pH 8.0) containing DNAse free RNAse (20 ug/ml).

Marker Analysis

Based on the parental survey of Col-0 and No-O ecotypes 5 microsatellite markers from 4 different chromosomes that are reasonably unlinked to the centromere were chosen. These markers were used on a F2 (No-O×Col-0 (dyad)) segregating population to choose dyad plants that are heterozygous for a given marker. Seeds from these dyad plants were collected and germinated in individual petri plates such that each progeny constitutes a sib of the particular mother dyad plant. Likewise data on sibs from various plants that were heterozygous for a given marker was considered together for marker analysis.

The list of microsatellite markers and their location are as described in the Table 1. The primer sequences used for amplifying the microsatellites are from the TAIR website (www.arabidopsis.org):

```
nga 162
nga162F         SEQ ID NO: 6 nga162R         SEQ ID NO: 7 nga225
nga225F         SEQ ID NO: 8 nga225R         SEQ ID NO: 9 nga168
nga168F         SEQ ID NO: 10 nga168R         SEQ ID NO: 11 nga1107
nga1107F        SEQ ID NO: 12 nga1107R        SEQ ID NO: 13 nga6
nga6F           SEQ ID NO: 14 nga6R           SEQ ID NO: 15
```

PCR was performed in 1×PCR buffer (Perkin Elmer) containing 2 mM MgCl, 0.2 mM each dNTP, 1 unit of Taq DNA polymerase (Perkin-Elmer/Cetus), and 5 pmoles of forward and reverse flanking primers at an annealing temperature of 55° C. with an extension at 72° C. for 20 seconds. The PCR products were resolved on a 8% polyacrylamide gel at 150V for 3 hrs and stained with ethidium bromide and captured using Syngene gel documentation system (Synoptics Inc. UK).

Plant Materials

The facultatively apomictic diploid Greenland and triploid Colorado accessions of Boechera holboellii were a kind gift from Kim Boutilier (Naumova T. N., et al., Sex. Plant Reprod. Vol. 14: 195-200, 2001). The plants were grown on pots containing the medium as described for Arabidopsis and grown under conditions identical to those for Arabidopsis.

Cloning of DYAD Promoter

A 1.8 kb DYAD promoter region was amplified from Col-0 ecotype using the primers pg2r4 (SEQ ID NO: 48) and PDY-BAM (SEQ ID NO: 47) and the product was cloned into a pGEMT vector (Promega) as per manufacturer's instructions.

Cloning of DYAD Homolog from Boechera holboellii

The genomic coding region of the Arabidopsis DYAD homolog from Boechera holboellii (BhDYAD) was amplified with primers harboring a BamHI site on the 5' end: Bho5BAM (SEQ ID NO: 39) and Bho3BAM. (SEQ ID NO: 40) The resultant 3 kb fragment was cloned into pGEMT.

Construction of Binary Vector pCAMBIA1300 Driving BhDYAD Under Arabidopsis DYAD Promoter The Bh DYAD was released from pGEMT as a 3 kb BamHI fragment and cloned into a pCAMBIA 1300 vector carrying a plant selectable marker hygromycin. The orientation was checked using the primers BDY3 (SEQ ID NO: 36) and OCSR (SEQ ID NO: 38). The 1.6 kb DYAD promoter region (SEQ ID NO: 22) was released as a SacI fragment from the pGEMT vector and inserted upstream of a BhDYAD in pCAMBIA1300 vector. The orientation of the promoter with respect to the BHDYAD genomic sequence was confirmed using primers ismr4 (SEQ ID NO: 37) and bdy1 (SEQ ID NO:35)

Triparental Mating

The transfer of the above constructed binary vector pCAMBIA into Agrobacterium (AGL1) was by triparental mating as described (Agashe B, Prasad C. K., and Siddiqi I, Development, Vol. 129(16): 3935-3943 (2002)).

Transformation of Arabidopsis Plants

For complementation analysis of BhDYAD, F1 plants of Col-0 x dyad were transformed with the construct carrying BHDYAD driven by the Arabidopsis DYAD promoter. Agrobacterium mediated in planta vacuum infiltration transformation was carried out according to Bechtold N. and Pelletier G., Methods Mol. Biol., Vol. 82: 259-66 (1998).

Selection of Transformants

T0 seeds from vacuum infiltrated F1 plants were plated onto a petri plate containing 0.8% Bacto Agar, 1 mM KNO3 and 1% Sucrose with 20 µg/ml hygromycin. After cold stratification for 3 days the plates were transferred to a growth chamber. The transformants that are resistant to hygromycin can be identified as early as 5 days post transfer by virtue of well elongated root, erect hypocotyl and well spread cotyledonary leaves. The selected transformants were further transferred to MS plates containing hygromycin and after resistance is established they were finally transferred to soil medium. Furthermore the plants were checked for the present of insert using bdy3 and OCSR primer as described earlier.

Genotyping for Zygosity at Dyad Locus

The three genotypes from the segregating dyad F2 population were identified by the codominant CAPS markers (Konieczny A. and Ausubel F. M., Plant J., Vol. 4(2): 403-410, 1993) and variable microsatellites. The flanking sequences of the dyad mutant allele are derived from Landsberg erecta ecotype and those from the wild type allele have Colombia ecotype sequence. Thus the SNPs in these flanking sequences were utilized to develop CAPs marker that are closely linked to and flanking either side of the dyad locus (KNEF (SEQ ID NO:31) and KNER(SEQ ID NO:32), KKF(SEQ ID NO:33) and KKR(SEQ ID NO:34)) and microsatellite marker primers (KMF (SEQ ID NO:29 and KMR (SEQ ID NO:30)) that are closely linked to DYAD (Agashe B, Prasad C. K., and Siddiqi I., Development Vol. 129(16): 3935-3943 (2002)). The genotyping at the dyad locus using the above markers was as described (Agashe B, Prasad C. K., and Siddiqi I., Development Vol. 129(16): 3935-3943 (2002)).

RNA Isolation and cDNAs Synthesis

Well-developed single buds from a diploid Greenland plant were used for total RNA isolation by TriZol reagent (Invitrogen) as per manufacturer's instructions. 4 µg of total RNA was used for first strand cDNA synthesis using the Superscript™ Choice system for cDNA synthesis (GIBCO BRL). The cDNA was further amplified for cloning by using primers 5RF3(SEQ ID NO: 41) and Bho3BAM (SEQ ID NO:40). The resultant 1.9 KB fragment was cloned into pGEMT and sequenced. Results are presented in the Sequence Listing as SEQ ID NO: 17. The amino acid sequence of the corresponding DYAD protein is shown in SEQ ID NO: 18.

EXAMPLE 6

Construction of a Conditional Allele of DYAD and Development of a Homogenous Population of Transgenic Plants Showing the Dyad Mutant Phenotype The strategy used to construct a conditional allele of the DYAD gene was based on fusing the hormone binding domain of the rat glucocorticoid receptor (GR) (SEQ ID NO: 27) to the C-terminus of DYAD and integrating the fusion construct into the genome of plants that were homozygous for the dyad mutant allele (dy/dy). The DYAD-GR fusion protein on its own is not capable of complementing the dyad mutant because the GR domain confers cytoplasmic localization in the absence of steroid hormone, whereas the site of action of DYAD is in the nucleus. However in presence of the steroid hormone, the fusion protein is released from the cytoplasmic binding site and becomes capable of translocating to the nucleus where it can complement the dyad mutant. The steps in the construction were the following: the plant binary vector pBI101.3 was digested with BamHI plus SacI to remove the GUS reporter gene and replace it with a BamHI-SacI fragment comprising the GR domain (A. M. Lloyd et al., Science 266, 436-439 (1994)).

Figure 6:
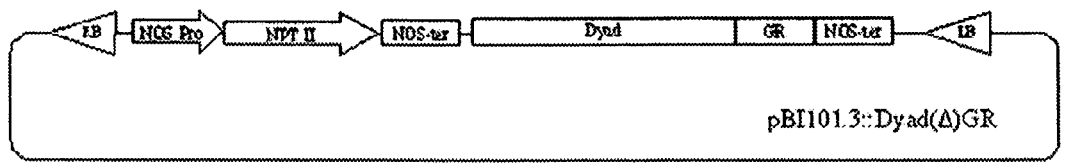
FIG. 6 is a diagram showing the pBI101.3::Dyad::(Δ)GR cassette used to construct a DYAD conditional complementation line.

The resultant plasmid was named pBI101.3::GR. Next the primers DyCF (SEQ ID NO: 43) and DyPB (SEQ ID NO: 42) (which contains sequence to modify the termination codon and introduce restriction sites for BamHI and PstI) were used to PCR amplify a 304 bp C-terminal region of the DYAD gene. The modified sequence was cloned as a 216 bp PstI fragment into the pBS (KS)::Dyad plasmid which carried a 5.8 kb genomic clone (SEQ ID NO:28) that contained the entire DYAD gene corresponding to coordinates 9684 to 3878 of the P1 clone MFG13 (Acc No. AB025621) to give pBS (KS)::Dyad*. The resulting plasmid contained a DYAD gene whose termination codon TGA had been replaced by GGG and which also carried a BamHI site along with the replaced codon. The 269 bp SalI-BamHI fragment from pBSII(KS):: Dyad* which contained nucleotides 9684 to 9416 of MFG13 was cloned into pBI101.3::GR following digestion with SalI plus BamHI. The remaining portion of DYAD from 9417-5335 was then cloned as a BamHI-BamHI fragment from pBS(KS)::Dyad* into the product of the previous step which resulted in an in frame fusion of the GR domain to the C-terminus of DYAD. The final plasmid named pBI101.3::DyadΔGR is represented in FIG. 6.

Figure 7:
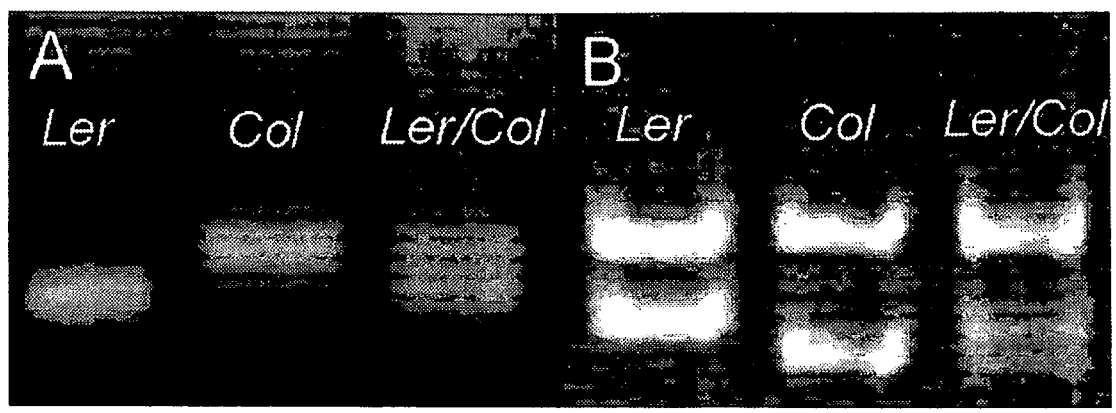
FIGS. 7A and 7B are polyacrylamide gels showing CAPS polymorphism for genotyping the endogenous locus of DYAD as described in Example 6.
Figure 8:
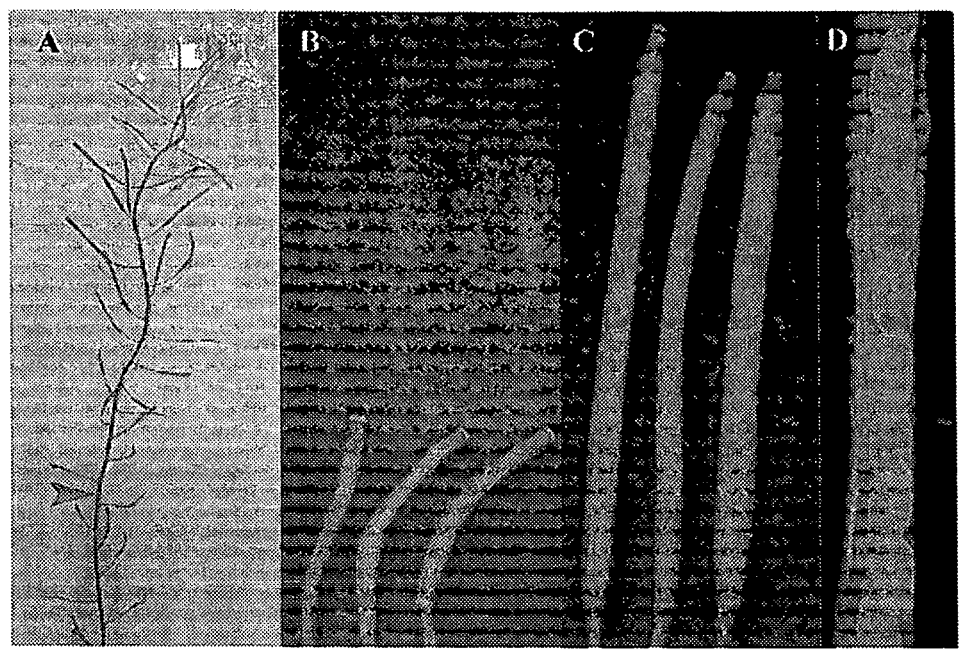
FIGS. 8A to 8D illustrate the conditional complementation of the dyad phenotype in Example 6.
Figure 9:
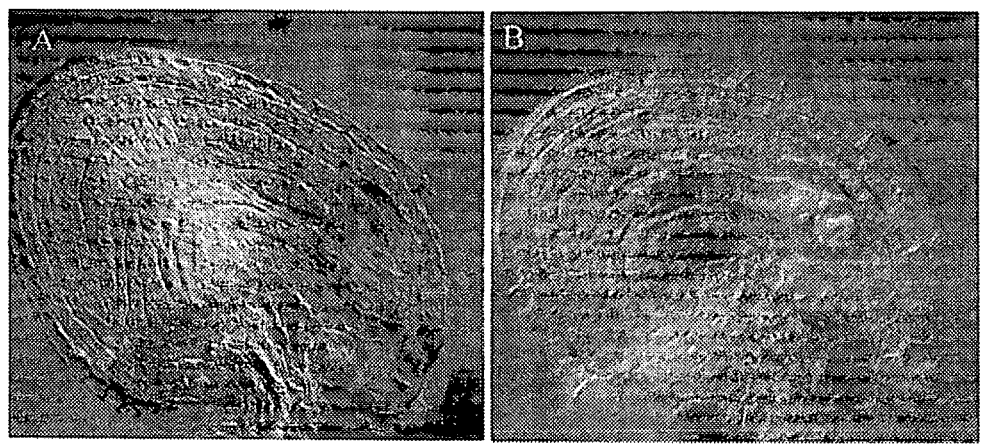
FIGS. 9A and 9B show the morphology of the ovule after conditional complementation of dyad phenotype in Example 6.

The construct was introduced into the *Agrobacterium* strain AGL1 by triparental mating using the helper *E. coli* strain HB101[pRK2013]. The T-DNA region was transformed into *Arabidopsis* plants (T0) that were heterozygous for the dyad mutant allele (+/dy) by in-planta transformation (Bechtold N, and Pelletier G., Methods Mol. Biol., Vol. 82: 259-66, 1998). Kanamycin resistant T1 seedlings were selected by plating the seeds on MS agar plates containing kanamycin (50 mg/liter) and transferred to MS+kanamycin plates to confirm the resistant phenotype. Transformants were further identified by PCR using DyCF (SEQ ID NO:43) and GRrev (SEQ ID NO:44) primers. Confirmed kanamycin resistant seedlings were transferred to soil and grown to the adult stage. Following bolting and development of the first 8-10 siliques, plants were watered every three days with 10 µM dexamethasone in addition to being sprayed daily with 10 µM dexamethasone+0.015% Silwet L-77. It was noted that several plants that showed sterility prior to dexamethasone treatment developed fertile siliques 5-7 days after the start of dexamethasone treatment. Part of the plant material was used for Southern analysis to determine copy number of the insertion and also genotyped with respect to the dyad locus using PCR based CAPS markers closely linked to and flanking the dyad locus. The dyad mutant was originally isolated in the Ler background and then introgressed into the Col strain. Hence the Ler allele of the CAPS markers is diagnostic for the dyad mutant whereas the Col allele is indicative of wild type (FIG. 7). Single copy insertions were identified among plants that had at least one copy of the dyad mutant allele and seeds from these plants were plated on MS+kanamycin plates. Kanamycin resistant seedlings were transferred to soil and genotyped with respect to the dyad locus. Plants that were homozygous for the dyad mutant allele were identified and grown to adulthood. Following bolting all the plants were fed with water during the initial phase upto the opening of the first 8-10 flowers followed by watering with a solution containing dexamethasone as described above. As an example, one line No. 33 shown in FIG. 8 gave dyad mutant plants (dy/dy) all of which showed sterility during the initial phase of reproductive growth and which became fertile following dexamethasone treatment. Ovules from buds isolated prior to dexamethasone treatment showed the dyad mutant phenotype, whereas those isolated after dexamethasone treatment showed the wild type phenotype (FIG. 9). Seeds were collected from homozygous dyad mutant plants to give T3 families and T3 families which were homozygous for the DYAD-GR insertion were identified by screening for families, which gave all kanamycin resistant seedlings. These results exemplify construction of a conditional allele of DYAD and its introduction into plants thereby giving plants that show the dyad mutant phenotype under one set of conditions (the absence of dexamethasone) and the wild type phenotype when fed (or sprayed) with dexamethasone. These results also enable development of a homogenous population of plants all of which show the dyad mutant phenotype.

```
Glucocorticoid receptor domain sequence used in
       this study (914 bp) (SEQ ID NO: 27)

GGATCCTGAAGCTCGAAAAACAAAGAAAAAAATCAAAGGGATTCAGCAAG
CCACTGCAGGAGTCTCACAAGACACTTCGGAAAATCCTAACAAAACAATA
GTTCCTGCAGCATTACCACAGCTCACCCCTACCTTGGTGTCACTGCTGGA
GGTGATTGAACCCGAGGTGTTGTATGCAGGATATGATAGCTCTGTTCCAG
ATTCAGCATGGAGAATTATGACCACACTCAACATGTTAGGTGGGCGTCAA
GTGATTGCAGCAGTGAAATGGGCAAAGGCGATACCAGGCTTCAGAAACTT
ACACCTGGATGACCAAATGACCCTGCTACAGTACTCATGGATGTTTCTCA
TGGCATTTGCCCTGGGTTGGAGATCATACAGACAATCAAGTGGAAACCTG
CTCTGCTTTGCTCCTGATCTGATTATTAATGAGCAGAGAATGTCTCTACC
CTGCATGTATGACCAATGTAAACACATGTCTGTTTGTCTCCTCTGAATTAC
AAAGATTGCAGGTATCCTATGAAGAGTATCTCTGTATGAAAACCTTACTG
CTTCTCTCCTCAGTTCCTAAGGAAGGTCTGAAGAGCCAAGAGTTATTTGA
TGAGATTCGAATGACTTATATCAAAGAGCTAGGAAAAGCCATCGTCAAAA
GGGAAGGGAACTCCAGTCAGAACTGGCAACGGTTTTACCAACTGACAAAG
CTTCTGGACTCCATGCATGAGGTGGTTGAGAATCTCCTTACCTACTGCTT
CCAGACATTTTTGGATAAGACCATGAGTATTGAATTCCCAGAGATGTTAG
CTGAAATCATCACTAATCAGATACCAAAATATTCAAATGGAAATATCAAA
AAGCTTCTGTTTCATCAAAAATGACTGACCTAGTTCTAGAGCGGCCGCCA
CCGCGGTGGAGCTC
```

```
Dyad Genomic sequence used for cloning as a SalI
     fragment in pBS(KS)::Dyad (5807 bp)
                (SEQ ID NO: 28)

GTCGACTTTTTGTTTGACCAGTGTATTTGGTTTGACTTCAGATTTGGCAA
GTACGAAGCTTATGCGCTTTTGCAATCGAAACAAGGGAAAAATCTGTACT
TTGTTAGCTGCGTGACTTGAGCTCTTTGGTCCGGAGACGGTAGAAGACGA
CAAAGCACTGACCTTTCATCTCTCGGCGATCGAAAAAATCACTCTCTTTC
CTCATCAGACCCGACCCGTTATGAAGGTATCCAGACCCGTTTATTTTGAT
CCATCTCATAGTCGGATCCCCAAAAAAATTCAGCTTAGATTGGCCCATTT
AGGCCCGTTTACAGTTTTTTACTTTTTTCTTAATTATCTTTTTAACATCT
TACATTATACATATTTGACTCAACAAAAAAATATAACTTAAATGTATTGT
TGACTGTTTTTGATAATTAAGAAAAAAATATTTTTAAATTATTAAAAATA
```

Dyad Genomic sequence used for cloning as a SalI
fragment in pBS(KS)::Dyad (5807 bp)
(SEQ ID NO: 28)

```
TTGTTGACTCAACAAAAAAATATAACTTAAATGTATTGGGCAAATAATCA
TGGTCATAAGTCCTCAAGCTTATTATTTGTTTTGATTGGTTTAAATACTT
TATAAAAAAAATATCAATTATATCATGTTATTACGTAAATTAAGCTTTTT
GATTTTAAAAAAGCTTCAGCTCAATAAAGAAAAACAGATTCAGTTATCAT
TGGAGTATAAAATTGGTCGATACATTAGAGACATTAATCCTTACATCATA
AACAATTTAATGTGAATAAAACATCATAAATCACATATCATTATCCGAAA
ATAATCATATGTAAGAATAATCACTGTGACAAAAAAAAAAAACAATTCCT
CACGTGTGTAGTCGGTCCCCACTCTAGTAGCAGTAGCTTAATGATGCCTT
CTCCGCACGTGTAACACGAAATTTATTCGCTACGGCCAATTACATTAACC
TTCAGGTCTTATCACCGTTAAATTTTCAAAATGACACACGTGGCATCAAT
CCGTAATATCACTACGTCTGCTTTCAATCTTTCATTGTAGATGATTTCGT
ACACCAATTTCCGCGAACGTTTACAGTTTAGATACAGTTTGAGGGCAAAT
CTGTCAATATACGCCAACTTGCTGCGAAAGCAATATAGTCACGTGCCGTG
CACACGCATATAAGACTCACACACTCACACCACTCTCTCTCTCTCTCTAA
CCTCATATATAAAGCCACCTCCCAGATTCATTAAATGCGACATTTCAAAA
CTTTTCTTTTTGCTGTCTTCCCCATAAGCTCTCTGCTGATTAAAAAGATT
TTCTGGTATAAAACAAAATTCTTCAAATATTTCTGGGTTTATGTTTTCTC
TCTATTTCTCAGAAATGCTTTAATTTCTCCATCCGCGTCCATGTTTTTTT
TTCTCCGTTGCTGATTTTGATTTTTTTAATCCAGTGAAAAGGAGGAACGA
AGATTATCGAGAGCAAAAATCATGAGTGTAAGATCTCTCTCGCTCTCAGA
TTTTATTTTTTTCGCTGTGATATAAATGGCTCAGTCACTATCAGTCTCA
TGATGAGAAAAATAAAACTCATCACCGCTTGATTCTGTTTCCTTAGTGTC
TCCCACGCGCGTACCAGAAAGCGCGTGTGTTTCTTGTTATACTCGCAG
AGTCAGGTTTTTCAAATATATTCTCTCCAGGCAGCAGCAACAACAACAA
ACCGATTTTTTCATTATTCCTTATAACAATTTTTGATTCTCCAGAAAAAA
AATATCTCTCTTAGTTTTTCTCTTGTTCTACAGAGTACGATGTTCGTGAA
ACGGAATCCGATTAGAGAAACCACCGCCGGGAAAATCTCTTCGCCGTCGT
CACCGACTTTGAATGGTAAACTACTGAAGCTATAGTTTCTTCGTTTTTGT
TGATTTTCTCGCTTCTCTTCTAATTTCTGAATTTTTGGTTTGGGTTTGTT
CTTACAGTTGCAGTCGCGCATATAAGAGCTGGATCTTATTACGAAATCGA
TGCTTCGATTCTTCCTCAGAGATCGCCGGAAAATCTTAAATCGATTAGAG
TCGTCATGGTATTCACTCGATTCTCTGCTTTTTTCACCTTTTATTATAGA
CAGATCTCGTTTTTTGTTGTTCGTCTGGGTTTTCGAGTGATTTTTAAGG
TTTATTGATGCAGGTGAGCAAAATCACGGCGAGTGACGTGTCTCTCCGGT
ACCCAAGCATGTTTTCACTCCGATCGCATTTCGATTACAGTAGGATGAAC
CGGAATAAACCGATGAAGAAGAGGAGTGGTGGTGGTCTTCTTCCTGTTTT
CGACGAGAGTCATGTGATGGCTTCGGAGCTAGCTGGAGACTTGCTTTACA
GAAGAATCGCACCTCATGAACTTTCTATGAATAGAAATTCCTGGGGTTTC
TGGGTTTCTAGTTCTTCTCGCAGGAACAAATTTCCAAGAAGGGAGGTGGT
TTCTCAACCGGCGTACAATACTCGTCTCTGTCGCGCTGCTTCACCGGAGG
GAAAGTGCTCGTCTGAGCTGAAATCGGGAGGGATGATCAAGTGGGGAAGG
AGATTGCGTGTGCAGTATCAGAGTCGGCATATTGATACTAGGAAGAATAA
GGAAGGTGAGGAGAGTTCTAGAGTGAAGATGAAGTTTACAAGAAGAAG
AGATGGAGAAAGAAGAGGATGATGATGATGGGAATGAAATAGGAGGCACT
AAACAAGAGGCAAAGGAGATAACTAATGGAAATCGTAAGAGAAAGCTGAT
TGAATCAAGTACTGAGAGACTCGCTCAGAAAGCTAAGGTTTATGATCAGA
AGAAGGAAACTCAAATTGTGGTTTATAAGAGGAAATCAGAGAGGAAGTTC
ATTGATAGATGGTCTGTTGAGAGGTAAAATGCATAAAAATTAACGAATTT
TATGATCTCTGAATTTGGATTTTCCTTGGTTCTATTGATTGATTGTGGTT
AATTTTGAAGGTACAAACTAGCTGAGAGGAACATGTTAAAAGTGATGAAG
GAGAAGAATGCAGTGTTTGGCAACTCCATACTCAGGCCAGAGTTGAGGTC
AGAAGCAAGGAAGCTGATTGGTGACACAGGTCTATTGGATCATCTGCTTA
AGCACATGGCTGGTAAGGTGGCTCCTGGAGGTCAAGATAGGTTTATGAGA
AAGCACAATGCAGATGGGGCAATGGAGTATTGGTTGGAGAGTTCTGATTT
GATTCACATAAGGAAAGAAGCAGGAGTTAAAGATCCTTACTGGACTCCTC
CACCTGGTTGGAAGCTTGGTGACAACCCTTCTCAAGATCCTGTCTGCGCT
GGAGAAATCCGTGACATCAGAGAAGAATTAGCTAGCCTGAAAAGGTAGAA
AAGTTATTGAATTGGTTATACGATCATCTCCCTTTAGTTGTCTTATTGCA
ATTTTAACTCATGTCTGTCTTGGTCTTGAGAAGAGAATTGAAGAAACTTG
CGTCAAAGAAGGAAGAGGAGGAGCTTGTTATCATGACTACGCCTAATTCT
TGTGTTACTAGTCAGAATGATAATCTGATGACTCCAGCAAAGGTAAGAGC
TCGAAACAATAGCTGAGGCCTCTCTCTTGTGAAAATGTTTTATGCTACTT
TGTGAACATCTCTGCTGCTTTTTCTTAGGAAATCTACGCTGATCTGCTGA
AAAAGAAATACAAAATTGAGGACCAGCTAGTGATTATTGGAGAAACCTTG
CGTAAAATGGAGGTATGTATATCCCTAGATTGAGTTTCCAAGTAGACACA
AACCCTTACTTAAAATGTAAAATCTTGATTTAGTAACTATCACAAGTAGT
CATAGGAAACTCCCTTGGAGGATAACAGTGAACCATGTAAAATGGGCCCA
TTTAGCGTATGTGATAAATGATTTCCTCTGTCTCTATGAGAGACCACTTT
GCTGATAGTCGAATAATGATGAAACATTTGTGTTACTATAAATGCAAATA
TTGCAGGAAGACATGGGATGGCTTAAGAAAACAGTGGACGAGAACTATCC
TAAAAAGCCAGACTCAACAGAGACACCTTTGCTACTAGAGGATTCACCAC
CAATACAGACACTAGAAGGAGAAGTGAAGGTGGTGAACAAGGGTAACCAA
ATCACAGAGTCACCTCAAAACAGAGAAAAAGGAAGGAAGCATGATCAACA
AGAAAGATCACCACTTTCACTAATAAGCAACACTGGTTTCAGAATCTGCA
GGCCTGTGGGGATGTTCGCATGGCCCCAATTGCCTGCTCTTGCTGCTGCT
ACTGATACTAATGCTTCTTCGCCAAGTCACAGACAAGCCTACCCATCCCC
TTTTCCAGTCAAGCCACTTGCAGCTAAGCGTCCTCTTGGCTTGACGTTTC
CCTTCCACCATCATACCCGAAGAAGCTCCCAAGAATCTCTTCAACGTTTGA
AGTTGTCACTGGAAACTGATGCATCAGATCTTACTTTCCCTACAAGTAAG
CTGATGTGAACTGGTAAGGTCTCTTCCATGAAATATATAATAACTTACAA
GCGAGCAGGTATTTAAAAGTACCACTTATATTTATATAAGGAACTATATT
TATGGGAATAATTTGGCAACTTTTTGAAATTATTCCTCTTTAATTTAGGG
ATTTTACGTCTCTGGTTATTAATTATATATAGAGAGAGATGATTTGAAAT
AGAGAGGCTTATCATAGGAATATATTCTTTTGAAAGACAGGGATCATCAT
ATTCTGTATTACTGAACAATTTCTATAATGATACAGTTATATATATATAT
ATATACTTATTATTCAATTCCTAGCGCTTTTGATTTTAAATATATTATTT
TCGTGTAGTTGATTAATTTTGAAAAACTTGTATTACGCATATGAATTATG
TCCCGTTGATCTATAAAAATCATATTTTGCGATTAAGCACAAACTATAAA
AGTATGTTTAAGTTCCTGCGGGTTGACCAGTTTCACTTTAAAATCTTGGT
CTTTGGGATGAGTTTGCCGATAAATTTTGTGACTTATGGTTATCTAATAA
TACGAATGTTATACTTTCCAAAATTTGAAAAAAACAATATGAATACTTTA
TTATTATCTTTTTCCTTCCATTTCTCTTCCCGCGTTTTGTTGTTCGACCG
ATCTTGTAGTACATGTGTTCTAATTTGAACGTCGAGAACCATTAAAGAAG
GAAGAAAGAAAAGAAAAAAAAACTTTTTTCTCATTTCGAGATTTCCTA
ACCATTTGGTGGTGCAGGTTTAAGTTTCGCTCGCTCTCCTAAAACCAAAC
GTCCAAACCCGTTCTCTAGACTAGTTCTGCTGCGAAACACGACACACACC
AAGTCACCAATATTACTTGAATCCACGTCAAATAAACAATGGTCATTCAA
TATGGTTAATGCAACACTCGAGTAACTTTATTTTCAAAGAAATTTGCACA
AAGTCATGTTATGATATGATGTATAATATTTGTGTATATATCCGGCCAAA
AAACATAACAAGTTTTTTATAAAAAAAAAAATTAATTATATATCTAAAAT
ATAGAATAGCTAGTAATAAAACTAGTGAGAACAAATTTAAAACAAATTA
AGCAACTATGTTATTTGCCAAATTGACAATTTTAAATATTATGGCGTATT
TAAAAAAAATTAGGAGCCACTTGTGATTTATTTGTATCAACTAGTAAATT
TTAAACATAAAAATCATTTATAAATATAAATAAATATTATCATATTTATG
TAGAAAGAGTCTCATCAGTCTGATAGTCAATCACTTGTGCGCAAAGAAAT
TTGACGAAAGGGGTTACAAAAAAATGGCCAGCACAGCATCATCATGTCCC
CGACCTTATATTATAAGATTTGTATATTTTATCCATAAATTGTATATAAC
CGTCGAC
```

EXAMPLE 7

Figure 10:
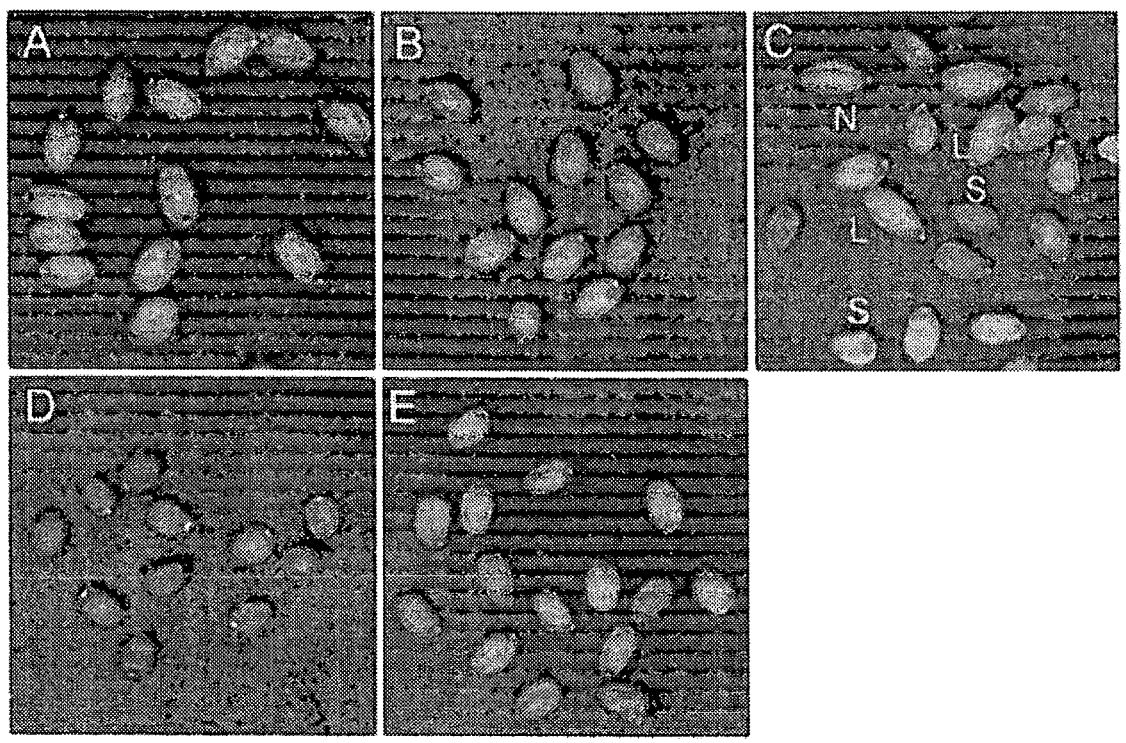
FIGS. 10A to 10E show the variation in size of seeds produced by the dyad mutant and differences in size of seeds obtained from reciprocal crosses between diploid and tetraploid *Arabidopsis* strains.
Figure 13:
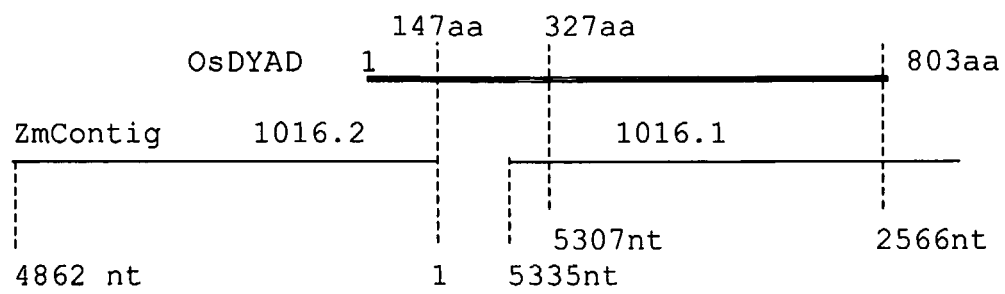
FIG. 13 shows mapping of the DYAD polypeptide sequence from rice onto two *Zea mays* contigs identified as comprising DYAD-encoding sequences.

Selfed Seed of the Dyad Mutant that are Triploid (3n) Contain a Diploid (2n) Contribution from the Female Gamete Reciprocal crosses were carried out between tetraploid (4n) and diploid (2n) wild type *Arabidopsis* plants. In both cases the seeds that are produced are triploid. However, when the male parent was tetraploid and the female parent was diploid, the seeds that were produced were large, whereas when the male parent was diploid and the female parent was tetraploid the seeds were shrunken. These results are depicted in FIG. 10 and the 100-seed weights for each category of seed are shown in Table 2.

TABLE 2

Weight of 100 seeds obtained from plants of various crosses

| Seed Category | Seed weight in μg |
|---|---|
| Diploid Columbia WT seeds | 2142 |
| Tetraploid Landsberg erecta | 3352 |
| Diploid Columbia × Tetraploid La-er μg (Paternal excess) | 3004 |
| Tetraploid La-er × Diploid Columbia (Maternal excess) | 1302 |
| dyad bigger category seeds | 3453 |
| dyad Normal category seeds | 2012 |
| dyad shrunken category seeds | 1379 |

These findings reproduce what is known in the prior art (Scott R J et al., Development 125, 3329-3341, 1998). Without being bound by any theory of mechanism, the nonequivalence of the paternal and material genomes in the regulation of seed development has been explained according to the parent-offspring conflict theory (Haig D. and Westoby M., Am. Nat. Vol. 134: 147-155, 1989) as arising from competition for resource allocation between the maternal parent which limits growth of the embryo by favouring equitable distribution of resources among all the seeds, and each embryo whose fitness is increased by garnering of greater resources. According to Haig D, and Westoby M., Am. Nat. Vol. 134: 147-155, 1989 imprinted genes that are maternally expressed in the embryo would act to limit growth of the embryo whereas paternally expressed genes would favour increased growth of the embryo. Thus seeds that contain an extra paternal genome equivalent would be larger than normal due to an excess dosage of gene products that promote growth of the embryo whereas seeds that contain an extra maternal genome equivalent would be smaller than normal due to an excess dosage of gene products that limit growth of the embryo.

To address the maternal and paternal contributions in selfed seeds of the dyad mutant the seeds were analyzed with respect to size. The selfed seeds obtained from dyad mutant plants were heterogenous in size and classified in either of three categories: large, normal, and shrunken as depicted in FIG. 10. The size class distribution from 7 individual dyad mutant plants is shown below:

TABLE 3

Size Class Distribution for seeds from dyad mutant plants:

| Plant No. | N | L | S |
|---|---|---|---|
| 1. | 18 | 7 | 79 |
| 2. | 44 | 26 | 64 |
| 3. | 25 | 25 | 36 |
| 4. | 47 | 21 | 33 |
| 5. | 46 | 5 | 52 |
| 6. | 58 | 16 | 98 |
| 7. | 16 | 6 | 37 |
| Total | 254 | 106 | 399 |

Seeds from each class were sampled from multiple plants, germinated and grown into plants. The ploidy of each plant was determined by chromosomal counts in meiotic spreads. The results are indicated in Table 4 below:

TABLE 4

Ploidy of plants from each seed class in selfed dyad mutants

| Category | Diploids | Triploids | Tetraploids | Others (aneuploids) |
|---|---|---|---|---|
| Shrunken | 2(4) | 41(85) | — | 5(11) |
| Large | 26(72) | 3(8.5) | 3(8.5) | 4(11) |
| Normal | 5(14) | 26(76) | — | 4(10) |

Numbers in brackets indicate percentage of total plants examined in each category These data show that most triploids are shrunken in size and make up the major portion of the shrunken category of seed. The observation that most triploids are shrunken indicates that they arise from an excess maternal contribution (2n) and not from an excess paternal contribution which would therefore be 1n in the triploids. Together with the finding of Example 4 that all triploids retain parental heterozygosity, these results indicate that the retention of heterozygosity is obtained from the female parent, and hence that the triploids arise from an unreduced female gamete that retains parental heterozygosity.

To confirm that triploids in dyad arise from a 2n female contribution, we crossed a dyad mutant as a female to the line ETC60 (wild type for DYAD) as a male to give F1 seed. The ETC60 line (described in U.S. patent application Ser. No. 10/857,539) carries a single copy of a Ds transposon harbouring a kanamycin resistance gene. By following the segregation of kanamycin resistance following further crossing of the F1 to wild type diploid plants, it is possible to determine the ploidy contribution from the male gamete in the F1 plant. Seeds from the first cross were germinated and seedlings were transferred to soil. Six F1 plants were tested for the presence of the kanamycin resistance gene using kanamycin resistance gene-specific primers (KanF SEQ ID NO: 49 and KanR SEQ ID NO: 50) as well as for a copy of the transposon in ETC60 using a transposon specific Ds5-2 primer (SEQ ID NO: 45) in combination with a gene-specific primer GLTF (SEQ ID NO:46). All six plants were positive for the Ds element carrying kanamycin resistance and were also fertile as would be expected for crossed plants containing a wild type copy of DYAD. The ploidy of the six plants was examined using spreads of meiotic chromosomes. It was found that 3 plants were triploid with 15 chromosomes, 2 plants had 16 chromosomes, and 1 had 17 chromosomes. These results suggest the likelihood that female gametes arose from unreduced/hyperdiploid spores. Fertilization of the unreduced female gametes by a haploid pollen would give (near) triploids which be simplex for the kanamycin resistance gene (Kkk). Alternatively the triploids could arise from fertilization of a haploid female gamete by an unreduced male gamete or two reduced male gametes in which case the triploids would be duplex for the kanamycin resistance gene (KKk).

If a simplex condition plant is crossed to a wild type plant that does not carry kanamycin resistance then the segregation ratio for kanamycin resistance to susceptibility in the resulting plants will be 1:1. If however a duplex condition plant is crossed to a wild type plant then the segregation ratio would be expected to be 5:1. Crosses were carried out for two of the triploid plants obtained above to wild type and the seeds obtained were scored for segregation of kanamycin resistance. The results shown in Table 5 indicate 1:1 segregation for kanamycin resistance ruling out polyspermy, and show that the triploids arise from unreduced female gametes.

TABLE 5

Segregation of $Kan^R$ phenotype in crosses

| | Total no. of seeds | $Kan^R$ Seedlings | $Kan^S$ Seedlings | Ungerminated Seeds* | Statistical significance for goodness of fit by $\chi^2$ test |
|---|---|---|---|---|---|
| Plant 1 | 581 | 254 | 236 | 91 | 1:1** $\chi^2$ = 0.660; P > 0.01 NS |
| | | | | | 5:1*** $\chi^2$ = 240.18; P << 0.001 S |
| Plant 2 | 321 | 121 | 132 | 68 | 1:1** $\chi^2$ = 0.578; P > 0.01 NS |
| | | | | | 5:1*** $\chi^2$ = 138.21; P << 0.001 S |

*Since the seeds are result of a cross of a triploid parent to a diploid parent, a few seeds are not expected to germinate due to aneuploidy.
**Test of signficance for goodness of fit for 1:1 ratio is calculated excluding ungerminated seeds
***Test of significance for goodness of fit for 5:1 ratio is calculated by including the ungerminated seeds in the $Kan^R$ category. Theoretically only 50% of the ungerminated seeds should be included in either category (based on the ratio of $Kan^R$ and $Kan^S$ seedlings obtained) but in order to increase the level of significance we have included the entire ungerminated lot into $Kan^R$ category. This rules out that even though we include the entire ungerminated lot in $Kan^R$ category the goodness of fit for 5:1 ratio is not significant and thus strongly support a condition favouring only 1:1 ratio.
S Significant for $\chi^2$ test indicating that it does not follow the given ratio
NS Non significant for $\chi^2$ test indicating that it follows the given ratio

EXAMPLE 8

The DYAD Gene and Coding Sequence from Poplar (*Populus trichocarpa*)

An additional example of a DYAD gene from poplar is found at http://www.ornl.gov/sci/ipgc.

Figure 11:
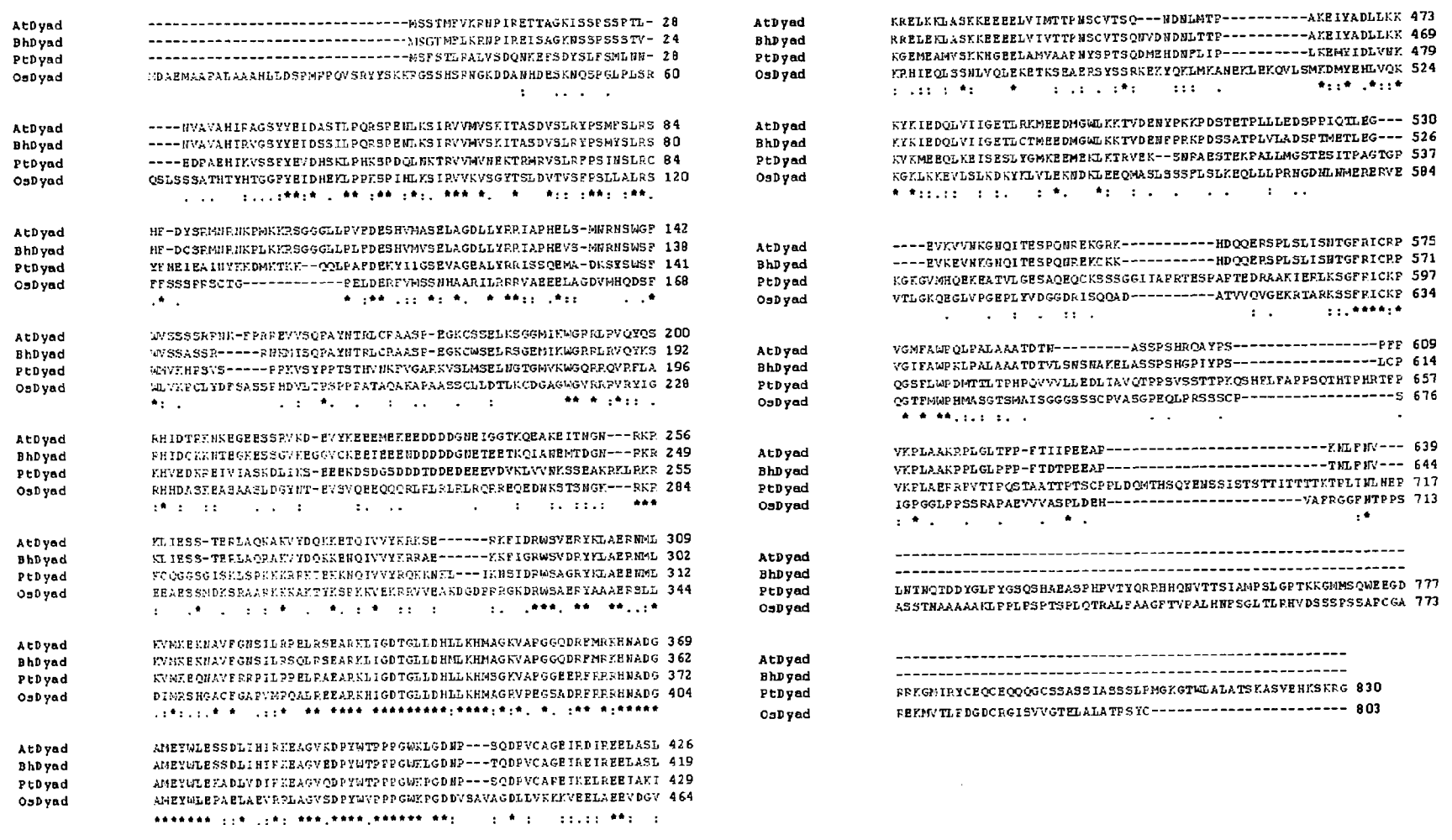

Translation of the coding portion of the cDNA sequence provides an amino acid sequence that is compared to the amino acid sequence of the wild-type DYAD protein from *Arabidopsis thaliana* using the Clustal W program in FIG. 11. AtDyad homologue *Populus trichocarpa* as in http://www.ornl.gov/sci/ipgc Genomic region (SEQ ID NO: 24)

EXON

INTRON

Including 2444 bp upstream of first ATG cattcgttatggctaacggagtcactgggccttacatgcatccacag
accaggtgccggagtgctggtgcaaaaccaatttattgaatttctga
acaattggagacgaaataaatgtctttacttcttcaaacccttgatt
taaaagtaaatgtattatcttttattgattttttattcaattccta
gaattagtagcttgaagaatttattaaatttatcagataaatgagag
ggatatacccttaaaatcgtcaaaaataaatctcaatttacttataa
attgaagaataccttcttaaaaataaaataaaattgcgtgccatccc
tctttagtagattttggcgctactcgtgtggtgtgggtacagagaag
aatattaatatacccgagctggaactagaaggtcaccgccatatcc
aatgaggcaatcccgaacctctcccacaagcaagcatccgccacgtg
gtcagaagctacagaggttatgacctggctaaacgattggctaccag
gaaccaatggctcctcaaaggccatagataaataaatctaagagcca
gtttctttagctctcaactctctcaaccatctatacaacatttccag
aggcaacaagactcgggaggggtaaaacggtaaaatgggagacgtta
ctgtagaggagggagggggggaccagaatccaggtcacgtgaggcgc
atcccgtctggtaataatcattactatttttttctctctttatagca
gaaatgcaccaccatcgttggtttcacaacagaaaaaactccctccc
ccttctctctgcgttttctctcaagctgttttttcttgctctccaaa
caatccatcacaagtagcttttgaaacagaaattgaaaaaaaaggt
ctcgttttatatttattttgctgtttaattttcaacctgattttttt
tcatgtgcattaattaataatgctggtgtagttactctcttggctgg
ttgaatcggtgctggtactggataaaacatctcaaaaggaatgaccc
atttgcatgtcattaagggtgcatgtgtttgaatgaggaattcaaa
caagtcctgacatgagtatgcattttcctgtggttaacagatatagg
ttgtttggctcctggaagattctcaaaattgagatttcaagctcaaa
agtgttttgatacactttccaagcttcatgatctttaatttaccag
tggtgttttcctagttagtgtactttaaaggtcgcataatgatcgg
tagtacttagctttgattttgcattcccgttcgcttcttcttgtttt
cagtctctgcgtaccaacaatatagagattcctggctgtgcaaga
atcactatatctatctatctatctatcaggccttaaccttgcttct tttctgatcaatccttgtgtttatgattgattaatgagattaattgt
atgtttgcttcaaatgattatcttatatatagtctgattttcccttt
ctttaatcatgtccatatatgtttattcgccggggggccgggaagga
cgagaggtacgactagctagtattaacttgtgcagttgaaactgttt
ctctatgtgcagaagatgactaccatggagctggttgatgttgcagt
gatagaccacccatcggtgagtttgttctctcttctcctcaatccca
ctcccactctccactccccaaccaccacacccctttctttctgttac
tcctctatttctcttctcgtaacccacgcgctcttttatctctcaaa
tcaagtcgctgattactagtctactaaagttttcaaatactcaaccg
aattcctaatctttgtctcacgctcacacacataccaaatccacacg
cgcgtccctacaatttgttacgcaaatcaaacccgctctacacat
ccttggtgcccaagtaagtgaaatgatgattttacataacaaaaacc
acataattattatgctatgtaacggtatattctatacattctctatc
gagtattgcacacgaggggcttatgcatacataaatcctcacccctt
ttaaaggagaagggcaatacagtgattttggttgtgcttgtgaaaat
gcaggaaataaaaaggaggcagaactccgaggacgccgatagaaggc
ttttttgggcggacattgcctgcatcacccaacatttaccacagca
ccaccatttggtaatatttgtaacacacacgcacacacgcccgagca
acaaatctctccctctttttttatccctttttgtttcctctctctctct
ctctctctctcacttgatttctctcttctgatttgctgattttttt
actgctcgtactagctagctagctctactcctatagctcacagtact
gcaagtacgtagtactactgcagctgctgctagtgctagtagtagct
<u>ATGTCGTTTTCCACGCTAAGAGCTCTTGTTTCTGATCAAAAT</u>
<u>AAGGAATTCTCTGATTACTCTTTGTTTTCCATGCTTAATAAT</u>
<u>GAAGACCCAGCTGAGCATATTAAAGTGAGCTCTTTTTATGAA</u>
<u>GTTGATCACTCCAAGCTGCCTCATAAATCCCCTGATCAACTC</u>
<u>AACAAAACCCGGGTTGTGATG</u>GTATTTTTTATACAATTCAACAA
TATTCTTAAACCCGGCTCAACATTTTTTTCTCTCTGCTTTAAAATTT
GTTGGTGTTTGTTTCTGCTTGAATAAATATCTCAG<u>GTGAATGAAAA</u>
<u>GACCAGGATGAGAGTCTCGCTGAGGTTTCCAAGCATCAATTC</u>
<u>TCTAAGATGTTACTTCAATGAGATTGAAGCTATTAATTACAA</u>
<u>GAAAGACATGAAAACGAAGAAGCAGCAGCTACCAGCATTCGA</u>
<u>CGAGAAATACATTATAGGATCAGAAGTTGCAGGGGAAGCTCT</u>
<u>TTATAGGAGAATCTCTTCTCAAGAAATGGCAGACAAGAGTTA</u>
<u>CTCATGGAGTTTCTGGATGGTTAAACATCCTTCGGTTTCACC</u>
<u>TCGAAAAGTGTCATACCCACCTACAAGTACTCATGTTAATAA</u>
<u>ATTTGTTGGTGCAAGGAAGGTGTCTCTCATGTCTGAGCTCAA</u>
<u>CGGGACAGGCATGGTTAAGTGGGGTCAGCGCCGGCAGGTCAG</u>
<u>GTTCTTGGCTAAACACGTAGAGGATAAACGTGAAATAGTGAT</u>
<u>TGCATCGAAGGATTTGATTAAAAGCGAAGAAGAGAAAGACAG</u>
<u>TGATGGTAGTGATGATGACACAGACGATGAGGACGAGGAGGA</u>
<u>GGTCGATGTTAAGTTAGTAGTAAACAAGTCAAGTGAAGCTAA</u>
<u>AAGGAAATTACGTAAGAGAAAGTGTCAAGGTGGGTCTGGTAT</u>
<u>TAGCAAATTATCACCAAAAAAGAAAAGGCGTAAAATTGAAAA</u>

GAAGAACCAGATTGTGGTCTATAGGCAAAAGAAGAACAAACT

CATCAAGAATTCTATTGACAGATGGTCTGCGGGGAGGTAATA

AAGCTTTTATTAGTTAATAAACTAAATTCAGATCGTCATTTGTGTT

AATATATTTTTTTGATTAGTGTCTATATGTAGCTAGCTAATTTGGT

TGGGTGATTTCTGTGAAGGTATAAATTGGCTGAGGAAAACATG

TTAAAGGTAATGAAAGAGCAAAATGCTGTGTTTCGACGCCCA

ATTTTAAGGCCAGAATTGAGAGCTGAGGCACGGAAGTTGATT

GGGGATACTGGGCTGTTAGACCACTTGTTGAAGCATATGTC

AGGGAAGGTGGCTCCGGGAGGAAGAGAGATTCAGAAGGAG

GCATAACGCAGATGGAGCAATGGAGTATTGGCTGGAGAAGGC

TGATTTGGTTGATATCAGGAAAGAGGCTGGTGTGCAGGATCC

TTATTGGACACCTCCACCTGGGTGGAAACCTGGTGATAATCC

TAGTCAGGATCCAGTTTGTGCTAGAGAGATCAAGGAACTCAG

AGAAGAAATTGCTAAAATTAAAGGTACTGGTCCTTCTGTTTTA

ACTAGGATTGATTGTCTTTCAATTTTGTGTGGTCTTTTAGCTTGTTA

GTGCTGTTGATCTGGTAATGCCCACCAGTTTTTCTCTGTTACTCTTG

GGGTGAATTGTGTGCGCTACTGATTCCATCTCTCGCGTATGTGTTGT

TCTTATGGGGGCAGGGAGATGGAGGCAATGGTGTCTAAAAAAC

ACGGGGAGGAATTAGCAATGGTGGCAGCACCGAATTATTCTC

CTACAAGTCAGGACATGGAGCATGACAACTTCTTAATTCCAC

TGAAGGTAATAGATATGAAAGTTTGACCAGATTTTTGGACTGACCC

AAGTTCTTCTCTTGACAATCCATGTACTATTTTTGCAGGAAATGTA

CATTGATTTGGTGAATAAGAAGGTAAAGATGGAGGAACAACT

AAAGGAAATTTCAGAATCTTTGTATGGGATGAAGGTAGGAGAG

CATGAGAATTCTTCCTTTAATAATTATCATTTTCTTTTCAATTGAAG

TGTGTAAGATTTGATATGAATGATTCTTTCCACGTTATGACGTTCTG

GGTGCTACTAGTGTATATAAGATTCGTTCAAATAAGAAATTCCTGGG

TGATTGCATGATCCACATCATTGAAAGATGGTAGTAACAAACTGACC

ATCTGATGCATGTATCTATTCTAGATAATAAGTTGATGCATAAATTG

CCATGAAACCATTTGAGAAGCTGTTATATTTAGAGGCTTGATATGGG

AGTGTTGCTTATTCCAGACTAGATTTTGCAATTATTTAGTTCAATT

TAAAGCTCAAAATCCCACATTAAATAGTTTCATAAATGATGAATGTT

CTGGCAGTGGATTTCCGTTGTCCTTGGTAGTACTTTCTAATCTGGAC

AGCATTTATATTGTAACAATGATACGCTTAATGATGATCTTAGGATG

AATTGGTTAGTTATGAATTTAGTTGTCCTTACAGTGCAACGGGGAGG

CTTGGCTGCATTTATTGTTGTAGCATTTAATTATGCATTGAACGCGG

TCATTATTGTGATGATGGAAATATTTAATTGATGCAGGAAGAAATG

GAGAAGCTAAAAACCAGAGTGGAGAAATCAAACAGAGCAGAA

TCAACTGAAAAGCCAGCTTTATTAATGGGCTCAACAGAGTCA

ATCACGCCAGCAGGAACTGGAAGAAAGGGGAAAGGAGTAATG

CATCAGGAAAAAGAAGCAACGGTTTTAGGGGAATCAGCACAA

GAACAATGCAAGTCATCATCAGGAGGCATCATAGCACCAAGA

ACAGAATCACCAGCACCAACGGAGGACAGGGCAGCAAAGATA

GAGAGGCTGAAAAGCGGGTTTAGAATATGCAAGCCCCAGGGA

AGTTTCCTGTGGCCGGATATGACTACCTTAACCCCTCACCC

TCAGGTTGTGGTCCTACTAGAAGACCTCATTGCGGTACAAA

CACCTCCCTCAGTGTCCTCCACTACACCAAAACAATCTCAC

TTCCTCTTTGCTCCTCCATCTCAAACCCATACACCCCACCG

TACTTTCCCTGTGAAGCCATTAGCTGAGAGAAGGCCTGTCA

CCATTCCCCAATCCACAGCTGCCACGACTCCAACCAGCTGT

CCTCCCCTTGATCAAATGACTCACTCCCAGTATGAGAATAG

CAGCATTTCCACTTCTACTACCATCACCACCACTACCAAAA

CCCCTCTCATCAACCTTAATGAGCCACTGAATACCAATCAA

ACTGATGATTATGGATTGTTTTATGGGTCTCAGTCTCATGC

TGAAGCCTCTCCTCACCCTGTCACTTACCAAAGAAGACATC

ATCAAAATGTGACCACCAGTATTGCCATGCCAAGTGTATGTG

TACTTATCAAATCTCAATTTCAATTCATACCCATATTTTAGTGATA

CTATCATAGTATACAAGTTGACTCCTTTTTCATTTTCTGTATGTTT

TACACAGTTGGGACCCACAAAGAAAGGGATGATGAGCCAATG

GGAGGAAGGTGATCGGAGAAAAGGAATGATAAGGTACTGTG

AGCAGTGTGAGCAGCAACAGGGATGCTCCTCTGCCTCTTCC

ATTGCATCTTCTTCCTTGCCAATGGGAAAGGGGACTTGGTT

GGCTCTGGCTACTTCTAAGGCTTCCGTGGAGCACAAATCTA

AAAGGGGTTAAACAATCTATAATAATAATAGTAGTAGTAATAATG

GCTAGTTTATTATGCTAGAGTAGTTATTAGTTAAACCCCTGGAAAA

ACATTGATTAGGTTGGGTTTCACTTAATGCTTTCCCTGTGCTTTGG

GCAAGGAATCTTCTTAACATAGTTATATACATATGGCATATACAAG

GCACAAAGAGCTTTTAGCGTATAGGAAAA

```
Transcript/CDS as in the database (2493 bp)
                    (SEQ ID NO: 25)
``` atgtcgttttccacgctaagagctcttgtttctgatcaaaataaggaatt
ctctgattactctttgttttccatgcttaataatgaagacccagctgagc
atattaaagtgagctcttttttatgaagttgatcactccaagctgcctcat
aaatcccctgatcaactcaacaaaacccgggttgtgatggtgaatgaaaa
gaccaggatgagagtctcgctgaggtttccaagcatcaattctctaagat
gttacttcaatgagattgaagctattaattacaagaaagacatgaaaacg
aagaagcagcagctaccagcattcgacgagaaatacattataggatcaga
agttgcaggggaagctctttataggagagaatctcttctcaagaaatggcag
acaagagttactcatggagtttctggatggttaaacatccttcggtttca
cctcgaaaagtgtcataccccacctacaagtactcatgttaatcaaatttgt
tggtgcaaggaaggtgtctctcatgtctgagctcaacgggacaggcatgg
ttaagtggggtcagcgccggcaggtcaggttcttggctaaacacgtagag
gataaacgtgaaatagtgattgcatcgaaggatttgattaaaagcgaaga
agagaaagacagtgatggtagtgatgatgacacagacgatgaggacgagg
aggaggtcgatgttaagttagtagtaaacaagtcaagtgaagctaaagg
aaattacgtaagagaaagtgtcaaggtgggtctggtattagcaaatttatc
accaaaaagaaaaggcgtaaaattgaaaagaagaaccagattgtggtct
ataggcaaaagaagaacaaactcatcaagaattctattgacagatggtct
gcggggaggtataaattggctgaggaaaacatgttaaaggtaatgaaaga
gcaaaatgctgtgtttcgacgcccaatttttaaggccagaattgagagctg
aggcacggaagttgattggggatactgggctgttagaccacttgttgaag
catatgtcagggaaggtggctccgggaggaagagagattcagaaggag
gcataacgcagatggagcaatggagtattggctggagaaggctgatttgg
ttgatatcaggaaagaggctggtgtgcaggatccttattggacacctcca
cctgggtggaaacctggtgataatcctagtcaggatccagtttgtgctag
agagatcaaggaactcagagaagaaattgctaaaattaaagggagatg
aggcaatggtgtctaaaaaacacggggaggaattagcaatggtggcagca
ccgaattattctcctacaagtcaggacatggagcatgacaacttcttaat
tccactgaaggaaatgtacattgatttggtgaataagaaggtaaagatgg

Transcript/CDS as in the database (2493 bp) (SEQ ID NO: 25)

```
aggaacaactaaaggaaatttcagaatctttgtatgggatgaaggaagaa
atggagaagctaaaaaccagagtggagaaatcaaacagagcagaatcaac
tgaaaagccagctttattaatgggctcaacagagtcaatcacgccagcag
gaactggaagaaaggggaaaggagtaatgcatcaggaaaaagaagcaacg
gttttaggggaatcagcacaagaacaatgcaagtcatcatcaggaggcat
catagcaccaagaacagaatcaccagcaccaacggaggacagggcagaa
agatagagaggctgaaaagcgggtttagaatatgcaagccccagggaagt
ttcctgtggccggatatgactaccttaaccccccaccctcaggttgtggt
cctactagaagacctcattgcggtacaaacacctccctcagtgtcctcca
ctacaccaaaacaatctcacttcctctttgctcctccatctcaaacccat
acaccccaccgtactttccctgtgaagccattagctgagagaaggcctgt
caccattccccaatccacagctgccacgactccaaccagctgtcctcccc
ttgatcaaatgactcactcccagtatgagaatagcagcatttccacttct
actaccatcaccaccactaccaaaaccctctcatcaaccttaatgagcc
actgaataccaatcaaactgattatgattgttttatgggtctcagt
ctcatgctgaagcctctcctcaccctgtcacttaccaaagaagacatcat
caaaatgtgaccaccagtattgccatgccaagtttgggacccacaaagaa
agggatgatgagccaatgggaggaaggtgatcggagaaaaggaatgataa
ggtactgtgagcagtgtgagcagcaagggatgctcctctgcctcttcc
attgcatcttcttccttgccaatgggaaagggacttggttggctctggc
tacttctaaggcttccgtggagcacaaatctaaaaggggttaa
```

Protein Sequence as in database (830aa) (SEQ ID NO: 26)

```
>eugene3.00030791 [Poptr1:554158]
MSFSTLRALVSDQNKEFSDYSLFSMLNNEDPAEHIKVSSFYEVDHSKLPH
KSPDQLNKTRVVMVNEKTRMRVSLRFPSINSLRCYFNEIEAINYKKDMKT
KKQQLPAFDEKYIIGSEVAGEALYRRISSQEMADKSYSWSFWMVKHPSVS
PRKVSYPPTSTHVNKFVGARKVSLMSELNGTGMVKWGQRRQVRFLAKHVE
DKREIVIASKDLIKSEEEKDSDGSDDDTDDEDEEEVDVKLVVNKSSEAKR
KLRKRKCQGGSGISKLSPKKKRRKIEKKNQIVVYRQKKNKLIKNSIDRWS
AGRYKLAEENMLKVMKEQNAVFRRPILRPELRAEARKLIGDTGLLDHLLK
HMSGKVAPGGEERFRRRHNADGAMEYWLEKADLVDIRKEAGVQDPYWTPP
PGWKPGDNPSQDPVCAREIKELREEIAKIKGEMEAMVSKKHGEELAMVAA
PNYSPTSQDMEHDNFLIPLKEMYIDLVNKKVKMEEQLKEISESLYGMKEE
MEKLKTRVEKSNRAESTEKPALLMGSTESITPAGTGRKGRGVMHQEKEAT
VLGESAQEQCKSSSGGIIAPRTESPAPTEDRAAKIERLKSGFRICKPQGS
FLWPDMTTLTPHPQVVVLLEDLIAVQTPPSVSSTTPKQSHFLFAPPSQTH
TPHRTFPVKPLAERRPVTIPQSTAATTPTSCPPLDQMTHSQYENSSISST
STTITTTTKTPLINLNEPLNTNQTDDYGLFYGSQSHAEASPHPVTYQRRH
HQNVTTSIAMPSLGPTKKGMMSQWEEGDRRKGMIRCEQCEQQQGCSSASS
IASSSLPMGKGTWLALATSKASVEHKSKRG*
```

EXAMPLE 9

Identification of Maize DYAD Polynucleotides and Polypeptides

A search of the maize genome using TBLASTN and the rice DYAD protein (SEQ ID NO: 51) as query at the website (www.plantgdb.org) revealed the presence of a putative DYAD gene within a region of the maize genome corresponding to the contigs ZmGSStuc11-12-04.1016.1 (SEQ ID NO:52) and ZmGSStuc11-12-04.1016.2 (SEQ ID NO:53). Annotation of the region using GENSCAN (http://genes.mit.edu) in combination with manual editing led to the identification of putative maize polypeptide sequences that could be aligned with rice DYAD polypeptide sequences (FIG. 12). The present invention encompasses the use of the said maize polypeptide sequences and polynucleotide sequences encoding said polypeptides.

The polypeptide sequences obtained from Z. mays are mapped to the contig nucleotide sequences as shown by nucleotide coordinates below. The assembled partial Zm DYAD polypeptide sequences encoded by the contig sequences are also shown.

ZmGSStuc11-12-04.1016.1 (SEQ ID NO: 52) Coordinates and conceptual translation

| 5335 ESKDGDPR | . . . | GVKRYI | 4882; |
|---|---|---|---|
| 4724 EQLLCK | . . . | DYSSLK | 4662; |
| 4142 EKYQRA | . . . | QVLCLK | 4080; |
| 3805 DMCEN | . . . | EVSSFK | 3743; |
| 3605 EKYEHI | . . . | FLSFK | 3522; |
| 3413 DQLVVAL | . . . | GLTRRDV | 2865: |
| 2697 DTSSS | . . . | LATPSYC | 2563; |

Z. mays assembled polypeptide:

```
                                              (SEQ ID NO:54)
ESKDGDPRHGDDRWSAERYAAAEKSLLNIMRSRDARFGAPVMRQVLREEA
RKHIGDTGLLDHLLKHMAGRVPEGSVHRFRRRHNADGAMEYWLEPAELAE
VRKQAGVSDPYWVPPPGWKPGDDVSLVAGDILVKRQVEELTEEVNGVKRY
IEQLLCKDDGDFGAERDYSSLKEKYQRAVRANEKLEKQVLCLKDMCENVV
QMNGELKKEVSSFKEKYEHIADKNDKLEEQVTYLSSSFLSFKDQLVVALK
LELAPSEAVPRTALFVASGEQMTGTVIQGGQDRAERKSSFRVCKPQGKFL
LPSMASGMTIGRGASSTCPAAATPCGPIGRSTSFPSMPGLPRSSRGPVEV
VAAASGLDEHVMFGAHFSTPPSASSTNDAAKLQLSLPSPRSPLQPQKLFD
TVTAAASGFSPQKLMHFSGLTRRDVDTSSSSSGACGSGLLEGKRVLFDAD
AGGISAVGTELALATPSYC
```

ZmGSStuc11-12-04.1016.2 (SEQ ID NO: 53) Coordinates and conceptual translation

| 774 MSLFIS | | | 757; |
|---|---|---|---|
| 574 KPQVKK | . . . | PTYHA | 418; |
| 315 GAFYEID | . . . | SIRVVK | 237; |
| 144 VSECTN | . . . | SNHAAR | 1; |

Z. mays assembled polypeptide:

```
                                              (SEQ ID NO: 55)
MSLFISKPQVKKYYFKKKTSSSHSRNGKDDVNHDSTIQPRSPLSRQSLTF
DAIPTYHAGAFYEIDHDKLPPKSPIHLKSIRVVKVSECTNLDITVKFPSL
QALRSFFSSYPAPGTGPELDERFVMSSNHAAR
```

EXAMPLE 10

A General Procedure for Parthenogenesis

Determination of optimum irradiation dose:
1. Collect anthers from a male parent plant of the same species or related species as the female parent plant to be used and irradiate with ionizing radiation in a dose range comprising 1, 5, 10, 20, 30, 50, 70, 100, 150, 200 krad.
2. Pollinate emasculated flowers or female flowers from the female plant that differs from the irradiated pollen parent in carrying one or more recessive phenotypic markers or else with respect to DNA markers (microsatellite, CAPS, or RAPD). Preferably use 10-50 flowers for pollination at each dose of ionizing radiation.
3. Collect seeds from pollinated flowers and pool seeds from flowers that were pollinated with pollen that received the same radiation dose.
4. Germinate seeds and grow into plants so as to give about 20-100 plants for each dose of irradiation.
5. Score the genotype of plants with respect to the phenotypic marker or DNA markers and calculate the proportion of plants that resemble the maternal parent.

6. Choose a dosage that gives an optimum combination of both a high percentage of viable plants as well as a high proportion of plants that resemble the maternal parent.

Induction of parthenogenesis in a dyad mutant plant:
1. Pollinate a dyad mutant plant with pollen irradiated using an appropriate dose of ionizing radiation determined as described above.
2. Collect seeds.
3. Germinate seeds and grow into plants.

Identification of parthenogenetic plants:
1. Score plants with respect to a recessive phenotypic marker carried by the female parent. Plants that show the recessive phenotype are classified as parthenogenetic. In addition the plants may be scored for DNA markers by isolating DNA from plant tissue followed by analysis of DNA with respect to polymorphic markers. Plants showing marker patterns that are characteristic of the female parent and are lacking the marker bands for the male parent are classified as parthenogenetic. The percentage of parthenogenetic plants from a pollination experiment may thus be calculated.
2. Parthenogenetic plants can be examined for markers for which the female parent was heterozygous. Those plants that retain heterozygosity for all markers for which the female dyad mutant parent was heterozygous are apomictic plants.

References for possible molecular markers that may be used for different crop species are listed below:

Wheat:
www.gramene.org
1. Torada et al. (2006). SSR-based linkage map with new markers using an intraspecific population of common wheat. Theor Appl Genet. April 2006; 112(6): 1042-51.
2. Song et al. (2005). Development and mapping of microsatellite (SSR) markers in wheat. Theor Appl Genet. February 2005; 110(3):550-60.

Rice:
www.gramene.org
1. Harushima et al. (1998). A high-density rice genetic linkage map with 2275 markers . . . " Genetics 148: 479-494.
2. Causse et al. (1994). Saturated molecular map of the rice genome based on an interspecific backcross population. Genetics. December 1994; 138(4):1251-74.

Maize: Coe et al. (2002). "Access to the maize genome: an integrated physical and genetic map". Plant Physiol. 128: 9-12.
www.gramene.org Barley: www.gramene.org
Wenzl et al. (2006). A high-density consensus map of barley linking DArT markers to SSR, RFLP and STS loci and agricultural traits. BMC Genomics. Aug. 12, 2006; 7(1): 206

Oats: www.gramene.org

De Koeyer et al. (2004). A molecular linkage map with associated QTLs from a hulless x covered spring oat population. Theor Appl Genet. May 2004; 108(7):1285-98.

Pearl millet: www.gramene.org
An integrated genetic map and a new set of simple sequence repeat markers for pearl millet, *Pennisetum glaucum*. Theor Appl Genet. November 2004; 109(7):1485-93.

Sorghum: Chittenden et al. (1994). "A detailed RFLP map of Sorghum bicolor . . . ". Theor. Appl. Genet. 87: 925-933.

*Brassica oleracea*: Bohuon et al. (1998). "Comparison of a Brassica oleracea genetic map with the genome of *Arabidopsis thaliana*". Genetics 150: 393-401.

*Brassica juncea*: Pradhan et al. (2003). A high-density linkage map in *Brassica juncea* (Indian mustard) using AFLP and RFLP markers. Theor Appl Genet. February 2003; 106(4):607-14.

*Brassica napus*: Piquemal et al. (2005). Construction of an oilseed rape (*Brassica napus* L.) genetic map with SSR markers. Theor Appl Genet. November 2005; 111(8):1514-23.

*Brassica rapa*: Kole et al. (1997). Genetic linkage map of a *Brassica rapa* recombinant inbred population. J. Hered. 88:553-557

Cotton: Rong et al. (2004). "A 3347-locus genetic recombination map . . . " Genetics 166: 389-417.

Tomato: Zhang et al. (2002). A molecular linkage map of tomato displaying chromosomal locations of resistance gene analogs based on a *Lycopersicon esculentum×Lycopersicon hirsutum* cross. Genome February 2002; 45(1): 133-46.

Eggplant: Doganlar et al. (2002)A comparative genetic linkage map of eggplant (*Solanum melongena*) and its implications for genome evolution in the solanaceae. Genetics 161(4):1697-711

Capsicum: Genome mapping in capsicum and the evolution of genome structure in the solanaceae. Genetics 152(3): 1183-202.

Potato: Tanksley et al. (1992). High density molecular linkage maps of the tomato and potato genomes. Genetics 132(4): 1141-1160.

Soybean: Ferreira et al. (2000). Soybean genetic map of RAPD markers assigned to an existing scaffold RFLP map. J. Hered. 91(5): 392-396.

*Populus*: Yin et al. (2001). Preliminary interspecific genetic maps of the populus genome constructed from RAPD markers. Genome August 2001; 44(4):602-9.

Tuskan et al. (2004). Characterization of microsatellites revealed by genomic sequencing of *Populus trichocarpa*. Canadian J. Forest Res. 34(1): 85-93.

Various articles of the scientific periodical and patent literature are cited herein. Each such article is hereby incorporated by reference in its entirety and for all purposes by such citation.

---

What is claimed is:

1. An *Arabidopsis, Boechera, Brassica, Raphanus* or *Sinapis* plant each comprising a genome homozygous for a dyad allele and conditionally expressing a DYAD protein in the nucleus of cells of the plant,
   wherein the plant as a female parent produces seeds that retain female parental heterozygosity under conditions when said DYAD protein is not expressed in the nucleus of cells of the plant,
   wherein said DYAD protein has an amino acid sequence at least 90% identical to SEQ ID NO:5.

2. The plant of claim 1, in which said genome comprises at least one copy of a polynucleotide encoding a DYAD protein fused to a steroid hormone receptor ligand binding domain.

3. The plant of claim 2, in which said steroid hormone receptor ligand binding domain is a glucocorticoid receptor ligand binding domain.

4. The plant of claim 1, in which the dyad allele is one in which a DYAD protein, truncated at an amino acid position from 508 to 572 to delete the carboxy-terminal part of the DYAD protein, is expressed.

5. The plant of claim 4, in which the dyad allele comprises a polynucleotide having the nucleotide sequence of SEQ ID NO: 1.

6. The plant of claim 1, in which the conditionally expressed DYAD protein is encoded by a polynucleotide comprising the nucleotide sequence of SEQ ID NO: 4.

7. The plant of claim 5, in which the conditionally expressed DYAD protein is encoded by a polynucleotide comprising the nucleotide sequence of SEQ ID NO: 4.

8. A seed or a tissue of the plant of claim 1, said seed or tissue comprising a construct that confers conditional expression of the DYAD protein in the nucleus.

9. A method for maintaining a plant line homozygous for dyad comprising propagating a plant of claim 1 under conditions sufficient for expression of the DYAD protein.

10. A method for obtaining an *Arabidopsis, Boechera, Brassica, Raphanus* or *Sinapis* plant, each of which is conditional for retention of parental heterozygosity and conditionally expresses a wild-type DYAD protein in the nucleus of cells of said plant, comprising:
   transforming cells of an *Arabidopsis, Boechera, Brassica, Raphanus* or *Sinapis* plant that is homozygous for a dyad allele with a vector comprising a construct that conditionally expresses a wild-type DYAD protein in the nucleus of cells of said plant,
   wherein said wild-type DYAD protein has an amino acid sequence at least 90% identical to SEQ ID NO:5.

11. The plant of claim 1 that is homozygous for a construct providing conditional expression of wild-type DYAD protein in the nucleus of cells of said plant,
   wherein said wild-type DYAD protein has an amino acid sequence at least 90% identical to SEQ ID NO:5.

12. The plant of claim 1, in which said genome comprises at least one copy of a polynucleotide encoding the DYAD protein and said polynucleotide further comprising and being operably linked to an intracellular localization sequence directing the protein to the nucleus, said polynucleotide being operably linked to an inducible promoter.

13. The method of claim 10, in which the construct comprises at least one copy of a polynucleotide encoding the DYAD protein fused to a steroid hormone receptor ligand binding domain.

* * * * *

SEQUENCE LISTING

```
<160> NUMBER OF SEQ ID NOS: 55

<210> SEQ ID NO 1
<211> LENGTH: 1979
<212> TYPE: DNA
<213> ORGANISM: Arabidopsis dyad
<220> FEATURE:
<221> NAME/KEY: CDS
<222> LOCATION: (31)..(1587)

<400> SEQUENCE: 1
```

-continued

```
gaggaacgaa gattatcgag agcaaaaatc atg agt agt acg atg ttc gtg aaa         54
                                 Met Ser Ser Thr Met Phe Val Lys
                                  1               5 cgg aat ccg att aga gaa acc acc gcc ggg aaa atc tct tcg ccg tcg         102
Arg Asn Pro Ile Arg Glu Thr Thr Ala Gly Lys Ile Ser Ser Pro Ser
    10              15                  20 tca ccg act ttg aat gtt gca gtc gcg cat ata aga gct gga tct tat         150
Ser Pro Thr Leu Asn Val Ala Val Ala His Ile Arg Ala Gly Ser Tyr
 25              30                  35                  40 tac gaa atc gat gct tcg att ctt cct cag aga tcg ccg gaa aat ctt         198
Tyr Glu Ile Asp Ala Ser Ile Leu Pro Gln Arg Ser Pro Glu Asn Leu
                45                  50                  55 aaa tcg att aga gtc gtc atg gtg agc aaa atc acg gcg agt gac gtg         246
Lys Ser Ile Arg Val Val Met Val Ser Lys Ile Thr Ala Ser Asp Val
 60              65                  70 tct ctc cgg tac cca agc atg ttt tca ctc cga tcg cat ttc gat tac         294
Ser Leu Arg Tyr Pro Ser Met Phe Ser Leu Arg Ser His Phe Asp Tyr
        75                  80                  85 agt agg atg aac cgg aat aaa ccg atg aag aag agg agt ggt ggt ggt         342
Ser Arg Met Asn Arg Asn Lys Pro Met Lys Lys Arg Ser Gly Gly Gly
     90                  95                 100 ctt ctt cct gtt ttc gac gag agt cat gtg atg gct tcg gag cta gct         390
Leu Leu Pro Val Phe Asp Glu Ser His Val Met Ala Ser Glu Leu Ala
105             110                 115                 120 gga gac ttg ctt tac aga aga atc gca cct cat gaa ctt tct atg aat         438
Gly Asp Leu Leu Tyr Arg Arg Ile Ala Pro His Glu Leu Ser Met Asn
                125                 130                 135 aga aat tcc tgg ggt ttc tgg gtt tct agt tct tct cgc agg aac aaa         486
Arg Asn Ser Trp Gly Phe Trp Val Ser Ser Ser Ser Arg Arg Asn Lys
            140                 145                 150 ttt cca aga agg gag gtg gtt tct caa ccg gcg tac aat act cgt ctc         534
Phe Pro Arg Arg Glu Val Val Ser Gln Pro Ala Tyr Asn Thr Arg Leu
        155                 160                 165 tgt cgc gct gct tca ccg gag gga aag tgc tcg tct gag ctg aaa tcg         582
Cys Arg Ala Ala Ser Pro Glu Gly Lys Cys Ser Ser Glu Leu Lys Ser
170                 175                 180 gga ggg atg atc aag tgg gga agg aga ttg cgt gtg cag tat cag agt         630
Gly Gly Met Ile Lys Trp Gly Arg Arg Leu Arg Val Gln Tyr Gln Ser
185                 190                 195                 200 cgg cat att gat act agg aag aat aag gaa ggt gag gag agt tct aga         678
Arg His Ile Asp Thr Arg Lys Asn Lys Glu Gly Glu Glu Ser Ser Arg
                205                 210                 215 gtg aag gat gaa gtt tac aaa gaa gaa gag atg gag aaa gaa gag gat         726
Val Lys Asp Glu Val Tyr Lys Glu Glu Glu Met Glu Lys Glu Glu Asp
            220                 225                 230 gat gat gat ggg aat gaa ata gga ggc act aaa caa gag gca aag gag         774
Asp Asp Asp Gly Asn Glu Ile Gly Gly Thr Lys Gln Glu Ala Lys Glu
        235                 240                 245 ata act aat gga aat cgt aag aga aag ctg att gaa tca agt act gag         822
Ile Thr Asn Gly Asn Arg Lys Arg Lys Leu Ile Glu Ser Ser Thr Glu
250                 255                 260 aga ctc gct cag aaa gct aag gtt tat gat cag aag aag gaa act caa         870
Arg Leu Ala Gln Lys Ala Lys Val Tyr Asp Gln Lys Lys Glu Thr Gln
265                 270                 275                 280 att gtg gtt tat aag agg aaa tca gag agg aag ttc att gat aga tgg         918
Ile Val Val Tyr Lys Arg Lys Ser Glu Arg Lys Phe Ile Asp Arg Trp
                285                 290                 295 tct gtt gag agg tac aaa cta gct gag agg aac atg tta aaa gtg atg         966
Ser Val Glu Arg Tyr Lys Leu Ala Glu Arg Asn Met Leu Lys Val Met
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 300 |     |     |     | 305 |     |     |     | 310 |     |     |     |     |      |
| aag | gag | aag | aat | gca | gtg | ttt | ggc | aac | tcc | ata | ctc | agg | cca | gag | ttg | 1014 |
| Lys | Glu | Lys | Asn | Ala | Val | Phe | Gly | Asn | Ser | Ile | Leu | Arg | Pro | Glu | Leu |      |
|     |     |     | 315 |     |     |     | 320 |     |     |     | 325 |     |     |     |     |      |
| agg | tca | gaa | gca | agg | aag | ctg | att | ggt | gac | aca | ggt | cta | ttg | gat | cat | 1062 |
| Arg | Ser | Glu | Ala | Arg | Lys | Leu | Ile | Gly | Asp | Thr | Gly | Leu | Leu | Asp | His |      |
|     | 330 |     |     |     |     | 335 |     |     |     |     | 340 |     |     |     |     |      |
| ctg | ctt | aag | cac | atg | gct | ggt | aag | gtg | gct | cct | gga | ggt | caa | gat | agg | 1110 |
| Leu | Leu | Lys | His | Met | Ala | Gly | Lys | Val | Ala | Pro | Gly | Gly | Gln | Asp | Arg |      |
| 345 |     |     |     |     | 350 |     |     |     |     | 355 |     |     |     |     | 360 |      |
| ttt | atg | aga | aag | cac | aat | gca | gat | ggg | gca | atg | gag | tat | tgg | ttg | gag | 1158 |
| Phe | Met | Arg | Lys | His | Asn | Ala | Asp | Gly | Ala | Met | Glu | Tyr | Trp | Leu | Glu |      |
|     |     |     |     | 365 |     |     |     |     | 370 |     |     |     |     | 375 |     |      |
| agt | tct | gat | ttg | att | cac | ata | agg | aaa | gaa | gca | gga | gtt | aaa | gat | cct | 1206 |
| Ser | Ser | Asp | Leu | Ile | His | Ile | Arg | Lys | Glu | Ala | Gly | Val | Lys | Asp | Pro |      |
|     |     |     | 380 |     |     |     |     | 385 |     |     |     |     | 390 |     |     |      |
| tac | tgg | act | cct | cca | cct | ggt | tgg | aag | ctt | ggt | gac | aac | cct | tct | caa | 1254 |
| Tyr | Trp | Thr | Pro | Pro | Pro | Gly | Trp | Lys | Leu | Gly | Asp | Asn | Pro | Ser | Gln |      |
|     |     | 395 |     |     |     |     | 400 |     |     |     |     | 405 |     |     |     |      |
| gat | cct | gtc | tgc | gct | gga | gaa | atc | cgt | gac | atc | aga | gaa | gaa | tta | gct | 1302 |
| Asp | Pro | Val | Cys | Ala | Gly | Glu | Ile | Arg | Asp | Ile | Arg | Glu | Glu | Leu | Ala |      |
| 410 |     |     |     |     | 415 |     |     |     |     | 420 |     |     |     |     |     |      |
| agc | ctg | aaa | aga | gaa | ttg | aag | aaa | ctt | gcg | tca | aag | aag | gaa | gag | gag | 1350 |
| Ser | Leu | Lys | Arg | Glu | Leu | Lys | Lys | Leu | Ala | Ser | Lys | Lys | Glu | Glu | Glu |      |
| 425 |     |     |     | 430 |     |     |     |     | 435 |     |     |     |     | 440 |     |      |
| gag | ctt | gtt | atc | atg | act | acg | cct | aat | tct | tgt | gtt | act | agt | cag | aat | 1398 |
| Glu | Leu | Val | Ile | Met | Thr | Thr | Pro | Asn | Ser | Cys | Val | Thr | Ser | Gln | Asn |      |
|     |     |     |     |     | 445 |     |     |     | 450 |     |     |     |     | 455 |     |      |
| gat | aat | ctg | atg | act | cca | gca | aag | gaa | atc | tac | gct | gat | ctg | ctg | aaa | 1446 |
| Asp | Asn | Leu | Met | Thr | Pro | Ala | Lys | Glu | Ile | Tyr | Ala | Asp | Leu | Leu | Lys |      |
|     |     |     | 460 |     |     |     |     | 465 |     |     |     |     | 470 |     |     |      |
| aag | aaa | tac | aaa | att | gag | gac | cag | cta | gtg | att | att | gga | gaa | acc | ttg | 1494 |
| Lys | Lys | Tyr | Lys | Ile | Glu | Asp | Gln | Leu | Val | Ile | Ile | Gly | Glu | Thr | Leu |      |
|     |     | 475 |     |     |     |     | 480 |     |     |     |     | 485 |     |     |     |      |
| cgt | aaa | atg | gag | gaa | gac | atg | gga | tgg | ctt | aag | aaa | aca | gtg | gac | gag | 1542 |
| Arg | Lys | Met | Glu | Glu | Asp | Met | Gly | Trp | Leu | Lys | Lys | Thr | Val | Asp | Glu |      |
|     | 490 |     |     |     |     | 495 |     |     |     |     | 500 |     |     |     |     |      |
| aac | tat | cct | aaa | aac | cag | act | caa | cag | aga | cac | ctt | tgc | tac | tag |     | 1587 |
| Asn | Tyr | Pro | Lys | Asn | Gln | Thr | Gln | Gln | Arg | His | Leu | Cys | Tyr |     |     |      |
| 505 |     |     |     |     | 510 |     |     |     |     | 515 |     |     |     |     |     |      | aggattcacc accaatacag acactagaag gagaagtgaa ggtggtgaac aagggtaacc     1647 aaatcacaga gtcacctcaa aacagagaaa aaggaaggaa gcatgatcaa caagaaagat     1707 caccactttc actaataagc aacactggtt tcagaatctg caggcctgtg gggatgttcg     1767 catggcccca attgcctgct cttgctgctg ctactgatac taatgcttct tcgccaagtc     1827 acagacaagc ctacccatcc ccttttccag tcaagccact gcagctaag cgtcctcttg     1887 gcttgacgtt tcccttcacc atcatacccg aagaagctcc caagaatctc ttcaacgttt     1947 gaagttgtca ctggaaactg atgcatcaga tc                                  1979

<210> SEQ ID NO 2
<211> LENGTH: 1527
<212> TYPE: DNA
<213> ORGANISM: Arabidopsis

<400> SEQUENCE: 2
atgagtagta cgatgttcgt gaaacggaat ccgattagag aaaccaccgc cgggaaaatc     60
tcttcgccgt cgtcaccgac tttgaatgtt gcagtcgcgc atataagagc tggatcttat    120

```
tacgaaatcg atgcttcgat tcttcctcag agatcgccgg aaaatcttaa atcgattaga    180
gtcgtcatgg tgagcaaaat cacggcgagt gacgtgtctc tccggtaccc aagcatgttt    240
tcactccgat cgcatttcga ttacagtagg atgaaccgga ataaaccgat gaagaagagg    300
agtggtggtg gtcttcttcc tgttttcgac gagagtcatg tgatggcttc ggagctagct    360
ggagacttgc tttacagaag aatcgcacct catgaacttt ctatgaatag aaattcctgg    420
ggtttctggg tttctagttc ttctcgcagg aacaaatttc aagaaggga ggtggtttct    480
caaccggcgt acaatactcg tctctgtcgc gctgcttcac cggagggaaa gtgctcgtct    540
gagctgaaat cggagggat gatcaagtgg ggaaggagat gcgtgtgca gtatcagagt    600
cggcatattg atactaggaa gaataaggaa ggtgaggaga gttctagagt gaaggatgaa    660
gtttacaaag aagaagagat ggagaaagaa gaggatgatg atgatgggaa tgaaatagga    720
ggcactaaac aagaggcaaa ggagataact aatggaaatc gtaagagaaa gctgattgaa    780
tcaagtactg agagactcgc tcagaaagct aaggtttatg atcagaagaa ggaaactcaa    840
attgtggttt ataagaggaa atcagagagg aagttcattg atagatggtc tgttgagagg    900
tacaaactag ctgagaggaa catgttaaaa gtgatgaagg agaagaatgc agtgtttggc    960
aactccatac tcaggccaga gttgaggtca gaagcaagga agctgattgg tgacacaggt   1020
ctattggatc atctgcttaa gcacatggct ggtaaggtgg ctcctggagg tcaagatagg   1080
tttatgagaa agcacaatgc agatggggca atggagtatt ggttggagag ttctgatttg   1140
attcacataa ggaaagaagc aggagttaaa gatccttact ggactcctcc acctggttgg   1200
aagcttggtg acaacccttc tcaagatcct gtctgcgctg gagaaatccg tgacatcaga   1260
gaagaattag ctagcctgaa aagagaattg aagaaacttg cgtcaaagaa ggaagaggag   1320
gagcttgtta tcatgactac gcctaattct tgtgttacta gtcagaatga taatctgatg   1380
actccagcaa aggaaatcta cgctgatctg ctgaaaaaga aatacaaaat tgaggaccag   1440
ctagtgatta ttggagaaac cttgcgtaaa atggaggaag acatgggatg gcttaagaaa   1500
acagtggacg agaactatcc taaataa                                        1527
```

<210> SEQ ID NO 3
<211> LENGTH: 508
<212> TYPE: PRT
<213> ORGANISM: Arabidopsis

<400> SEQUENCE: 3

```
Met Ser Ser Thr Met Phe Val Lys Arg Asn Pro Ile Arg Glu Thr Thr
1               5                   10                  15

Ala Gly Lys Ile Ser Ser Pro Ser Pro Thr Leu Asn Val Ala Val
            20                  25                  30

Ala His Ile Arg Ala Gly Ser Tyr Tyr Glu Ile Asp Ala Ser Ile Leu
        35                  40                  45

Pro Gln Arg Ser Pro Glu Asn Leu Lys Ser Ile Arg Val Val Met Val
    50                  55                  60

Ser Lys Ile Thr Ala Ser Asp Val Ser Leu Arg Tyr Pro Ser Met Phe
65                  70                  75                  80

Ser Leu Arg Ser His Phe Asp Tyr Ser Arg Met Asn Arg Asn Lys Pro
                85                  90                  95

Met Lys Lys Arg Ser Gly Gly Gly Leu Leu Pro Val Phe Asp Glu Ser
            100                 105                 110

His Val Met Ala Ser Glu Leu Ala Gly Asp Leu Leu Tyr Arg Arg Ile
```

```
            115                 120                 125
Ala Pro His Glu Leu Ser Met Asn Arg Asn Ser Trp Gly Phe Trp Val
        130                 135                 140
Ser Ser Ser Ser Arg Arg Asn Lys Phe Pro Arg Arg Glu Val Val Ser
145                 150                 155                 160
Gln Pro Ala Tyr Asn Thr Arg Leu Cys Arg Ala Ala Ser Pro Glu Gly
                165                 170                 175
Lys Cys Ser Ser Glu Leu Lys Ser Gly Gly Met Ile Lys Trp Gly Arg
            180                 185                 190
Arg Leu Arg Val Gln Tyr Gln Ser Arg His Ile Asp Thr Arg Lys Asn
        195                 200                 205
Lys Glu Gly Glu Glu Ser Ser Arg Val Lys Asp Val Tyr Lys Glu
210                 215                 220
Glu Glu Met Glu Lys Glu Asp Asp Asp Gly Asn Glu Ile Gly
225                 230                 235                 240
Gly Thr Lys Gln Glu Ala Lys Glu Ile Thr Asn Gly Asn Arg Lys Arg
                245                 250                 255
Lys Leu Ile Glu Ser Ser Thr Glu Arg Leu Ala Gln Lys Ala Lys Val
            260                 265                 270
Tyr Asp Gln Lys Lys Glu Thr Gln Ile Val Val Tyr Lys Arg Lys Ser
        275                 280                 285
Glu Arg Lys Phe Ile Asp Arg Trp Ser Val Glu Arg Tyr Lys Leu Ala
290                 295                 300
Glu Arg Asn Met Leu Lys Val Met Lys Glu Lys Asn Ala Val Phe Gly
305                 310                 315                 320
Asn Ser Ile Leu Arg Pro Glu Leu Arg Ser Glu Ala Arg Lys Leu Ile
                325                 330                 335
Gly Asp Thr Gly Leu Leu Asp His Leu Leu Lys His Met Ala Gly Lys
            340                 345                 350
Val Ala Pro Gly Gly Gln Asp Arg Phe Met Arg Lys His Asn Ala Asp
        355                 360                 365
Gly Ala Met Glu Tyr Trp Leu Glu Ser Ser Asp Leu Ile His Ile Arg
370                 375                 380
Lys Glu Ala Gly Val Lys Asp Pro Tyr Trp Thr Pro Pro Gly Trp
385                 390                 395                 400
Lys Leu Gly Asp Asn Pro Ser Gln Asp Pro Val Cys Ala Gly Glu Ile
                405                 410                 415
Arg Asp Ile Arg Glu Glu Leu Ala Ser Leu Lys Arg Glu Leu Lys Lys
            420                 425                 430
Leu Ala Ser Lys Lys Glu Glu Glu Leu Val Ile Met Thr Thr Pro
        435                 440                 445
Asn Ser Cys Val Thr Ser Gln Asn Asp Asn Leu Met Thr Pro Ala Lys
                450                 455                 460
Glu Ile Tyr Ala Asp Leu Leu Lys Lys Tyr Lys Ile Glu Asp Gln
465                 470                 475                 480
Leu Val Ile Ile Gly Glu Thr Leu Arg Lys Met Glu Glu Asp Met Gly
                485                 490                 495
Trp Leu Lys Lys Thr Val Asp Glu Asn Tyr Pro Lys
            500                 505

<210> SEQ ID NO 4
<211> LENGTH: 1920
<212> TYPE: DNA
<213> ORGANISM: Arabidopsis
```

<400> SEQUENCE: 4

```
atgagtagta cgatgttcgt gaaacggaat ccgattagag aaaccaccgc cgggaaaatc    60
tcttcgccgt cgtcaccgac tttgaatgtt gcagtcgcgc atataagagc tggatcttat   120
tacgaaatcg atgcttcgat tcttcctcag agatcgccgg aaaatcttaa atcgattaga   180
gtcgtcatgg tgagcaaaat cacggcgagt gacgtgtctc tccggtaccc aagcatgttt   240
tcactccgat cgcatttcga ttacagtagg atgaaccgga ataaaccgat gaagaagagg   300
agtggtggtg gtcttcttcc tgttttcgac gagagtcatg tgatggcttc ggagctagct   360
ggagacttgc tttacagaag aatcgcacct catgaacttt ctatgaatag aaattcctgg   420
ggtttctggg tttctagttc ttctcgcagg aacaaatttc caagaaggga ggtggtttct   480
caaccggcgt acaatactcg tctctgtcgc gctgcttcac cggagggaaa gtgctcgtct   540
gagctgaaat cgggagggat gatcaagtgg ggaaggagat tgcgtgtgca gtatcagagt   600
cggcatattg atactaggaa gaataaggaa ggtgaggaga gttctagagt gaaggatgaa   660
gtttacaaag aagaagagat ggagaaagaa gaggatgatg atgatgggaa tgaaatagga   720
ggcactaaac aagaggcaaa ggagataact aatggaaatc gtaagagaaa gctgattgaa   780
tcaagtactg agagactcgc tcagaaagct aaggtttatg atcagaagaa ggaaactcaa   840
attgtggttt ataagaggaa atcagagagg aagttcattg atagatggtc tgttgagagg   900
tacaaactag ctgagaggaa catgttaaaa gtgatgaagg agaagaatgc agtgtttggc   960
aactccatac tcaggccaga gttgaggtca aagcaagga agctgattgg tgacacaggt  1020
ctattggatc atctgcttaa gcacatggct ggtaaggtgg ctcctggagg tcaagatagg  1080
tttatgagaa agcacaatgc agatgggggca atggagtatt ggttggagag ttctgatttg  1140
attcacataa ggaaagaagc aggagttaaa gatccttact ggactcctcc acctggttgg  1200
aagcttggtg acaacccttc tcaagatcct gtctgcgctg agaaatccg tgacatcaga  1260
gaagaattag ctagcctgaa aagagaattg aagaaacttg cgtcaaagaa ggaagaggag  1320
gagcttgtta tcatgactac gcctaattct tgtgttacta gtcagaatga taatctgatg  1380
actccagcaa aggaaatcta cgctgatctg ctgaaaaaga aatacaaaat tgaggaccag  1440
ctagtgatta ttggagaaac cttgcgtaaa atggaggaag acatgggatg gcttaagaaa  1500
acagtggacg agaactatcc taaaaagcca gactcaacag agacacctt gctactagag  1560
gattcaccac caatacagac actagaagga gaagtgaagg tggtgaacaa gggtaaccaa  1620
atcacagagt cacctcaaaa cagagaaaaa ggaaggaagc atgatcaaca agaaagatca  1680
ccactttcac taataagcaa cactggtttc agaatctgca ggcctgtggg gatgttcgca  1740
tggcccaat tgcctgctct tgctgctgct actgatacta atgcttcttc gccaagtcac  1800
agacaagcct acccatcccc ttttccagtc aagccacttg cagctaagcg tcctcttggc  1860
ttgacgtttc ccttcaccat cataccgaa gaagctccca gaatctctt caacgtttga  1920
```

<210> SEQ ID NO 5
<211> LENGTH: 639
<212> TYPE: PRT
<213> ORGANISM: Arabidopsis

<400> SEQUENCE: 5

```
Met Ser Ser Thr Met Phe Val Lys Arg Asn Pro Ile Arg Glu Thr Thr
1               5                   10                  15

Ala Gly Lys Ile Ser Ser Pro Ser Ser Pro Thr Leu Asn Val Ala Val
```

-continued

```
                20                  25                  30
Ala His Ile Arg Ala Gly Ser Tyr Tyr Glu Ile Asp Ala Ser Ile Leu
            35                  40                  45
Pro Gln Arg Ser Pro Glu Asn Leu Lys Ser Ile Arg Val Val Met Val
        50                  55                  60
Ser Lys Ile Thr Ala Ser Asp Val Ser Leu Arg Tyr Pro Ser Met Phe
65                  70                  75                  80
Ser Leu Arg Ser His Phe Asp Tyr Ser Arg Met Asn Arg Asn Lys Pro
                85                  90                  95
Met Lys Lys Arg Ser Gly Gly Leu Leu Pro Val Phe Asp Glu Ser
            100                 105                 110
His Val Met Ala Ser Glu Leu Ala Gly Asp Leu Leu Tyr Arg Arg Ile
        115                 120                 125
Ala Pro His Glu Leu Ser Met Asn Arg Asn Ser Trp Gly Phe Trp Val
    130                 135                 140
Ser Ser Ser Ser Arg Arg Asn Lys Phe Pro Arg Arg Glu Val Val Ser
145                 150                 155                 160
Gln Pro Ala Tyr Asn Thr Arg Leu Cys Arg Ala Ala Ser Pro Glu Gly
                165                 170                 175
Lys Cys Ser Ser Glu Leu Lys Ser Gly Met Ile Lys Trp Gly Arg
            180                 185                 190
Arg Leu Arg Val Gln Tyr Gln Ser Arg His Ile Asp Thr Arg Lys Asn
        195                 200                 205
Lys Glu Gly Glu Glu Ser Ser Arg Val Lys Asp Glu Val Tyr Lys Glu
    210                 215                 220
Glu Glu Met Glu Lys Glu Asp Asp Asp Gly Asn Glu Ile Gly
225                 230                 235                 240
Gly Thr Lys Gln Glu Ala Lys Glu Ile Thr Asn Gly Asn Arg Lys Arg
                245                 250                 255
Lys Leu Ile Glu Ser Ser Thr Glu Arg Leu Ala Gln Lys Ala Lys Val
            260                 265                 270
Tyr Asp Gln Lys Lys Glu Thr Gln Ile Val Val Tyr Lys Arg Lys Ser
        275                 280                 285
Glu Arg Lys Phe Ile Asp Arg Trp Ser Val Glu Arg Tyr Lys Leu Ala
    290                 295                 300
Glu Arg Asn Met Leu Lys Val Met Lys Glu Lys Asn Ala Val Phe Gly
305                 310                 315                 320
Asn Ser Ile Leu Arg Pro Glu Leu Arg Ser Glu Ala Arg Lys Leu Ile
                325                 330                 335
Gly Asp Thr Gly Leu Leu Asp His Leu Leu Lys His Met Ala Gly Lys
            340                 345                 350
Val Ala Pro Gly Gly Gln Asp Arg Phe Met Arg Lys His Asn Ala Asp
        355                 360                 365
Gly Ala Met Glu Tyr Trp Leu Glu Ser Ser Asp Leu Ile His Ile Arg
    370                 375                 380
Lys Glu Ala Gly Val Lys Asp Pro Tyr Trp Thr Pro Pro Gly Trp
385                 390                 395                 400
Lys Leu Gly Asp Asn Pro Ser Gln Asp Pro Val Cys Ala Gly Glu Ile
                405                 410                 415
Arg Asp Ile Arg Glu Glu Leu Ala Ser Leu Lys Arg Glu Leu Lys Lys
            420                 425                 430
Leu Ala Ser Lys Lys Glu Glu Glu Leu Val Ile Met Thr Thr Pro
        435                 440                 445
```

```
Asn Ser Cys Val Thr Ser Gln Asn Asp Asn Leu Met Thr Pro Ala Lys
    450                 455                 460

Glu Ile Tyr Ala Asp Leu Leu Lys Lys Lys Tyr Lys Ile Glu Asp Gln
465                 470                 475                 480

Leu Val Ile Ile Gly Glu Thr Leu Arg Lys Met Glu Glu Asp Met Gly
                485                 490                 495

Trp Leu Lys Lys Thr Val Asp Glu Asn Tyr Pro Lys Lys Pro Asp Ser
                500                 505                 510

Thr Glu Thr Pro Leu Leu Leu Glu Asp Ser Pro Pro Ile Gln Thr Leu
            515                 520                 525

Glu Gly Glu Val Lys Val Val Asn Lys Gly Asn Gln Ile Thr Glu Ser
            530                 535                 540

Pro Gln Asn Arg Glu Lys Gly Arg Lys His Asp Gln Gln Glu Arg Ser
545                 550                 555                 560

Pro Leu Ser Leu Ile Ser Asn Thr Gly Phe Arg Ile Cys Arg Pro Val
                565                 570                 575

Gly Met Phe Ala Trp Pro Gln Leu Pro Ala Leu Ala Ala Ala Thr Asp
                580                 585                 590

Thr Asn Ala Ser Ser Pro Ser His Arg Gln Ala Tyr Pro Ser Pro Phe
            595                 600                 605

Pro Val Lys Pro Leu Ala Ala Lys Arg Pro Leu Gly Leu Thr Phe Pro
            610                 615                 620

Phe Thr Ile Ile Pro Glu Glu Ala Pro Lys Asn Leu Phe Asn Val
625                 630                 635

<210> SEQ ID NO 6
<211> LENGTH: 22
<212> TYPE: DNA
<213> ORGANISM: Artificial Sequence
<220> FEATURE:
<223> OTHER INFORMATION: nga162F primer used for microsatellite marker
      analysis

<400> SEQUENCE: 6
ctctgtcact cttttcctct gg                                             22

<210> SEQ ID NO 7
<211> LENGTH: 20
<212> TYPE: DNA
<213> ORGANISM: Artificial Sequence
<220> FEATURE:
<223> OTHER INFORMATION: nga162R primer used for microsatellite marker
      analysis

<400> SEQUENCE: 7
catgcaattt gcatctgagg                                                20

<210> SEQ ID NO 8
<211> LENGTH: 22
<212> TYPE: DNA
<213> ORGANISM: Artificial Sequence
<220> FEATURE:
<223> OTHER INFORMATION: nga225F primer used for microsatellite marker
      analysis

<400> SEQUENCE: 8
tctccccact agttttgtgt cc                                             22

<210> SEQ ID NO 9
<211> LENGTH: 21
```

```
<212> TYPE: DNA
<213> ORGANISM: Artificial Sequence
<220> FEATURE:
<223> OTHER INFORMATION: nga225R primer used for microsatellite marker
      analysis

<400> SEQUENCE: 9
gaaatccaaa tcccagagag g                                              21

<210> SEQ ID NO 10
<211> LENGTH: 22
<212> TYPE: DNA
<213> ORGANISM: Artificial Sequence
<220> FEATURE:
<223> OTHER INFORMATION: nga168F primer used for microsatellite marker
      analysis

<400> SEQUENCE: 10
gaggacatgt ataggagcct cg                                             22

<210> SEQ ID NO 11
<211> LENGTH: 18
<212> TYPE: DNA
<213> ORGANISM: Artificial Sequence
<220> FEATURE:
<223> OTHER INFORMATION: nga168R primer used for microsatellite marker
      analysis

<400> SEQUENCE: 11
tcgtctactg cactgccg                                                  18

<210> SEQ ID NO 12
<211> LENGTH: 21
<212> TYPE: DNA
<213> ORGANISM: Artificial Sequence
<220> FEATURE:
<223> OTHER INFORMATION: nga1107F primer used for microsatellite marker
      analysis

<400> SEQUENCE: 12
cgacgaatcg acagaattag g                                              21

<210> SEQ ID NO 13
<211> LENGTH: 21
<212> TYPE: DNA
<213> ORGANISM: Artificial Sequence
<220> FEATURE:
<223> OTHER INFORMATION: nga1107R primer used for microsatellite marker
      analysis

<400> SEQUENCE: 13
gcgaaaaaac aaaaaaatcc a                                              21

<210> SEQ ID NO 14
<211> LENGTH: 21
<212> TYPE: DNA
<213> ORGANISM: Artificial Sequence
<220> FEATURE:
<223> OTHER INFORMATION: nga6F primer used for microsatellite marker
      analysis

<400> SEQUENCE: 14
atggagaagc ttacactgat c                                              21

<210> SEQ ID NO 15
<211> LENGTH: 21
<212> TYPE: DNA
```

```
<213> ORGANISM: Artificial Sequence
<220> FEATURE:
<223> OTHER INFORMATION: nga6R primer used for microsatellite marker
      analysis

<400> SEQUENCE: 15
tggatttctt cctctcttca c                                              21

<210> SEQ ID NO 16
<211> LENGTH: 3001
<212> TYPE: DNA
<213> ORGANISM: Boechera holboelli

<400> SEQUENCE: 16
gatctgatgc atcagtttca ggtgacagct tcaaacgttg aagagatttg ttggagcttc     60
ttcgggagtg tcggtgaaag gaaacggcaa gccgagaggg ggcttagctg caagtggctt    120
gactggacaa agagatgggt aaattggtcc gtgacttggc gaagaagcaa gttctttagc    180
attactgttt gacaacacag tatcagtagc agcagcaaga gcaggcaatt tgggccatgc    240
gaaaatcccc acaggcctgc agattctgaa accagtgttg cttataagtg aaagtggtga    300
tcgttcttgt tgatcatgct tcttgcattt ttctctgttt tgaggtgact ctgtgatttg    360
gtttcccttg ttcacctcct tcacttctcc ttctagtgtc tccattgttg gcgaatccgc    420
tagtaccaaa ggtgtcgctg atgagtctgg ctttcgagga aagttctcgt ccactgtttt    480
cttaagccat cccatgtctt cctgcaatat ttgcattcat aaaaacacaa atgtttcatc    540
attcattacc agcaaagtgg catctaatag agacagtgga aatgtttgat cacacacgct    600
aaatggaccc atttcacatg gcattcagtg cgtttctcca agggagtttc ctagtgacta    660
cttgatagtt actaaatcat agcaaattta gaagatttta catttaagt aatggttcag     720 ctagaactag taaggagagt gtcagtgttt agaaactcag tctgggattt atatacctcc    780
attgtacaca aggtttctcc aattatcact agctggtcct caattttgta tttcttcttt    840
agcagatcag cgtagatttc ctgagatgaa gtagcagaga tgttcaaaac gtaccataaa    900
ccagtatcac aagatagaga gatctgttac tgtttcaagc tcttaccttt gctggagtcg    960
tcaaattatc attgtccacg ttctgactag taacacaaga atttggtgta gtcacgataa   1020
caagctcctc ctcttccttc tttgacgcca gtttctccaa ttctcttctc aagaccaaga   1080
caaacatgaa ttcaaaaatt gctataagta acaaaagaga tgatcatata accaattcaa   1140
taagttaatt cttctacctt ttcaggctag ctaattcttc tctgatctca cggatttctc   1200
cggcgcagac aggatcttga gtagggttgt caccaagctt ccaaccaggt ggaggcgtcc   1260
agtaaggatc ttcaactcct gcttctttcc ttatgtgaat caaatcagaa ctctccaacc   1320
aatactccat tgccccatct gcattgtgct ttctcataaa cctatcttga cctccaggag   1380
ccaccttacc tgccatgtgc ttaagcatat gatctaaaag accagtgtca ccgatcagct   1440
tccttgcttc tgaccttaac tgtgacctga gtatggagtt gccaaacact gcatttttct   1500
ccttcatcac ttttaacatg ttcctctcag ctagtttgta ccttcaaatt ccaaaattaa   1560
ccacaatcaa tcagatgaac caagacaaat ccaattcag agatcatcaa attcgttaaa    1620
tattcacttt acctatcaac agaccatctg ccaatgaatt tcttctctgc tcttctctta   1680
tagaccacga tttgatttc cttcttctga tcataaacct tagccctctg agcgagtctc    1740
tcagtactgg attcaatcag cttttctctta cgatttccat cagtcatctc gtttgcaatc   1800
tgtttagtct cttctgtttc attcccatca tcatcatcat cattttcttc ctcaatctct   1860
```

```
tctttgcaaa ccccctccctc cttcactcca gaactctcct taccttccgt attcttctta    1920
caatcaatat gccgactctt gtactgcaca cgcaatctcc tcccccactt aatcatttct    1980
ccagatctca gctcagacca acattttccc tccggtgaag ccgcgcgaca gagcctagta    2040
ttgtacgccg gttgagaaat catcttgttc ctgcgagaag aagcagaaga aacccagaaa    2100
ctccacgaat ttctgttcat agaaacttca tgaggtgcga ttcttctgta aagcaaatct    2160
ccagctagct ccgaaaccat cacatggctc tcgtcaaaaa gaggaagaag accaccacca    2220
ctcctcttct tcaaaggttt attccggttc atcctgctgc aatcgaaatg cgatcggagt    2280
gagtacatgc ttgggtatcg gagagacacg tcgctcgccg tgattttgct cacctgcaac    2340
aacaaccaaa aaacgccaa atcactcga aacccagac gaacaacaaa aatgcagatc       2400
cgtctctaat ggtgaaacaa aaagcagaga atccattaaa taccatgacg actctaatcg    2460
atttaaggtt ctccggcgat cttttgaggaa gaatcgaaga atcgatttcg taatacgatc   2520
caactcttat atgcgcgact gcaactggaa gaacaaaacc aaagaaaaaa aaactggaat    2580
tagaagaaaa gcgagaaaat caacaaaaac ggggaaacta tagcttcagt gttttaccat    2640
tcacagtcga tgacgatggc gaagaatttt ttccggcaga gatttctcta atcggattcc    2700
gtttcaggaa catcgttccc tgtagaagaa gaagaagtat ataactcaga gaggttcact    2760
atttttttat ttttgtgttg aatcaaaaat ggaaactgtt aaggaccgga gaatatattt    2820
gaaaaaagct gactctgcga gtataacaag aaaacacacg cgctctctgg tacgcgcgtg    2880
ggagacacaa aggcaacaga atcaagcggt gatgattttt attttctacc gtcatgagag    2940
tgttagagac tgagctatta cagagagaga gagagagatc ttacgctcat gattttgct    3000
c                                                                    3001
```

<210> SEQ ID NO 17
<211> LENGTH: 1947
<212> TYPE: DNA
<213> ORGANISM: Boechera holboelli

<400> SEQUENCE: 17

```
atgagcggaa cgatgttcct gaaacggaat ccgattagag aaatctctgc cggaaaaaat     60
tcttcgccat cgtcatcgac tgtgaatgtt gcagtcgcgc atataagagt tggatcgtat    120
tacgaaatcg attcttcgat tcttcctcaa agatcgccgg agaaccttaa atcgattaga    180
gtcgtcatgg tgagcaaaat cacggcgagc gacgtgtctc tccgataccc aagcatgtac    240
tcactccgat cgcatttcga ttgcagcagg atgaaccgga ataaaccttt gaagaagagg    300
agtggtggtg gtcttcttcc tcttttgac gagagccatg tgatggtttc ggagctagct    360
ggagatttgc tttacagaag aatcgcacct catgaagttt ctatgaacag aaattcgtgg    420
agtttctggg tttcttctgc ttcttctcgc aggaacaaga tgatttctca accggcgtac    480
aatactaggc tctgtcgcgc ggcttcaccg gagggaaaat gttggtctga gctgagatct    540
ggagaaatga ttaagtgggg gaggagattg cgtgtgcagt acaagagtcg gcatattgat    600
tgtaagaaga atacggaagg taaggagagt tctggagtga aggagggagg ggtttgcaaa    660
gaagagattg aggaagaaaa tgatgatgat gatgatggga atgaaacaga agagactaaa    720
cagattgcaa acgagatgac tgatggaaat cgtaagagaa agctgattga atccagtact    780
gagagactcg ctcagagggc taaggttat gatcagaaga aggaaaatca aatcgtggtc    840
tataagagaa gagcagagaa gaaattcatt ggcagatggt ctgttgatag gtacaaacta    900
gctgagagga acatgttaaa agtgatgaag gagaaaaatg cagtgtttgg caactccata    960
```

-continued

```
ctcaggtcac agttaaggtc agaagcaagg aagctgatcg gtgacactgg tcttttagat    1020
catatgctta agcacatggc aggtaaggtg gctcctggag gtcaagatag gtttatgaga    1080
aagcacaatg cagatgggggc aatggagtat tggttggaga gttctgattt gattcacata    1140
aggaaagaag caggagttga agatccttac tggacgcctc cacctggttg aagcttggt     1200 gacaacccta ctcaagatcc tgtctgcgcc ggagaaatcc gtgagatcag agaagaatta    1260
gctagcctga aagagaatt ggagaaactg gcgtcaaaga aggaagagga ggagcttgtt     1320
atcgtgacta caccaaattc ttgtgttact agtcagaacg tggacaatga taatttgacg    1380
actccagcaa aggaaatcta cgctgatctg ctaaagaaga aatacaaaat tgaggaccag    1440
ctagtgataa ttggagaaac cttgtgtaca atggaggaag acatgggatg gcttaagaaa    1500
acagtggacg agaactttcc tcgaaagcca gactcatcag cgacaccttt ggtactagcg    1560
gattcgccaa caatggagac actagaagga gaagtgaagg aggtgaacaa gggaaaccaa    1620
atcacagagt cacctcaaaa cagagaaaaa tgcaagaagc atgatcaaca agaacgatca    1680
ccactttcac ttataagcaa cactggtttc agaatctgca ggcctgtggg gattttcgca    1740
tggcccaaat tgcctgctct tgctgctgct actgatactg tgttgtcaaa cagtaatgct    1800
aaagaacttg cttcttcgcc aagtcacgga ccaatttacc catctctttg tccagtcaag    1860
ccacttgcag ctaagccccc tctcggcttg ccgtttcctt tcaccgacac tcccgaagaa    1920
gctccaacaa atctcttcaa cgtttga                                        1947

<210> SEQ ID NO 18
<211> LENGTH: 648
<212> TYPE: PRT
<213> ORGANISM: Boechera holboelli

<400> SEQUENCE: 18

Met Ser Gly Thr Met Phe Leu Lys Arg Asn Pro Ile Arg Glu Ile Ser
1               5                   10                  15

Ala Gly Lys Asn Ser Ser Pro Ser Ser Thr Val Asn Val Ala Val
            20                  25                  30

Ala His Ile Arg Val Gly Ser Tyr Tyr Glu Ile Asp Ser Ser Ile Leu
        35                  40                  45

Pro Gln Arg Ser Pro Glu Asn Leu Lys Ser Ile Arg Val Val Met Val
    50                  55                  60

Ser Lys Ile Thr Ala Ser Asp Val Ser Leu Arg Tyr Pro Ser Met Tyr
65                  70                  75                  80

Ser Leu Arg Ser His Phe Asp Cys Ser Arg Met Asn Arg Asn Lys Pro
                85                  90                  95

Leu Lys Lys Arg Ser Gly Gly Gly Leu Leu Pro Leu Phe Asp Glu Ser
            100                 105                 110

His Val Met Val Ser Glu Leu Ala Gly Asp Leu Leu Tyr Arg Arg Ile
        115                 120                 125

Ala Pro His Glu Val Ser Met Asn Arg Asn Ser Trp Ser Phe Trp Val
    130                 135                 140

Ser Ser Ala Ser Ser Arg Arg Asn Lys Met Ile Ser Gln Pro Ala Tyr
145                 150                 155                 160

Asn Thr Arg Leu Cys Arg Ala Ala Ser Pro Glu Gly Lys Cys Trp Ser
                165                 170                 175

Glu Leu Arg Ser Gly Glu Met Ile Lys Trp Gly Arg Arg Leu Arg Val
            180                 185                 190
```

```
Gln Tyr Lys Ser Arg His Ile Asp Cys Lys Lys Asn Thr Glu Gly Lys
            195                 200                 205

Glu Ser Ser Gly Val Lys Glu Gly Val Cys Lys Glu Glu Ile Glu
210                 215                 220

Glu Glu Asn Asp Asp Asp Asp Gly Asn Glu Thr Glu Glu Thr Lys
225                 230                 235                 240

Gln Ile Ala Asn Glu Met Thr Asp Gly Asn Arg Lys Arg Lys Leu Ile
                245                 250                 255

Glu Ser Ser Thr Glu Arg Leu Ala Gln Arg Ala Lys Val Tyr Asp Gln
            260                 265                 270

Lys Lys Glu Asn Gln Ile Val Val Tyr Lys Arg Ala Glu Lys Lys
275                 280                 285

Phe Ile Gly Arg Trp Ser Val Asp Arg Tyr Lys Leu Ala Glu Arg Asn
290                 295                 300

Met Leu Lys Val Met Lys Glu Lys Asn Ala Val Phe Gly Asn Ser Ile
305                 310                 315                 320

Leu Arg Ser Gln Leu Arg Ser Glu Ala Arg Lys Leu Ile Gly Asp Thr
            325                 330                 335

Gly Leu Leu Asp His Met Leu Lys His Met Ala Gly Lys Val Ala Pro
            340                 345                 350

Gly Gly Gln Asp Arg Phe Met Arg Lys His Asn Ala Asp Gly Ala Met
            355                 360                 365

Glu Tyr Trp Leu Glu Ser Ser Asp Leu Ile His Ile Arg Lys Glu Ala
370                 375                 380

Gly Val Glu Asp Pro Tyr Trp Thr Pro Pro Gly Trp Lys Leu Gly
385                 390                 395                 400

Asp Asn Pro Thr Gln Asp Pro Val Cys Ala Gly Glu Ile Arg Glu Ile
                405                 410                 415

Arg Glu Glu Leu Ala Ser Leu Arg Arg Glu Leu Glu Lys Leu Ala Ser
            420                 425                 430

Lys Lys Glu Glu Glu Leu Val Ile Val Thr Thr Pro Asn Ser Cys
435                 440                 445

Val Thr Ser Gln Asn Val Asp Asn Asp Asn Leu Thr Thr Pro Ala Lys
450                 455                 460

Glu Ile Tyr Ala Asp Leu Leu Lys Lys Lys Tyr Lys Ile Glu Asp Gln
465                 470                 475                 480

Leu Val Ile Ile Gly Glu Thr Leu Cys Thr Met Glu Glu Asp Met Gly
                485                 490                 495

Trp Leu Lys Lys Thr Val Asp Glu Asn Phe Pro Arg Lys Pro Asp Ser
            500                 505                 510

Ser Ala Thr Pro Leu Val Leu Ala Asp Ser Pro Thr Met Glu Thr Leu
515                 520                 525

Glu Gly Glu Val Lys Glu Val Asn Lys Gly Asn Gln Ile Thr Glu Ser
530                 535                 540

Pro Gln Asn Arg Glu Lys Cys Lys Lys His Asp Gln Gln Glu Arg Ser
545                 550                 555                 560

Pro Leu Ser Leu Ile Ser Asn Thr Gly Phe Arg Ile Cys Arg Pro Val
                565                 570                 575

Gly Ile Phe Ala Trp Pro Lys Leu Pro Ala Leu Ala Ala Thr Asp
            580                 585                 590

Thr Val Leu Ser Asn Ser Asn Ala Lys Glu Leu Ala Ser Ser Pro Ser
            595                 600                 605

His Gly Pro Ile Tyr Pro Ser Leu Cys Pro Val Lys Pro Leu Ala Ala
```

```
                610             615             620
Lys Pro Pro Leu Gly Leu Pro Phe Pro Phe Thr Asp Thr Pro Glu Glu
625             630             635             640

Ala Pro Thr Asn Leu Phe Asn Val
                645

<210> SEQ ID NO 19
<211> LENGTH: 508
<212> TYPE: PRT
<213> ORGANISM: Boechera holboelli

<400> SEQUENCE: 19

Met Ser Gly Thr Met Phe Leu Lys Arg Asn Pro Ile Arg Glu Ile Ser
1               5                   10                  15

Ala Gly Lys Asn Ser Ser Pro Ser Ser Ser Thr Val Asn Val Ala Val
            20                  25                  30

Ala His Ile Arg Val Gly Ser Tyr Tyr Glu Ile Asp Ser Ser Ile Leu
        35                  40                  45

Pro Gln Arg Ser Pro Glu Asn Leu Lys Ser Ile Arg Val Val Met Val
    50                  55                  60

Ser Lys Ile Thr Ala Ser Asp Val Ser Leu Arg Tyr Pro Ser Met Tyr
65                  70                  75                  80

Ser Leu Arg Ser His Phe Asp Cys Ser Arg Met Asn Arg Asn Lys Pro
                85                  90                  95

Leu Lys Lys Arg Ser Gly Gly Leu Leu Pro Leu Phe Asp Glu Ser
            100                 105                 110

His Val Met Val Ser Glu Leu Ala Gly Asp Leu Leu Tyr Arg Arg Ile
        115                 120                 125

Ala Pro His Glu Val Ser Met Asn Arg Asn Ser Trp Ser Phe Trp Val
    130                 135                 140

Ser Ser Ala Ser Ser Arg Arg Asn Lys Met Ile Ser Gln Pro Ala Tyr
145                 150                 155                 160

Asn Thr Arg Leu Cys Arg Ala Ala Ser Pro Glu Gly Lys Cys Trp Ser
                165                 170                 175

Glu Leu Arg Ser Gly Glu Met Ile Lys Trp Gly Arg Arg Leu Arg Val
            180                 185                 190

Gln Tyr Lys Ser Arg His Ile Asp Cys Lys Lys Asn Thr Glu Gly Lys
        195                 200                 205

Glu Ser Ser Gly Val Lys Glu Gly Gly Val Cys Lys Glu Glu Ile Glu
    210                 215                 220

Glu Glu Asn Asp Asp Asp Asp Asp Gly Asn Glu Thr Glu Glu Thr Lys
225                 230                 235                 240

Gln Ile Ala Asn Glu Met Thr Asp Gly Asn Arg Lys Arg Lys Leu Ile
                245                 250                 255

Glu Ser Ser Thr Glu Arg Leu Ala Gln Arg Ala Lys Val Tyr Asp Gln
            260                 265                 270

Lys Lys Glu Asn Gln Ile Val Val Tyr Lys Arg Arg Ala Glu Lys Lys
        275                 280                 285

Phe Ile Gly Arg Trp Ser Val Asp Arg Tyr Lys Leu Ala Glu Arg Asn
    290                 295                 300

Met Leu Lys Val Met Lys Glu Lys Asn Ala Val Phe Gly Asn Ser Ile
305                 310                 315                 320

Leu Arg Ser Gln Leu Arg Ser Glu Ala Arg Lys Leu Ile Gly Asp Thr
                325                 330                 335
```

Gly Leu Leu Asp His Met Leu Lys His Met Ala Gly Lys Val Ala Pro
                340                 345                 350

Gly Gly Gln Asp Arg Phe Met Arg Lys His Asn Ala Asp Gly Ala Met
            355                 360                 365

Glu Tyr Trp Leu Glu Ser Ser Asp Leu Ile His Ile Arg Lys Glu Ala
370                 375                 380

Gly Val Glu Asp Pro Tyr Trp Thr Pro Pro Gly Trp Lys Leu Gly
385                 390                 395                 400

Asp Asn Pro Thr Gln Asp Pro Val Cys Ala Gly Glu Ile Arg Glu Ile
                405                 410                 415

Arg Glu Glu Leu Ala Ser Leu Arg Arg Glu Leu Glu Lys Leu Ala Ser
            420                 425                 430

Lys Lys Glu Glu Glu Glu Leu Val Ile Val Thr Thr Pro Asn Ser Cys
435                 440                 445

Val Thr Ser Gln Asn Val Asp Asn Asp Asn Leu Thr Thr Pro Ala Lys
            450                 455                 460

Glu Ile Tyr Ala Asp Leu Leu Lys Lys Lys Tyr Lys Ile Glu Asp Gln
465                 470                 475                 480

Leu Val Ile Ile Gly Glu Thr Leu Cys Thr Met Glu Glu Asp Met Gly
                485                 490                 495

Trp Leu Lys Lys Thr Val Asp Glu Asn Phe Pro Arg
            500                 505

<210> SEQ ID NO 20
<211> LENGTH: 1680
<212> TYPE: DNA
<213> ORGANISM: Oryza

<400> SEQUENCE: 20

| | | | | | |
|---|---|---|---|---|---|
| atggacgcgg | agatggcggc | tcctgcgctt | gcggcagctc | atctgctgga | ctcgcccatg | 60 |
| aggccacagg | tgagcagata | ctactccaag | aagaggggta | gcagccacag | cagaaatggc | 120 |
| aaggatgatg | ccaaccatga | cgagtccaag | aaccaatcac | ccggcttgcc | cctgagcaga | 180 |
| cagagcctgt | cctcatctgc | cacccacacc | taccacaccg | gagggttcta | cgagatcgac | 240 |
| cacgagaagc | ttcccccca | atccccaatt | catctcaagt | ccatacgcgt | ggtaaaggtg | 300 |
| agcggctaca | caagcctgga | cgtcacagtg | agcttcccgt | ccctcctggc | gctgcgaagc | 360 |
| ttcttctcct | cctccccacg | tcgtgcact | gggccgagc | tcgacgagcg | cttcgtcatg | 420 |
| agcagcaacc | acgcggcccg | catcctgcgc | cgtcgggtgg | ccgaggagga | gctcgcgggc | 480 |
| gacgtgatgc | accaggacag | cttctggctc | gtcaagccct | gcctctatga | cttctccgcg | 540 |
| tcgtcaccac | atgatgtgct | gaccccgtcg | ccgccgcctg | ccacagcgca | ggcgaaggcg | 600 |
| ccggcagcca | gttcctgcct | tctcgacacc | ttgaagtgcg | acggcgcgg | gtggggcgtg | 660 |
| aggcgccgtg | tcaggtacat | tggtcgccac | acgatgctt | ccaaggaggc | cagcgctgcc | 720 |
| agcctcgatg | gctacaacac | agaggtcagc | gtccaggagg | agcagcagca | gcgactgcgg | 780 |
| cttcgactgc | ggttgcgaca | cgccgggag | caggaagaca | caagagcac | tagcaatggc | 840 |
| aagaggaagc | gggaggaggc | agagagcagc | atggacaaga | gcagagccgc | caggaagaag | 900 |
| aaagccaaga | cttacaagag | tcccaagaag | gtggagaaga | ggcgcgtcgt | ggaggctaaa | 960 |
| gacggcgacc | ctcggcgcgg | caaggaccgg | tggtcggccg | agcggtacgc | agcggcggag | 1020 |
| aggagcctgc | tggatataat | gcgctcccat | ggtgcctgct | tcggtgcgcc | ggtgatgcgg | 1080 |
| caggctctgc | gggaggaagc | ccgcaagcat | atcggtgaca | ccggcctcct | tgaccacctg | 1140 |

-continued

```
ctcaagcaca tggccggcag ggtaccggaa ggcagcgcgg accggttccg tcgccggcac   1200
aatgcggatg gtgccatgga gtactggctg gagccggcgg agcttgccga ggtacgcgg    1260 ctggctggag tgtctgatcc atactgggtg ccgccacctg ggtggaagcc aggtgatgac   1320
gtgtccgcag tcgccggtga cctcctggtc aagaagaagg tggaagagct cgctgaggag   1380
gttgatggtg taaaaaggca catcgagcag ctcagttcta atttggtgca gctggagaag   1440
gaaacaaaat ctgaggcaga gcgatcttac agctctagga aggagaagta tcagaagttg   1500
atgaaggcaa atgaaaagct cgagaaacag gtgttatcta tgaaggataa atacaagctt   1560
gtgctggaga gaatgataa actggaggaa cagatggcta gtctctccag ctccttcctt    1620
tctttgaagg aacaattgct gctgccaaga aatggagata atctgaacat ggaaaggtaa   1680
```

<210> SEQ ID NO 21
<211> LENGTH: 559
<212> TYPE: PRT
<213> ORGANISM: Oryza

<400> SEQUENCE: 21

```
Met Asp Ala Glu Met Ala Ala Pro Ala Leu Ala Ala His Leu Leu
1               5                  10                  15

Asp Ser Pro Met Arg Pro Gln Val Ser Arg Tyr Tyr Ser Lys Lys Arg
                20                  25                  30

Gly Ser Ser His Ser Arg Asn Gly Lys Asp Asp Ala Asn His Asp Glu
            35                  40                  45

Ser Lys Asn Gln Ser Pro Gly Leu Pro Leu Ser Arg Gln Ser Leu Ser
        50                  55                  60

Ser Ser Ala Thr His Thr Tyr His Thr Gly Gly Phe Tyr Glu Ile Asp
65                  70                  75                  80

His Glu Lys Leu Pro Pro Lys Ser Pro Ile His Leu Lys Ser Ile Arg
                85                  90                  95

Val Val Lys Val Ser Gly Tyr Thr Ser Leu Asp Val Thr Val Ser Phe
            100                 105                 110

Pro Ser Leu Leu Ala Leu Arg Ser Phe Phe Ser Ser Pro Arg Ser
        115                 120                 125

Cys Thr Gly Pro Glu Leu Asp Glu Arg Phe Val Met Ser Ser Asn His
130                 135                 140

Ala Ala Arg Ile Leu Arg Arg Val Ala Glu Glu Leu Ala Gly
145                 150                 155                 160

Asp Val Met His Gln Asp Ser Phe Trp Leu Val Lys Pro Cys Leu Tyr
                165                 170                 175

Asp Phe Ser Ala Ser Ser Pro His Asp Val Leu Thr Pro Ser Pro Pro
            180                 185                 190

Pro Ala Thr Ala Gln Ala Lys Ala Pro Ala Ala Ser Ser Cys Leu Leu
        195                 200                 205

Asp Thr Leu Lys Cys Asp Gly Ala Gly Trp Gly Val Arg Arg Arg Val
210                 215                 220

Arg Tyr Ile Gly Arg His His Asp Ala Ser Lys Glu Ala Ser Ala Ala
225                 230                 235                 240

Ser Leu Asp Gly Tyr Asn Thr Glu Val Ser Val Gln Glu Glu Gln
                245                 250                 255

Gln Arg Leu Arg Leu Arg Leu Arg Leu Arg Gln Arg Glu Gln Glu
            260                 265                 270

Asp Asn Lys Ser Thr Ser Asn Gly Lys Arg Lys Arg Glu Glu Ala Glu
        275                 280                 285
```

Ser Ser Met Asp Lys Ser Arg Ala Ala Arg Lys Lys Ala Lys Thr
    290                 295                 300

Tyr Lys Ser Pro Lys Lys Val Glu Lys Arg Val Val Glu Ala Lys
305                 310                 315                 320

Asp Gly Asp Pro Arg Arg Gly Lys Asp Arg Trp Ser Ala Glu Arg Tyr
                325                 330                 335

Ala Ala Ala Glu Arg Ser Leu Leu Asp Ile Met Arg Ser His Gly Ala
            340                 345                 350

Cys Phe Gly Ala Pro Val Met Arg Gln Ala Leu Arg Glu Glu Ala Arg
        355                 360                 365

Lys His Ile Gly Asp Thr Gly Leu Leu Asp His Leu Leu Lys His Met
    370                 375                 380

Ala Gly Arg Val Pro Glu Gly Ser Ala Asp Arg Phe Arg Arg Arg His
385                 390                 395                 400

Asn Ala Asp Gly Ala Met Glu Tyr Trp Leu Glu Pro Ala Glu Leu Ala
                405                 410                 415

Glu Val Arg Arg Leu Ala Gly Val Ser Asp Pro Tyr Trp Val Pro Pro
            420                 425                 430

Pro Gly Trp Lys Pro Gly Asp Asp Val Ser Ala Val Ala Gly Asp Leu
        435                 440                 445

Leu Val Lys Lys Val Glu Glu Leu Ala Glu Glu Val Asp Gly Val
    450                 455                 460

Lys Arg His Ile Glu Gln Leu Ser Ser Asn Leu Val Gln Leu Glu Lys
465                 470                 475                 480

Glu Thr Lys Ser Glu Ala Glu Arg Ser Tyr Ser Arg Lys Glu Lys
                485                 490                 495

Tyr Gln Lys Leu Met Lys Ala Asn Glu Lys Leu Glu Lys Gln Val Leu
            500                 505                 510

Ser Met Lys Asp Lys Tyr Lys Leu Val Leu Glu Lys Asn Asp Lys Leu
        515                 520                 525

Glu Glu Gln Met Ala Ser Leu Ser Ser Ser Phe Leu Ser Leu Lys Glu
    530                 535                 540

Gln Leu Leu Leu Pro Arg Asn Gly Asp Asn Leu Asn Met Glu Arg
545                 550                 555

<210> SEQ ID NO 22
<211> LENGTH: 1612
<212> TYPE: DNA
<213> ORGANISM: Artificial Sequence
<220> FEATURE:
<223> OTHER INFORMATION: DYAD Promoter

<400> SEQUENCE: 22
gagctctttg gtccggagac ggtagaagac gacaaagcac tgacctttca tctctcggcg      60
atcgaaaaaa tcactctctt tcctcatcag acccgacccg ttatgaaggt atccagaccc     120
gtttattttg atccatctca tagtcggatc cccaaaaaaa ttcagcttag attggcccat     180
ttaggcccgt ttacagtttt ttactttttt cttaattatc ttttaacat cttacattat      240 acatatttga ctcaacaaaa aaatataact taaatgtatt gttgactgtt tttgataatt     300
aagaaaaaaa tattttaaa ttattaaaaa tattgttgac tcaacaaaaa aatataactt      360
aaatgtattg gcaaataat catggtcata agtcctcaag cttattattt gttttgattg     420
gtttaaatac tttataaaaa aaatatcaat tatatcatgt tattacgtaa attaagctt      480 ttgattttaa aaaagcttca gctcaataaa gaaaaacaga ttcagttatc attggagtat     540

```
aaaattggtc gatacattag agacattaat ccttacatca taaacaattt aatgtgaata      600
aaacatcata aatcacatat cattatccga aaataatcat atgtaagaat aatcactgtg      660
acaaaaaaaa aaaacaattc ctcacgtgtg tagtcggtcc ccactctagt agcagtagct      720
taatgatgcc ttctccgcac gtgtaacacg aaatttattc gctacggcca attacattaa      780
ccttcaggtc ttatcaccgt taaattttca aaatgacaca cgtggcatca atccgtaata      840
tcactacgtc tgctttcaat cttthcattgt agatgatttc gtacaccaat ttccgcgaac      900
gtttacagtt tagatacagt ttgagggcaa atctgtcaat atacgccaac ttgctgcgaa      960
agcaatatag tcacgtgccg tgcacacgca tataagactc acacactcac accactctct     1020
ctctctctct aacctcatat ataaagccac ctcccagatt cattaaatgc gacatttcaa     1080
aacttttctt tttgctgtct tcccataag ctctctgctg attaaaaga ttttctggta       1140 taaaacaaaa ttcttcaaat atttctgggt ttatgttttc tctctatttc tcagaaatgc     1200 tttaattct ccatccgcgt ccatgttttt ttttctccgt tgctgatttt gattttttta     1260
atccagtgaa aaggaggaac gaagattatc gagagcaaaa atcatgagtg taagatctct     1320
ctcgctctca gattttattt tttttcgctg tgatataaat ggctcagtca ctatcagtct     1380
catgatgaga aaataaaac tcatcaccgc ttgattctgt ttccttagtg tctcccacgc      1440
gcgtaccaga aagcgcgtgt gtgtttcttg ttatactcgc agagtcaggt tttttcaaat    1500
atattctctc caggcagcag caacaacaac aaaccgattt tttcattatt ccttataaca     1560 attttttgatt ctccagaaaa aaaatatctc tcttagtttt tctcttgttc ta            1612

<210> SEQ ID NO 23
<211> LENGTH: 2412
<212> TYPE: DNA
<213> ORGANISM: Oryza

<400> SEQUENCE: 23
atggacgcgg agatggcggc tcctgcgctt gcggcagctc atctgctgga ctcgcccatg        60
aggccacagg tgagcagata ctactccaag aagaggggta gcagccacag cagaaatggc      120
aaggatgatg ccaaccatga cgagtccaag aaccaatcac ccggcttgcc cctgagcaga      180
cagagcctgt cctcatctgc cacccacacc taccacaccg gagggttcta cgagatcgac      240
cacgagaagc ttccccccaa atccccaatt catctcaagt ccatacgcgt ggtaaaggtg      300
agcggctaca caagcctgga cgtcacagtg agcttcccgt ccctcctggc gctgcgaagc      360
ttcttctcct cctccccacg gtcgtgcact gggccggagc tcgacgagcg cttcgtcatg      420
agcagcaacc acgcggcccg catcctgcgc cgtcgggtgg ccgaggagga gctcgcgggc      480
gacgtgatgc accaggacag cttctggctc gtcaagccct gcctctatga cttctccgcg      540
tcgtcaccac atgatgtgct gaccccgtcg ccgccgcctg ccacagcgca ggcgaaggcg      600
ccggcagcca gttcctgcct tctcgacacc ttgaagtgcg acggcgcgg gtggggcgtg      660 aggcgccgtg tcaggtacat tggtcgccac cacgatgctt ccaaggaggc cagcgctgcc      720
agcctcgatg gctacaacac agaggtcagc gtccaggagg agcagcagca gcgactgcgg      780
cttcgactgc ggttgcgaca acgccgggag caggaagaca acaagagcac tagcaatggc      840
aagaggaagc gggaggaggc agagagcagc atggacaaga gcagagccgc caggaagaag      900
aaagccaaga cttacaagag tcccaagaag gtggagaaga ggcgcgtcgt ggaggctaaa      960 gacgcgacc ctcggcgcgg caaggaccgg tggtcggccg agcggtacgc agcggcggag     1020
```

| aggagcctgc tggatataat gcgctcccat ggtgcctgct tcggtgcgcc ggtgatgcgg | 1080 |
| caggctctgc gggaggaagc ccgcaagcat atcggtgaca ccggcctcct tgaccacctg | 1140 |
| ctcaagcaca tggccggcag ggtaccggaa ggcagcgcgg accggttccg tcgccggcac | 1200 |
| aatgcggatg gtgccatgga gtactggctg gagccggcgg agcttgccga ggtacgcgg | 1260 |
| ctggctggag tgtctgatcc atactgggtg ccgccacctg ggtggaagcc aggtgatgac | 1320 |
| gtgtccgcag tcgccggtga cctcctggtc aagaagaagg tggaagagct cgctgaggag | 1380 |
| gttgatggtg taaaaaggca catcgagcag ctcagttcta atttggtgca gctggagaag | 1440 |
| gaaacaaaat ctgaggcaga gcgatcttac agctctagga aggagaagta tcagaagttg | 1500 |
| atgaaggcaa atgaaaagct cgagaaacag gtgttatcta tgaaggacat gtatgagcat | 1560 |
| ctggttcaga aaagggtaa gctgaagaag gaggtgctgt ccttgaagga taaatacaag | 1620 |
| cttgtgctgg agaagaatga taaactggag gaacagatgg ctagtctctc cagctccttc | 1680 |
| cttctttga aggaacaatt gctgctgcca agaaatggag ataatctgaa catggaaagg | 1740 |
| gaaagggtgg aagtgacttt gggcaagcaa gaaggccttg ttcccggcga accactgtat | 1800 |
| gttgatggtg gtgaccggat cagccagcaa gcagatgcca ccgtcgtcca agtcggcgag | 1860 |
| aagaggacgg cgaggaagag cagcttccgc atctgcaagc cacagggaac gttcatgtgg | 1920 |
| ccacacatgg cgtctggcac gagcatggcc atcagtgggg gaggcagcag cagctgccct | 1980 |
| gtcgcctccg ggccagagca gctccctcgc agcagcagct gccccagcat tgggcctggt | 2040 |
| ggcctcccgc cgtcgtcacg agccccagcc gaggtggtgg tcgcgtcgcc actggacgag | 2100 |
| cacgtggcgt tccgcggggg cttcaacacg ccgcccctcgg catcgtccac caacgccgcc | 2160 |
| gctgccgcca agctgcctcc cctgcccagc ccgacgtcac ctctccagac acgggccctg | 2220 |
| ttcgccgctg gcttcactgt cccggcatta cacaacttct ccggcctcac cttacgccat | 2280 |
| gtggactcct cgtcgccgtc gtccgcgcca tgcggtgcta gggagaagat ggtgaccctg | 2340 |
| ttcgatggag actgccgggg gatcagcgtc gtgggcaccg agctggcact ggccactccg | 2400 |
| tcctactgct ga | 2412 |

<210> SEQ ID NO 24
<211> LENGTH: 6329
<212> TYPE: DNA
<213> ORGANISM: Populus trichocarpa

<400> SEQUENCE: 24

| cattcgttat ggctaacgga gtcactgggc cttacatgca tccacagacc aggtgccgga | 60 |
| gtgctggtgc aaaaccaatt tattgaattt ctgaacaatt ggagacgaaa taaatgtctt | 120 |
| tacttcttca aacccttgat ttaaaagtaa atgtattatc ttttattgat tttttattc | 180 |
| aattcctaga attagtagct tgaagaattt attaaattta tcagataaat gagagggata | 240 |
| tacccttaaa atcgtcaaaa ataaatctca atttacttat aaattgaaga atacttctt | 300 |
| aaaaataaaa taaaattgcg tgccatccct ctttagtaga ttttggcgct actcgtgtgg | 360 |
| tgtgggtaca gagaagaata ttaatatacc cgagctggaa ctagaaggtc acccgccata | 420 |
| tccaatgagg caatcccgaa cctctcccac aagcaagcat ccgccacgtg gtcagaagct | 480 |
| acagaggtta tgacctggct aaacgattgg ctaccaggaa ccaatggctc ctcaaaggcc | 540 |
| atagataaat aaatctaaga gccagttct ttagctctca actctctcaa ccatctatac | 600 |
| aacatttcca gaggcaacaa gactcggag gggtaaaacg gtaaaatggg agacgttact | 660 |
| gtagaggagg gaggggggga ccagaatcca ggtcacgtga ggcgcatccc gtctggtaat | 720 |

```
aatcattact attttttct ctctttatag cagaaatgca ccaccatcgt tggtttcaca      780
acagaaaaaa ctccctcccc cttctctctg cgttttctct caagctgttt tttcttgctc      840
tccaaacaat ccatcacaag tagcttttga aacagaaatt gaaaaaaaaa ggtctcgttt      900
tatatttatt tttgctgttt aattttcaac ctgattttt tcatgtgcat taattaatta       960
atgctggtgt agttactctt tggctggttg aatcggtgct ggtactggat aaaacatctc     1020 aaaggaatg acccatttgc atgtcattaa ggggtgcatg tgtttgaatg aggaattcaa      1080
acaagtcctg acatgagtat gcattttcct gtggttaaca gatataggtt gtttggctcc     1140
tggaagattc tcaaaattga gatttcaagc tcaaaagtgt ttttgataca cttttccaagc    1200 ttcatgatct ttaatttacc agtggtgttt ttcctagtta gtgtacttta aaggtcgcat     1260
aatgatcggt agtacttagc tttgattttg cattcccgtt cgcttcttct tgttttcagt    1320
ctctgcgtac caacaatata gagattctcc tggctgtgca agaatcacta tatctatcta    1380
tctatctatc aggccttaac cttgcttct ttctgatca atccttgtgt ttatgattga       1440
ttaatgagat taattgtatg tttgcttcaa atgattatct tatatatagt ctgattttcc    1500
cttctcttaa tcatgtccat atatgtttat tcgccggggg gccggaagg acgagaggta     1560 cgactagcta gtattaactt gtgcagttga aactgtttct ctatgtgcag aagatgacta    1620
ccatggagct ggttgatgtt gcagtgatag accaccatc ggtgagtttg ttctctcttc      1680
tcctcaatcc cactcccact ctccactccc caaccaccac accccttct ttctgttact     1740 cctctatttc tcttctcgta acccacgcgc tcttttatct ctcaaatcaa gtcgctgatt    1800
actagtctac taaagttttc aaatactcaa ccgaattcct aatctttgtc tcacgctcac    1860
acacatacca aatccacacg cgcgtcccct acaatttgtt acgcaaatca aaccccgctc    1920
tacacatcct tggtgcccaa gtaagtgaaa tgatgatttt acataacaaa accacataa     1980 ttattatgct atgtaacggt atattctata cattctctat cgagtattgc cacgaggggg    2040
cttatgcata cataaatcct caccccttt aaaggagaag ggcaatacag tgattttggt    2100
tgtgcttgtg aaaatgcagg aaataaaaag gaggcagaac tccgaggacg ccgatagaag    2160 gcttttttg ggcggacatt gcctgcatca cccaacattt accacagcac caccatttgg     2220
taatatttgt aacacacacg cacacacgcc cgagcaacaa atctctccct ctttttttatc   2280 ccttttgttt cctctctctc tctctctctc tctcacttga tttctctctt ctgatttgct    2340
gatttttttt actgctcgta ctagctagct agctctactc ctatagctca cagtactgca    2400
agtacgtagt actactgcag ctgctgctag tgctagtagt agctatgtcg ttttccacgc    2460
taagagctct tgtttctgat caaaataagg aattctctga ttactctttg ttttccatgc    2520
ttaataatga agacccagct gagcatatta aagtgagctc ttttttatgaa gttgatcact   2580 ccaagctgcc tcataaatcc cctgatcaac tcaacaaaac ccgggttgtg atggtatttt    2640
ttatacaatt caacaatatt cttaaacccg gctcaacatt ttttctctc tgctttaaaa     2700 tttgttggtg tttgtttctg cttgaataaa tatctcaggt gaatgaaaag accaggatga    2760
gagtctcgct gaggtttcca agcatcaatt ctctaagatg ttacttcaat gagattgaag    2820
ctattaatta caagaaagac atgaaaacga agaagcagca gctaccagca ttcgacgaga    2880
aatacattat aggatcagaa gttgcagggg aagctcttta taggagaatc tcttctcaag    2940 aaaatggcaga caagagttac tcatggagtt tctggatggt taaacatcct tcggtttcac   3000
ctcgaaaagt gtcataccca cctacaagta ctcatgttaa taaatttgtt ggtgcaagga    3060
```

```
aggtgtctct catgtctgag ctcaacggga caggcatggt taagtggggt cagcgccggc    3120
aggtcaggtt cttggctaaa cacgtagagg ataaacgtga aatagtgatt gcatcgaagg    3180
atttgattaa aagcgaagaa gagaaagaca gtgatggtag tgatgatgac acagacgatg    3240
aggacgagga ggaggtcgat gttaagttag tagtaaacaa gtcaagtgaa gctaaaagga    3300
aattacgtaa gagaaagtgt caaggtgggt ctggtattag caaattatca ccaaaaaga    3360 aaaggcgtaa aattgaaaag aagaaccaga ttgtggtcta taggcaaaag aagaacaaac    3420
tcatcaagaa ttctattgac agatggtctg cggggaggta ataaagcttt tattagttaa    3480
taaactaaat tcagatcgtc atttgtgtta atatattttt ttgattagtg tctatatgta    3540
gctagctaat ttggttgggt gatttctgtg aaggtataaa ttggctgagg aaaacatgtt    3600
aaaggtaatg aaagagcaaa atgctgtgtt tcgacgccca attttaaggc cagaattgag    3660
agctgaggca cggaagttga ttggggatac tgggctgtta gaccacttgt tgaagcatat    3720
gtcagggaag gtggctccgg gaggagaaga gagattcaga aggaggcata acgcagatgg    3780
agcaatggag tattggctgg agaaggctga tttggttgat atcaggaaag aggctggtgt    3840
gcaggatcct tattggacac ctccacctgg gtggaaacct ggtgataatc ctagtcagga    3900
tccagtttgt gctagagaga tcaaggaact cagagaagaa attgctaaaa ttaaagggta    3960
ctggtccttc tgttttaact aggattgatt gtctttcaat tttgtgtggt cttttagctt    4020
gttagtgctg ttgatctggt aatgcccacc agttttctc tgttactctt ggggtgaatt    4080
gtgtgcgcta ctgattccat ctctcgcgta tgtgttgttc ttatgggggg caggagatg    4140 gaggcaatgg tgtctaaaaa acacggggag gaattagcaa tggtggcagc accgaattat    4200
tctcctacaa gtcaggacat ggagcatgac aacttcttaa ttccactgaa ggtaatagat    4260
atgaaagttt gaccagattt ttggactgac ccaagttctt ctcttgacaa tccatgtact    4320 attttgcag gaaatgtaca ttgatttggt gaataagaag gtaaagatgg aggaacaact    4380
aaaggaaatt tcagaatctt tgtatgggat gaaggtagga gagcatgaga attcttcctt    4440
taataattat cattttcttt tcaattgaag tgtgtaagat ttgatatgaa tgattctttc    4500
cacgttatga cgttctgggt gctactagtg tatataagat tcgttcaaat aagaaattcc    4560
tgggtgattg catgatccac atcattgaaa gatggtagta acaaactgac catctgatgc    4620
atgtatctat tctagataat aagttgatgc ataaattgcc atgaaaccat ttgagaagct    4680
gttatattta gaggcttgat atgggagtgt tgcttattcc agactagatt tttgcaatta    4740
tttagttcaa tttaaagctc aaaatcccac attaaatagt ttcataaatg atgaatgttc    4800
tggcagtgga tttccgttgt ccttggtagt actttctaat ctggacagca tttatattgt    4860
aacaatgata cgcttaatga tgatcttagg atgaattggt tagttatgaa tttagttgtc    4920
cttacagtgc aacggggagg cttggctgca tttattgttg tagcatttaa ttatgcattg    4980
aacgcggtca ttattgtgat gatggaaata tttaattgat gcaggaagaa atggagaagc    5040 taaaaccag agtggagaaa tcaaacagag cagaatcaac tgaaaagcca gctttattaa    5100
tgggctcaac agagtcaatc acgccagcag gaactggaag aaaggggaaa ggagtaatgc    5160
atcaggaaaa agaagcaacg gttttagggg aatcagcaca agaacaatgc aagtcatcat    5220
caggaggcat catagcacca agaacagaat caccagcacc aacggaggac agggcagcaa    5280
agatagagag gctgaaaagc gggttttagaa tatgcaagcc ccagggaagt ttcctgtggc    5340
cggatatgac taccttaacc cctcacccctc aggttgtggt cctactagaa gacctcattg    5400
cggtacaaac acctccctca gtgtcctcca ctacaccaaa acaatctcac ttcctctttg    5460
```

| | |
|---|---|
| ctcctccatc tcaaacccat acaccccacc gtactttccc tgtgaagcca ttagctgaga | 5520 |
| gaaggcctgt caccattccc caatccacag ctgccacgac tccaaccagc tgtcctcccc | 5580 |
| ttgatcaaat gactcactcc cagtatgaga atagcagcat ttccacttct actaccatca | 5640 |
| ccaccactac caaaacccct ctcatcaacc ttaatgagcc actgaatacc aatcaaactg | 5700 |
| atgattatgg attgttttat gggtctcagt ctcatgctga agcctctcct caccctgtca | 5760 |
| cttaccaaag aagacatcat caaaatgtga ccaccagtat tgccatgcca agtgtatgtg | 5820 |
| tacttatcaa atctcaattt caattcatac ccatatttta gtgatactat catagtatac | 5880 |
| aagttgactc ctttttcatt ttctgtatgt tttacacagt tgggacccac aaagaaaggg | 5940 |
| atgatgagcc aatgggagga aggtgatcgg agaaaaggaa tgataaggta ctgtgagcag | 6000 |
| tgtgagcagc aacagggatg ctcctctgcc tcttccattg catcttcttc cttgccaatg | 6060 |
| ggaaagggga cttggttggc tctggctact tctaaggctt ccgtggagca caaatctaaa | 6120 |
| aggggttaaa caatctataa taataatagt agtagtaata atggctagtt tattatgcta | 6180 |
| gagtagttat tagttaaacc cctggaaaaa cattgattag gttgggtttc acttaatgct | 6240 |
| ttccctgtct ttgggcaagg aatcttctta acatagttat atacatatgg catatacaag | 6300 |
| gcacaaagag cttttagcgt ataggaaaaa | 6329 |

<210> SEQ ID NO 25
<211> LENGTH: 2493
<212> TYPE: DNA
<213> ORGANISM: Populus trichocarpa

<400> SEQUENCE: 25

| | |
|---|---|
| atgtcgtttt ccacgctaag agctcttgtt tctgatcaaa ataaggaatt ctctgattac | 60 |
| tctttgtttt ccatgcttaa taatgaagac ccagctgagc atattaaagt gagctctttt | 120 |
| tatgaagttg atcactccaa gctgcctcat aaatcccctg atcaactcaa caaaacccgg | 180 |
| gttgtgatgg tgaatgaaaa gaccaggatg agagtctcgc tgaggtttcc aagcatcaat | 240 |
| tctctaagat gttacttcaa tgagattgaa gctattaatt acaagaaaga catgaaaacg | 300 |
| aagaagcagc agctaccagc attcgacgag aaatacatta taggatcaga agttgcaggg | 360 |
| gaagctcttt ataggagaat ctcttctcaa gaaatggcag acaagagtta ctcatggagt | 420 |
| ttctggatgg ttaaacatcc ttcggtttca cctcgaaaag tgtcataccc acctacaagt | 480 |
| actcatgtta ataaatttgt tggtgcaagg aaggtgtctc tcatgtctga gctcaacggg | 540 |
| acaggcatgt ttaagtgggg tcagcgccgg caggtcaggt tcttggctaa acacgtagag | 600 |
| gataaacgtg aaatagtgat tgcatcgaag gatttgatta aagcgaaga agagaaagac | 660 |
| agtgatggta gtgatgatga cacagacgat gaggacgagg aggaggtcga tgttaagtta | 720 |
| gtagtaaaca agtcaagtga agctaaaagg aaattacgta agagaaagtg tcaaggtggg | 780 |
| tctggtatta gcaaattatc accaaaaaag aaaggcgta aaattgaaaa gaagaaccag | 840 |
| attgtggtct ataggcaaaa gaagaacaaa ctcatcaaga attctattga cagatggtct | 900 |
| gcggggaggt ataaattggc tgaggaaaac atgttaaagg taatgaaaga gcaaaatgct | 960 |
| gtgtttcgac gcccaatttt aaggccagaa ttgagagctg aggcacggaa gttgattggg | 1020 |
| gatactgggc tgttagacca cttgttgaag catatgtcag ggaaggtggc tccgggagga | 1080 |
| gaagagagat tcagaaggag gcataacgca gatggagcaa tggagtattg gctggagaag | 1140 |
| gctgatttgg ttgatatcag gaaagaggct ggtgtgcagg atccttattg gacacctcca | 1200 |

```
cctgggtgga aacctggtga taatcctagt caggatccag tttgtgctag agagatcaag    1260
gaactcagag aagaaattgc taaaattaaa ggggagatgg aggcaatggt gtctaaaaaa    1320
cacggggagg aattagcaat ggtggcagca ccgaattatt ctcctacaag tcaggacatg    1380
gagcatgaca acttcttaat tccactgaag gaaatgtaca ttgatttggt gaataagaag    1440
gtaaagatgg aggaacaact aaaggaaatt tcagaatctt tgtatgggat gaaggaagaa    1500
atggagaagc taaaaaccag agtggagaaa tcaaacagag cagaatcaac tgaaaagcca    1560
gctttattaa tgggctcaac agagtcaatc acgccagcag gaactggaag aaagggggaaa    1620 ggagtaatgc atcaggaaaa agaagcaacg ttttagggg aatcagcaca agaacaatgc    1680
aagtcatcat caggaggcat catagcacca agaacagaat caccagcacc aacggaggac    1740
agggcagcaa agatagagag gctgaaaagc gggtttagaa tatgcaagcc ccagggaagt    1800
ttcctgtggc cggatatgac taccttaacc cctcaccctc aggttgtggt cctactagaa    1860
gacctcattg cggtacaaac acctccctca gtgtcctcca ctacaccaaa acaatctcac    1920
ttcctctttg ctcctccatc tcaaacccat acaccccacc gtactttccc tgtgaagcca    1980
ttagctgaga gaaggcctgt caccattccc caatccacag ctgccacgac tccaaccagc    2040
tgtcctcccc ttgatcaaat gactcactcc cagtatgaga atagcagcat ttccacttct    2100
actaccatca ccaccactac caaaacccct ctcatcaacc ttaatgagcc actgaatacc    2160
aatcaaactg atgattatgg attgttttat gggtctcagt ctcatgctga agcctctcct    2220
caccctgtca cttaccaaag aagacatcat caaaatgtga ccaccagtat tgccatgcca    2280
agtttgggac ccacaaagaa agggatgatg agccaatggg aggaaggtga tcggagaaaa    2340
ggaatgataa ggtactgtga gcagtgtgag cagcaacagg gatgctcctc tgcctcttcc    2400
attgcatctt cttccttgcc aatgggaaag gggacttggt tggctctggc tacttctaag    2460
gcttccgtgg agcacaaatc taaaaggggt taa                                2493
```

<210> SEQ ID NO 26
<211> LENGTH: 830
<212> TYPE: PRT
<213> ORGANISM: Populus trichocarpa

<400> SEQUENCE: 26

```
Met Ser Phe Ser Thr Leu Arg Ala Leu Val Ser Asp Gln Asn Lys Glu
1               5                   10                  15

Phe Ser Asp Tyr Ser Leu Phe Ser Met Leu Asn Asn Glu Asp Pro Ala
            20                  25                  30

Glu His Ile Lys Val Ser Ser Phe Tyr Glu Val Asp His Ser Lys Leu
        35                  40                  45

Pro His Lys Ser Pro Asp Gln Leu Asn Lys Thr Arg Val Val Met Val
    50                  55                  60

Asn Glu Lys Thr Arg Met Arg Val Ser Leu Arg Phe Pro Ser Ile Asn
65                  70                  75                  80

Ser Leu Arg Cys Tyr Phe Asn Glu Ile Glu Ala Ile Asn Tyr Lys Lys
                85                  90                  95

Asp Met Lys Thr Lys Lys Gln Gln Leu Pro Ala Phe Asp Glu Lys Tyr
            100                 105                 110

Ile Ile Gly Ser Glu Val Ala Gly Glu Ala Leu Tyr Arg Arg Ile Ser
        115                 120                 125

Ser Gln Glu Met Ala Asp Lys Ser Tyr Ser Trp Ser Phe Trp Met Val
    130                 135                 140
```

```
Lys His Pro Ser Val Ser Pro Arg Lys Val Ser Tyr Pro Pro Thr Ser
145                 150                 155                 160

Thr His Val Asn Lys Phe Val Gly Ala Arg Lys Val Ser Leu Met Ser
            165                 170                 175

Glu Leu Asn Gly Thr Gly Met Val Lys Trp Gly Gln Arg Arg Gln Val
        180                 185                 190

Arg Phe Leu Ala Lys His Val Glu Asp Lys Arg Glu Ile Val Ile Ala
    195                 200                 205

Ser Lys Asp Leu Ile Lys Ser Glu Glu Lys Asp Ser Asp Gly Ser
210                 215                 220

Asp Asp Asp Thr Asp Asp Glu Asp Glu Glu Val Asp Val Lys Leu
225                 230                 235                 240

Val Val Asn Lys Ser Ser Glu Ala Lys Arg Lys Leu Arg Lys Arg Lys
            245                 250                 255

Cys Gln Gly Gly Ser Gly Ile Ser Lys Leu Ser Pro Lys Lys Lys Arg
            260                 265                 270

Arg Lys Ile Glu Lys Lys Asn Gln Ile Val Val Tyr Arg Gln Lys Lys
        275                 280                 285

Asn Lys Leu Ile Lys Asn Ser Ile Asp Arg Trp Ser Ala Gly Arg Tyr
    290                 295                 300

Lys Leu Ala Glu Glu Asn Met Leu Lys Val Met Lys Glu Gln Asn Ala
305                 310                 315                 320

Val Phe Arg Arg Pro Ile Leu Arg Pro Glu Leu Arg Ala Glu Ala Arg
                325                 330                 335

Lys Leu Ile Gly Asp Thr Gly Leu Leu Asp His Leu Leu Lys His Met
            340                 345                 350

Ser Gly Lys Val Ala Pro Gly Gly Glu Glu Arg Phe Arg Arg Arg His
        355                 360                 365

Asn Ala Asp Gly Ala Met Glu Tyr Trp Leu Glu Lys Ala Asp Leu Val
    370                 375                 380

Asp Ile Arg Lys Glu Ala Gly Val Gln Asp Pro Tyr Trp Thr Pro Pro
385                 390                 395                 400

Pro Gly Trp Lys Pro Gly Asp Asn Pro Ser Gln Asp Pro Val Cys Ala
                405                 410                 415

Arg Glu Ile Lys Glu Leu Arg Glu Glu Ile Ala Lys Ile Lys Gly Glu
            420                 425                 430

Met Glu Ala Met Val Ser Lys Lys His Gly Glu Glu Leu Ala Met Val
        435                 440                 445

Ala Ala Pro Asn Tyr Ser Pro Thr Ser Gln Asp Met Glu His Asp Asn
450                 455                 460

Phe Leu Ile Pro Leu Lys Glu Met Tyr Ile Asp Leu Val Asn Lys Lys
465                 470                 475                 480

Val Lys Met Glu Glu Gln Leu Lys Glu Ile Glu Ser Leu Tyr Gly
            485                 490                 495

Met Lys Glu Glu Met Glu Lys Leu Lys Thr Arg Val Glu Lys Ser Asn
        500                 505                 510

Arg Ala Glu Ser Thr Glu Lys Pro Ala Leu Leu Met Gly Ser Thr Glu
    515                 520                 525

Ser Ile Thr Pro Ala Gly Thr Gly Arg Lys Gly Lys Val Met His
        530                 535                 540

Gln Glu Lys Glu Ala Thr Val Leu Gly Glu Ser Ala Gln Glu Gln Cys
545                 550                 555                 560

Lys Ser Ser Ser Gly Gly Ile Ile Ala Pro Arg Thr Glu Ser Pro Ala
```

```
                        565                 570                 575
Pro Thr Glu Asp Arg Ala Ala Lys Ile Glu Arg Leu Lys Ser Gly Phe
                    580                 585                 590

Arg Ile Cys Lys Pro Gln Gly Ser Phe Leu Trp Pro Asp Met Thr Thr
                595                 600                 605

Leu Thr Pro His Pro Gln Val Val Leu Leu Glu Asp Leu Ile Ala
            610                 615                 620

Val Gln Thr Pro Pro Ser Val Ser Ser Thr Thr Pro Lys Gln Ser His
625                 630                 635                 640

Phe Leu Phe Ala Pro Pro Ser Gln Thr His Thr Pro His Arg Thr Phe
                645                 650                 655

Pro Val Lys Pro Leu Ala Glu Arg Arg Pro Val Thr Ile Pro Gln Ser
            660                 665                 670

Thr Ala Ala Thr Thr Pro Thr Ser Cys Pro Pro Leu Asp Gln Met Thr
                675                 680                 685

His Ser Gln Tyr Glu Asn Ser Ser Ile Ser Thr Ser Thr Ile Thr
            690                 695                 700

Thr Thr Thr Lys Thr Pro Leu Ile Asn Leu Asn Glu Pro Leu Asn Thr
705                 710                 715                 720

Asn Gln Thr Asp Asp Tyr Gly Leu Phe Tyr Gly Ser Gln Ser His Ala
                725                 730                 735

Glu Ala Ser Pro His Pro Val Thr Tyr Gln Arg Arg His His Gln Asn
            740                 745                 750

Val Thr Thr Ser Ile Ala Met Pro Ser Leu Gly Pro Thr Lys Lys Gly
                755                 760                 765

Met Met Ser Gln Trp Glu Glu Gly Asp Arg Arg Lys Gly Met Ile Arg
            770                 775                 780

Tyr Cys Glu Gln Cys Glu Gln Gln Gly Cys Ser Ser Ala Ser Ser
785                 790                 795                 800

Ile Ala Ser Ser Ser Leu Pro Met Gly Lys Gly Thr Trp Leu Ala Leu
                805                 810                 815

Ala Thr Ser Lys Ala Ser Val Glu His Lys Ser Lys Arg Gly
                820                 825                 830

<210> SEQ ID NO 27
<211> LENGTH: 914
<212> TYPE: DNA
<213> ORGANISM: Rat

<400> SEQUENCE: 27
ggatcctgaa gctcgaaaaa caagaaaaa aatcaagggg attcagcaag ccactgcagg     60
agtctcacaa gacacttcgg aaaatcctaa caaaacaata gttcctgcag cattaccaca    120
gctcacccct accttggtgt cactgctgga ggtgattgaa cccgaggtgt tgtatgcagg    180
atatgatagc tctgttccag attcagcatg gagaattatg accacactca acatgttagg    240
tgggcgtcaa gtgattgcag cagtgaaatg ggcaaaggcg ataccaggct tcagaaactt    300
acacctggat gaccaaatga ccctgctaca gtactcatgg atgtttctca tggcatttgc    360
cctgggttgg agatcataca gacaatcaag tggaaacctg ctctgctttg ctcctgatct    420
gattattaat gagcagagaa tgtctctacc ctgcatgtat gaccaatgta aacacatgct    480
gtttgtctcc tctgaattac aaagattgca ggtatcctat gaagagtatc tctgtatgaa    540
aaccttactg cttctctcct cagttcctaa ggaaggtctg aagagccaag agttatttga    600
tgagattcga atgacttata tcaaagagct aggaaaagcc atcgtcaaaa gggaagggaa    660
```

```
ctccagtcag aactggcaac ggttttacca actgacaaag cttctggact ccatgcatga    720
ggtggttgag aatctcctta cctactgctt ccagacattt ttggataaga ccatgagtat    780
tgaattccca gagatgttag ctgaaatcat cactaatcag ataccaaaat attcaaatgg    840
aaatatcaaa aagcttctgt ttcatcaaaa atgactgacc tagttctaga gcggccgcca    900
ccgcggtgga gctc                                                      914
```

<210> SEQ ID NO 28
<211> LENGTH: 5807
<212> TYPE: DNA
<213> ORGANISM: Arabidopsis thaliana
<220> FEATURE:
<223> OTHER INFORMATION: DYAD Genomic sequence used for cloning as a Sal1 fragment

<400> SEQUENCE: 28

```
gtcgactttt tgtttgacca gtgtatttgg tttgacttca gatttggcaa gtacgaagct     60
tatgcgcttt tgcaatcgaa acaagggaaa aatctgtact tgttagctg cgtgacttga    120 gctctttggt ccggagacgg tagaagacga caaagcactg acctttcatc tctcggcgat    180
cgaaaaaatc actctctttc ctcatcagac ccgacccgtt atgaaggtat ccagacccgt    240
ttattttgat ccatctcata gtcggatccc caaaaaaatt cagcttagat tggcccattt    300
aggcccgttt acagttttttt actttttttct taattatctt tttaacatct tacattatac    360
atatttgact caacaaaaaa atataactta aatgtattgt tgactgtttt tgataattaa    420
gaaaaaaata ttttaaatt attaaaaata ttgttgactc aacaaaaaaa tataacttaa    480
atgtattggg caaataatca tggtcataag tcctcaagct tattatttgt tttgattggt    540
ttaaatactt tataaaaaaa atatcaatta tatcatgtta ttacgtaaat taagcttttt    600
gattttaaaa aagcttcagc tcaataaaga aaaacagatt cagttatcat tggagtataa    660
aattggtcga tacattagag acattaatcc ttacatcata aacaatttaa tgtgaataaa    720
acatcataaa tcacatatca ttatccgaaa ataatcatat gtaagaataa tcactgtgac    780
aaaaaaaaaa aacaattcct cacgtgtgta gtcggtcccc actctagtag cagtagctta    840
atgatgcctt ctccgcacgt gtaacacgaa atttattcgc tacggccaat tacattaacc    900
ttcaggtctt atcaccgtta aattttcaaa atgacacacg tggcatcaat ccgtaatatc    960
actacgtctg ctttcaatct ttcattgtag atgatttcgt acaccaattt ccgcgaacgt   1020
ttacagttta gatacagttt gagggcaaat ctgtcaatat acgccaactt gctgcgaaag   1080
caatatagtc acgtgccgtg cacacgcata taagactcac acactcacac cactctctct   1140
ctctctctaa cctcatatat aaagccacct cccagattca ttaaatgcga catttcaaaa   1200 cttttcttt tgctgtcttc cccataagct ctctgctgat taaaaagatt ttctggtata   1260
aaacaaaatt cttcaaatat ttctgggttt atgttttctc tctatttctc agaaatgctt   1320
taatttctcc atccgcgtcc atgttttttt ttctccgttg ctgattttga tttttttaat   1380
ccagtgaaaa ggaggaacga agattatcga gagcaaaaat catgagtgta agatctctct   1440
cgctctcaga tttatttttt tttcgctgtg atataaatgg ctcagtcact atcagtctca   1500
tgatgagaaa aataaaactc atcaccgctt gattctgttt ccttagtgtc tcccacgcgc   1560
gtaccagaaa gcgcgtgtgt gtttcttgtt atactcgcag agtcaggttt tttcaaatat   1620
attctctcca ggcagcagca acaacaacaa accgattttt tcattattcc ttataacaat   1680
ttttgattct ccagaaaaaa aatatctctc ttagtttttc tcttgttcta cagagtacga   1740
```

```
tgttcgtgaa acggaatccg attagagaaa ccaccgccgg gaaaatctct tcgccgtcgt      1800
caccgacttt gaatggtaaa ctactgaagc tatagtttct tcgtttttgt tgattttctc      1860
gcttctcttc taatttctga attttttggtt tgggtttgtt cttacagttg cagtcgcgca     1920
tataagagct ggatcttatt acgaaatcga tgcttcgatt cttcctcaga gatcgccgga     1980
aaatcttaaa tcgattagag tcgtcatggt attcactcga ttctctgctt ttttcacctt      2040
ttattataga cagatctcgt ttttttgttgt tcgtctgggt tttcgagtga ttttttaagg    2100
tttattgatg caggtgagca aaatcacggc gagtgacgtg tctctccggt acccaagcat      2160
gttttcactc cgatcgcatt tcgattacag taggatgaac cggaataaac cgatgaagaa     2220
gaggagtggt ggtggtcttc ttcctgtttt cgacgagagt catgtgatgg cttcggagct      2280
agctggagac ttgctttaca gaagaatcgc acctcatgaa cttctatga atagaaattc      2340 ctggggtttc tgggtttcta gttcttctcg caggaacaaa tttccaagaa gggaggtggt     2400
ttctcaaccg gcgtacaata ctcgtctctg tcgcgctgct tcaccggagg gaaagtgctc     2460
gtctgagctg aaatcgggag ggatgatcaa gtggggaagg agattgcgtg tgcagtatca     2520
gagtcggcat attgatacta ggaagaataa ggaaggtgag gagagttcta gagtgaagga    2580
tgaagtttac aaagaagaag agatggagaa agaagaggat gatgatgatg ggaatgaaat      2640
aggaggcact aaacaagagg caaaggagat aactaatgga aatcgtaaga gaaagctgat     2700
tgaatcaagt actgagagac tcgctcagaa agctaaggtt tatgatcaga agaaggaaac     2760
tcaaattgtg gttataaga ggaaatcaga gaggaagttc attgatagat ggtctgttga       2820
gaggtaaaat gcataaaaat taacgaattt tatgatctct gaatttggat tttccttggt      2880
tctattgatt gattgtggtt aattttgaag gtacaaacta gctgagagga acatgttaaa      2940
agtgatgaag gagaagaatg cagtgtttgg caactccata ctcaggccag agttgaggtc     3000
agaagcaagg aagctgattg gtgacacagg tctattggat catctgctta agcacatggc    3060
tggtaaggtg gctcctggag gtcaagatag gtttatgaga aagcacaatg cagatggggc     3120
aatggagtat tggttggaga gttctgattt gattcacata aggaagaag caggagttaa      3180 agatccttac tggactcctc cacctggttg gaagcttggt gacaacccctt ctcaagatcc    3240 tgtctgcgct ggagaaatcc gtgacatcag agaagaatta gctagcctga aaaggtagaa     3300
aagttattga attggttata cgatcatctc cctttagttg tcttattgca attttaactc     3360
atgtctgtct tggtcttgag aagagaattg aagaaacttg cgtcaaagaa ggaagaggag    3420
gagcttgtta tcatgactac gcctaattct tgtgttacta gtcagaatga taatctgatg    3480
actccagcaa aggtaagagc tcgaaacaat agctgaggcc tctctcttgt gaaaatgttt    3540
tatgctactt tgtgaacatc tctgctgctt tttcttagga aatctacgct gatctgctga    3600
aaaagaaata caaaattgag gaccagctag tgattattgg agaaaccttg cgtaaaatgg    3660
aggtatgtat atccctagat tgagtttcca agtagacaca aacccttact taaaatgtaa    3720
aatcttgatt tagtaactat cacaagtagt cataggaaac tcccttggag gataacagtg    3780
aaccatgtaa aatgggccca tttagcgtat gtgataaatg atttcctctg tctctatgag    3840
agaccacttt gctgatagtc gaataatgat gaaacatttg tgttactata aatgcaaata    3900
ttgcaggaag acatgggatg gcttaagaaa acagtggacg agaactatcc taaaaagcca    3960
gactcaacag agacaccttt gctactagag gattcaccac caatacagac actgaaagga    4020
gaagtgaagg tggtgaacaa gggtaaccaa atcacagagt cacctcaaaa cagagaaaaa    4080
```

```
ggaaggaagc atgatcaaca agaaagatca ccactttcac taataagcaa cactggtttc    4140
agaatctgca ggcctgtggg gatgttcgca tggccccaat tgcctgctct tgctgctgct    4200
actgatacta atgcttcttc gccaagtcac agacaagcct acccatcccc ttttccagtc    4260
aagccacttg cagctaagcg tcctcttggc ttgacgtttc ccttcaccat catacccgaa    4320
gaagctccca agaatctctt caacgtttga agttgtcact ggaaactgat gcatcagatc    4380
ttactttccc tacaagtaag ctgatgtgaa ctggtaaggt ctcttccatg aaatatataa    4440
taacttacaa gcgagcaggt atttaaaagt accacttata tttatataag gaactatatt    4500
tatgggaata atttggcaac ttttttgaaat tattcctctt taatttaggg attttacgtc    4560
tctggttatt aattatatat agagagagat gatttgaaat agagaggctt atcataggaa    4620
tatattcttt tgaaagacag ggatcatcat attctgtatt actgaacaat ttctataatg    4680
atacagttat atatatatat atatacttat tattcaattc ctagcgcttt tgattttaaa    4740
tatattattt tcgtgtagtt gattaatttt gaaaaacttg tattacgcat atgaattatg    4800
tcccgttgat ctataaaaat catattttgc gattaagcac aaactataaa agtatgttta    4860
agttcctgcg ggttgaccag tttcacttta aaatcttggt ctttgggatg agtttgccga    4920
taaattttgt gacttatggt tatctaataa tacgaatgtt atactttcca aaatttgaaa    4980
aaaacaatat gaatacttta ttattatctt tttccttcca tttctcttcc cgcgttttgt    5040
tgttcgaccg atcttgtagt acatgtgttc taatttgaac gtcgagaacc attaaagaag    5100
gaagaaagaa aagaaaaaaa aaaactttt tctcatttcg agatttccta accatttggt    5160
ggtgcaggtt taagtttcgc tcgctctcct aaaaccaaac gtccaaaccc gttctctaga    5220
ctagttctgc tgcgaaacac gacacacacc aagtcaccaa tattacttga atccacgtca    5280
aataaacaat ggtcattcaa tatggttaat gcaacactcg agtaacttta ttttcaaaga    5340
aatttgcaca aagtcatgtt atgatatggt gtataatatt tgtgtatata tccggccaaa    5400
aaacataaca agttttttat aaaaaaaaaa attaattata tatctaaaat atagaatagc    5460
tagtaataaa actagtgaga acaaatttta aaacaaatta agcaactatg ttatttgcca    5520
aattgacaat tttaaatatt atggcgtatt taaaaaaaat taggagccac ttgtgattta    5580
tttgtatcaa ctagtaaatt ttaaacataa aaatcattta taaatataaa taaatattat    5640
catatttatg tagaaagagt ctcatcagtc tgatagtcaa tcacttgtgc gcaaagaaat    5700
ttgacgaaag gggttacaaa aaaatggcca gcacagcatc atcatgtccc cgaccttata    5760
ttataagatt tgtatatttt atccataaat tgtatataac cgtcgac                  5807

<210> SEQ ID NO 29
<211> LENGTH: 26
<212> TYPE: DNA
<213> ORGANISM: Artificial Sequence
<220> FEATURE:
<223> OTHER INFORMATION: Microsatellite marker primer

<400> SEQUENCE: 29
gacatgattt aacataatgc caatta                                            26

<210> SEQ ID NO 30
<211> LENGTH: 25
<212> TYPE: DNA
<213> ORGANISM: Artificial Sequence
<220> FEATURE:
<223> OTHER INFORMATION: Microsatellite marker primer

<400> SEQUENCE: 30
```
cgaatagaaa ctcatttagg aacct                                    25

<210> SEQ ID NO 31
<211> LENGTH: 25
<212> TYPE: DNA
<213> ORGANISM: Artificial Sequence
<220> FEATURE:
<223> OTHER INFORMATION: SNP KNEF

<400> SEQUENCE: 31
cgtctctaag ttgtttaagg ggtta                                    25

<210> SEQ ID NO 32
<211> LENGTH: 26
<212> TYPE: DNA
<213> ORGANISM: Artificial Sequence
<220> FEATURE:
<223> OTHER INFORMATION: SNP KNER

<400> SEQUENCE: 32
tcacgcaagt taattatgta agatga                                   26

<210> SEQ ID NO 33
<211> LENGTH: 25
<212> TYPE: DNA
<213> ORGANISM: Artificial Sequence
<220> FEATURE:
<223> OTHER INFORMATION: SNP KKF

<400> SEQUENCE: 33
aaagagagta gaactcgctc aatgt                                    25

<210> SEQ ID NO 34
<211> LENGTH: 24
<212> TYPE: DNA
<213> ORGANISM: Artificial Sequence
<220> FEATURE:
<223> OTHER INFORMATION: SNP KKR

<400> SEQUENCE: 34
tatcaacagc tcgttactgg actg                                     24

<210> SEQ ID NO 35
<211> LENGTH: 26
<212> TYPE: DNA
<213> ORGANISM: Artificial Sequence
<220> FEATURE:
<223> OTHER INFORMATION: Primer bdy1

<400> SEQUENCE: 35
catgaggtgc gattcttctg taaagc                                   26

<210> SEQ ID NO 36
<211> LENGTH: 27
<212> TYPE: DNA
<213> ORGANISM: Artificial Sequence
<220> FEATURE:
<223> OTHER INFORMATION: Primer BDY3

<400> SEQUENCE: 36
ggaagaggag gagcttgtta tcatgac                                  27

<210> SEQ ID NO 37
<211> LENGTH: 28
<212> TYPE: DNA

```
<213> ORGANISM: Artificial Sequence
<220> FEATURE:
<223> OTHER INFORMATION: Primer ismr4

<400> SEQUENCE: 37
tccgcgaacg tttacagttt agatacag                                          28

<210> SEQ ID NO 38
<211> LENGTH: 21
<212> TYPE: DNA
<213> ORGANISM: Artificial Sequence
<220> FEATURE:
<223> OTHER INFORMATION: Primer OCSR

<400> SEQUENCE: 38
gaaccgaaac cggcggtaag g                                                 21

<210> SEQ ID NO 39
<211> LENGTH: 32
<212> TYPE: DNA
<213> ORGANISM: Artificial Sequence
<220> FEATURE:
<223> OTHER INFORMATION: Primer Bho5BAM

<400> SEQUENCE: 39
cgggatccga tctgatgcat cagtttcagg tg                                     32

<210> SEQ ID NO 40
<211> LENGTH: 32
<212> TYPE: DNA
<213> ORGANISM: Artificial Sequence
<220> FEATURE:
<223> OTHER INFORMATION: Primer Bho3BAM

<400> SEQUENCE: 40
cgggatccga gcaaaaatca tgagcgtaag at                                     32

<210> SEQ ID NO 41
<211> LENGTH: 25
<212> TYPE: DNA
<213> ORGANISM: Artificial Sequence
<220> FEATURE:
<223> OTHER INFORMATION: Primer 5RF3

<400> SEQUENCE: 41
agtacgatgc tcgcgaaacg gaatc                                             25

<210> SEQ ID NO 42
<211> LENGTH: 42
<212> TYPE: DNA
<213> ORGANISM: Artificial Sequence
<220> FEATURE:
<223> OTHER INFORMATION: Primer DyPB

<400> SEQUENCE: 42
aaaactgcag ggatccccaa cgttgaagag attcttggga gc                          42

<210> SEQ ID NO 43
<211> LENGTH: 27
<212> TYPE: DNA
<213> ORGANISM: Artificial Sequence
<220> FEATURE:
<223> OTHER INFORMATION: Primer DyCF

<400> SEQUENCE: 43
ccaaatcaca gagtcaccctc aaaacag                                          27
```

<210> SEQ ID NO 44
<211> LENGTH: 25
<212> TYPE: DNA
<213> ORGANISM: Artificial Sequence
<220> FEATURE:
<223> OTHER INFORMATION: Primer GRrev

<400> SEQUENCE: 44
gtaaaaccgt tgccagttct gactg                                              25

<210> SEQ ID NO 45
<211> LENGTH: 22
<212> TYPE: DNA
<213> ORGANISM: Artificial Sequence
<220> FEATURE:
<223> OTHER INFORMATION: Primer Ds5-2

<400> SEQUENCE: 45
cgttccgttt cgttttttta cc                                                 22

<210> SEQ ID NO 46
<211> LENGTH: 23
<212> TYPE: DNA
<213> ORGANISM: Artificial Sequence
<220> FEATURE:
<223> OTHER INFORMATION: Primer GLTF

<400> SEQUENCE: 46
aatgcacccg aaagtctatt tgc                                                23

<210> SEQ ID NO 47
<211> LENGTH: 39
<212> TYPE: DNA
<213> ORGANISM: Artificial Sequence
<220> FEATURE:
<223> OTHER INFORMATION: Primer PDYBAM

<400> SEQUENCE: 47
acggatccta gaacaagaga aaaactaaga gagatattt                               39

<210> SEQ ID NO 48
<211> LENGTH: 24
<212> TYPE: DNA
<213> ORGANISM: Artificial Sequence
<220> FEATURE:
<223> OTHER INFORMATION: Primer PG2R4

<400> SEQUENCE: 48
tctggggctc gtcgactttt tgtt                                               24

<210> SEQ ID NO 49
<211> LENGTH: 21
<212> TYPE: DNA
<213> ORGANISM: Artificial Sequence
<220> FEATURE:
<223> OTHER INFORMATION: Primer KanF

<400> SEQUENCE: 49
gccaacgcta tgtcctgata g                                                  21

<210> SEQ ID NO 50
<211> LENGTH: 22
<212> TYPE: DNA
<213> ORGANISM: Artificial Sequence
<220> FEATURE:

<223> OTHER INFORMATION: Primer KanR

<400> SEQUENCE: 50
gattgaacaa gatggattgc ac        22

<210> SEQ ID NO 51
<211> LENGTH: 803
<212> TYPE: PRT
<213> ORGANISM: Oryza

<400> SEQUENCE: 51

```
Met Asp Ala Glu Met Ala Ala Pro Ala Leu Ala Ala His Leu Leu
1               5                   10                  15

Asp Ser Pro Met Arg Pro Gln Val Ser Arg Tyr Tyr Ser Lys Lys Arg
                20                  25                  30

Gly Ser Ser His Ser Arg Asn Gly Lys Asp Asp Ala Asn His Asp Glu
            35                  40                  45

Ser Lys Asn Gln Ser Pro Gly Leu Pro Leu Ser Arg Gln Ser Leu Ser
50                  55                  60

Ser Ser Ala Thr His Thr Tyr His Thr Gly Gly Phe Tyr Glu Ile Asp
65                  70                  75                  80

His Glu Lys Leu Pro Pro Lys Ser Pro Ile His Leu Lys Ser Ile Arg
                85                  90                  95

Val Val Lys Val Ser Gly Tyr Thr Ser Leu Asp Val Thr Val Ser Phe
                100                 105                 110

Pro Ser Leu Leu Ala Leu Arg Ser Phe Phe Ser Ser Pro Arg Ser
                115                 120                 125

Cys Thr Gly Pro Glu Leu Asp Glu Arg Phe Val Met Ser Ser Asn His
130                 135                 140

Ala Ala Arg Ile Leu Arg Arg Arg Val Ala Glu Glu Leu Ala Gly
145                 150                 155                 160

Asp Val Met His Gln Asp Ser Phe Trp Leu Val Lys Pro Cys Leu Tyr
                165                 170                 175

Asp Phe Ser Ala Ser Pro His Asp Val Leu Thr Pro Ser Pro Pro
                180                 185                 190

Pro Ala Thr Ala Gln Ala Lys Ala Pro Ala Ala Ser Ser Cys Leu Leu
            195                 200                 205

Asp Thr Leu Lys Cys Asp Gly Ala Gly Trp Gly Val Arg Arg Arg Val
210                 215                 220

Arg Tyr Ile Gly Arg His His Asp Ala Ser Lys Glu Ala Ser Ala Ala
225                 230                 235                 240

Ser Leu Asp Gly Tyr Asn Thr Glu Val Ser Val Gln Glu Glu Gln Gln
                245                 250                 255

Gln Arg Leu Arg Leu Arg Leu Arg Gln Arg Arg Glu Gln Glu
            260                 265                 270

Asp Asn Lys Ser Thr Ser Asn Gly Lys Arg Lys Arg Glu Glu Ala Glu
            275                 280                 285

Ser Ser Met Asp Lys Ser Arg Ala Arg Lys Lys Ala Lys Thr
290                 295                 300

Tyr Lys Ser Pro Lys Lys Val Glu Lys Arg Val Val Glu Ala Lys
305                 310                 315                 320

Asp Gly Asp Pro Arg Arg Gly Lys Asp Arg Trp Ser Ala Glu Arg Tyr
                325                 330                 335

Ala Ala Ala Glu Arg Ser Leu Leu Asp Ile Met Arg Ser His Gly Ala
                340                 345                 350
```

```
Cys Phe Gly Ala Pro Val Met Arg Gln Ala Leu Arg Glu Ala Arg
            355                 360                 365
Lys His Ile Gly Asp Thr Gly Leu Leu Asp His Leu Leu Lys His Met
    370                 375                 380
Ala Gly Arg Val Pro Glu Gly Ser Ala Asp Arg Phe Arg Arg Arg His
385                 390                 395                 400
Asn Ala Asp Gly Ala Met Glu Tyr Trp Leu Glu Pro Ala Glu Leu Ala
                405                 410                 415
Glu Val Arg Arg Leu Ala Gly Val Ser Asp Pro Tyr Trp Val Pro Pro
            420                 425                 430
Pro Gly Trp Lys Pro Gly Asp Asp Val Ser Ala Val Ala Gly Asp Leu
            435                 440                 445
Leu Val Lys Lys Val Glu Glu Leu Ala Glu Glu Val Asp Gly Val
    450                 455                 460
Lys Arg His Ile Glu Gln Leu Ser Ser Asn Leu Val Gln Leu Glu Lys
465                 470                 475                 480
Glu Thr Lys Ser Glu Ala Glu Arg Ser Tyr Ser Ser Arg Lys Glu Lys
                485                 490                 495
Tyr Gln Lys Leu Met Lys Ala Asn Glu Lys Leu Glu Lys Gln Val Leu
            500                 505                 510
Ser Met Lys Asp Met Tyr Glu His Leu Val Gln Lys Lys Gly Lys Leu
            515                 520                 525
Lys Lys Glu Val Leu Ser Leu Lys Asp Lys Tyr Lys Leu Val Leu Glu
    530                 535                 540
Lys Asn Asp Lys Leu Glu Gln Met Ala Ser Leu Ser Ser Ser Phe
545                 550                 555                 560
Leu Ser Leu Lys Glu Gln Leu Leu Pro Arg Asn Gly Asp Asn Leu
            565                 570                 575
Asn Met Glu Arg Glu Arg Val Glu Val Thr Leu Gly Lys Gln Glu Gly
                580                 585                 590
Leu Val Pro Gly Glu Pro Leu Tyr Val Asp Gly Gly Asp Arg Ile Ser
            595                 600                 605
Gln Gln Ala Asp Ala Thr Val Val Gln Val Gly Glu Lys Arg Thr Ala
    610                 615                 620
Arg Lys Ser Ser Phe Arg Ile Cys Lys Pro Gln Gly Thr Phe Met Trp
625                 630                 635                 640
Pro His Met Ala Ser Gly Thr Ser Met Ala Ile Ser Gly Gly Gly Ser
            645                 650                 655
Ser Ser Cys Pro Val Ala Ser Gly Pro Glu Gln Leu Pro Arg Ser Ser
            660                 665                 670
Ser Cys Pro Ser Ile Gly Pro Gly Gly Leu Pro Pro Ser Ser Arg Ala
            675                 680                 685
Pro Ala Glu Val Val Val Ala Ser Pro Leu Asp Glu His Val Ala Phe
    690                 695                 700
Arg Gly Gly Phe Asn Thr Pro Pro Ser Ala Ser Ser Thr Asn Ala Ala
705                 710                 715                 720
Ala Ala Ala Lys Leu Pro Pro Leu Pro Ser Pro Thr Ser Pro Leu Gln
                725                 730                 735
Thr Arg Ala Leu Phe Ala Ala Gly Phe Thr Val Pro Ala Leu His Asn
            740                 745                 750
Phe Ser Gly Leu Thr Leu Arg His Val Asp Ser Ser Pro Ser Ser
            755                 760                 765
```

```
Ala Pro Cys Gly Ala Arg Glu Lys Met Val Thr Leu Phe Asp Gly Asp
    770                 775                 780

Cys Arg Gly Ile Ser Val Val Gly Thr Glu Leu Ala Leu Ala Thr Pro
785                 790                 795                 800

Ser Tyr Cys

<210> SEQ ID NO 52
<211> LENGTH: 5335
<212> TYPE: DNA
<213> ORGANISM: Z. mays

<400> SEQUENCE: 52
gtagagatgg caatgggtac ccgaaacccg aatacccgac gggttttccc cgatatgaag      60
gcgggtacgg gatgatttct ctacccgcgg gtatgttaat gggtaaaaaa ctctacccgt     120
tgggtagacg ggtacggata tgggttggta cgtctatccg tgggtaaaat atacccgcat     180
caataacact ataaacatct aatagagtcc aacttagcta gaataaaatc cttctctagt     240
tatcatttat ctagatacca agttatgtaa tcatatgatt tgttatatgt gaaattgaag     300 ttgttttat atgtttattt aatattttga gtgattggta tattggaatt taattctttc      360
cgagcgggta cgggttaccc gatgggtaaa atacccgcg cggatacggg tatgggtaag     420
attttatacc cgcgagcata tatgggtaac ctgacgggta gattttttt tgatgggtac     480 gggtatagaa tggtactacc cgacgggtat gtacccgttg ccatccctag acacgagcat    540
gctacggaag gagcggtggg aggtcttagg ctggtgccaa tgggggctag aagggaggcg    600
agaagggccc tctaccgccc cgcgcgaggc gataggcagg cgagagggag agagagggcg    660
acagcactca cgcccggcga gagcgggcga tatcgccccg ctctcgcccg cgttggcgcg    720
cgcgtctggg cgagagggag gcgagaggga ggcgagaggg gggcgacgca ctgacggggc    780
gagagtgagg cgggcgagag tgcggtggcg cgacgtgatt ggtccacgtg tgccacgtgg    840
actagccgtt ttttaccgtt tggagtccaa aaaattcgaa aaaattgcaa aaatcacaa      900 atttcattcc caatccatct ataaatatcc ctacctgttg gaggtcataa ttagatttat     960
gtaatttctc attaattgtt atgtaatttt ttaattgtca tgtactttc ttttaattat     1020 tatacacttt gtaattttaa attcaataaa aaatattatg ttgtgtgatt tgtaagcgtt    1080
gaaacaaatc tgtgtgaatt atttaatcct gaaatagaaa agctgatgtg gctatgggct    1140
gaggctatag cctgctacag cctgtgcact ggagcagcag aggcgagagt ggaggcgaga    1200
gctgacgtgg caggggcgag agagaggctg tgcactggac tcagcctaac tgcaactgga    1260
cttgcactgc tggagcgaga aggaaggcga cgcaccaacc aaccggtaca gcgctgcgag    1320
aacaagtgaa caaccaaacg caccaggcgg gggtctccgt ctctatagtt gggatttggg    1380
aacagttccg tcactgtgtg ttactgttac cgcagtgaaa gactgatggg ctcttgggtc    1440
ggtggatcct gtacgaaaga ctgatgggct cttgactgcc aagtcagcat atgttgcaca    1500
attttgagga tcttttttgt cctttttaatg catcaaccat ttggagccct catgcggagg    1560
gaaagcagga attcttcact ggctgctcat tcaaaaacaa gattctaaca gctgacaacc    1620
ttacctggag gcattggccc tgcaacccgg tctgcactct atgcaatcag gattgggaag    1680
acagctatac atctatgctt caaatgtcct tttgcctcac atgtttggga ttctttaaga    1740
atctggtcca ataatctcat tcaacatcct agcactagca gcgacgtcca aagcattgtt    1800
gactggtggc tgcgatcttc tatgcataga accaaaagca tccacagaac ggtggcaggg    1860
attaaaatct gagtgaggtc ccagcttaga tctcaatcta tcttgctgtt gtgcggctgc    1920
```

```
gccttgtaaa tagctcctgt aaccttccct ctgtacgact caatctcctt tcattcttat    1980
atgaattagc agtgctcctg ctacttttt caaaaaaaa tcaccagcat caagaacata    2040
cagattgtaa ggggaaatta aatatcacca atatatatat gcccgaaaaa attggtcaca    2100
cttaatatgt agtgcagcag gcatacaaga atgacccggt atattctata acatgactct    2160
atatgcccta tggtgccagc aaaatcgaca catctcaact ccaaatgtgt catgcaccat    2220
ggacagggga gaatgggaga tgaccatacc caactgactt actgaagaga ccaatccaat    2280
gcaacgactt tagcttcaac ctgagaatta actagaaact gacgaacctg agatggctac    2340
ggaagtacga ttatgccaca aagactgctc aagtgagttc atattcsctt tttcttatct    2400
tttttctctc tctctttttt tctctctctc tctgtattta cgctacgtgt tgctcctttg    2460
ttacaaagac agaaaattgg agcaccctga ggccaaccat ccaaagcttt gcttgcagat    2520
ggggaagagg cgatgatcct gaagtggaaa ggtaggagta ggtcagcagt aggatggagt    2580
agccagggcc agctcggttc ccaccgcgct gatcccgccg gcgtctgcat cgaacaggac    2640
cctcttcccc tctagcaggc cggaaccgca ggccccggac gatgacgacg aggtgtcctg    2700
cacagcccac gatcagtcga acatgaatca gcttgcacgt ttcttgactg gttatggtta    2760
gctagtagcc tagtactaat gcttgccgac agcaatggaa cagcaggcca gagtccagac    2820
tatagaacca gaggataaag agaaagcaag caaagtggac ttaccacatc gcgtcgagtc    2880
aggccggaga atgcatcag cttttgggga ctaaacccag aagcagcagc agtaacagtg    2940
tcaaacagct tctgcggctg caggggcgac ctcgggctgg gcaggacag ctgcagcttg    3000 gcagcgtcgt tggtggacga cgccgagggc ggcgtagaga agtgggcgcc aaacatcacg    3060
tgctcgtcca ggccggacgc cgccgccacc acctcaactg ggcctcgcga cgaccgcggg    3120
aggcccggca tactggggaa actggtgctg cgagggatcc ccgggcctgg cgtggcggcg    3180
gccgggcagg tgctgctggc gccctgccg atggtcatgc cagacgccat gctcggcaac    3240
aggaacttgc cctgtggctt acagacgcgg aagctgctct tcctttccgc cctgtcttgg    3300
ccgccttgga tgacggtgcc ggtcatctgc tcaccggaag caacgaacag tgctgtgcgg    3360
ggaacagctt cacttggagc cagttccagc ttcagagcca ctaccagctg atcctgcacc    3420
actcaattct gtttacttca actcatggaa gatgtcagat gtacatttgc ataggctgag    3480
aaaaatcaat aaaaagagtg cattgccata caaggagcta ccttgaaaga aggaaggag    3540 ctggagaggt aggtaacctg ctcctctaac ttatcattct tgtcagctat atgctcgtac    3600
ttttcctgaa attaaacagt ggttcactaa ctgtatttgg agttacacgg atctagcagg    3660
caaaatgtgc ataggaatag atgctacaga taaaaagat cattgtgaat gtcatagctg    3720
tctcctgtct gcatgaatgt accttgaagg atgacacctc cttcttcagc tcaccattca    3780
tctgaaccac attctcacac atgtcctgaa ataaaaggc aatatcattt ctgaaaattc    3840
agcaagcaga cttagcaaag acatagcttt ttattttgca aggatatcga agtcatagct    3900
tccctgtaaa tttaataagt gaagacaaat caataacggg catggtttct cagttctcat    3960
tttgtttgaa attactgaag ccaaattagt aacaggcata gttttctcggt tgtcatttag    4020 tttgaaacta actaccacat ttttcctagc agacaatgtt gctgcatcca tgcgcttacc    4080
ttcaaacaga gcacctgctt ctcaagcttt tcattagccc tcacagcacg ctggtacttc    4140
tcctgacaaa caaattgata agctttcatt agtgcatcca aaatgggcat gccaaatagt    4200
ttctatcagt tagtatagtc aatgtgagaa gtaaaacaga gaaactgtag ttcatgctag    4260
```

-continued

| | |
|---|---|
| tcagatcatg cacatcagta catcctggat tcagaatttc agagactgga caaggaacta | 4320 |
| gctatgttct tacagacagc aagcattatg aaacatcaga gaaactgaac cgggagtcca | 4380 |
| ggactggcat tctattctag cacttcaaaa acctcccgt caacatacga atgatgtac | 4440 |
| atgacttgca caacccaacc caacatacag aaacatggaa aatgctctaa tgcctatgat | 4500 |
| tttccaaaat aaagagaggt gcaaatacat atccaagtat acagaaatat ccacatcagt | 4560 |
| gccactacca tatcttgctc agtttaatca gaagcagcag ccttcaaaag ttaagggaac | 4620 |
| aacgaattgt aacagggtaa aggagctgat cttttgcata ctttcaatga actgtagtct | 4680 |
| ctctctgcac cgaagtcccc atcatccttg cacataact gctccatttg ccttcacaca | 4740 |
| ccaccacaag aataacttgg cataaaactc agaagaaacc ccttgtctat gtaagaactt | 4800 |
| agcagggtcg tagcactgat ggcttgaatt gccataaaac tatatattat agagtgcaga | 4860 |
| cagacaaaag gagtagaaaa agatatacct ttttacgcca ttgacctcct cggtgagctc | 4920 |
| ctcaacctgc ctcttgacta gaatgtcgcc ggcgacgagg gacacatcat cacctggttt | 4980 |
| ccatcccggc ggtggcaccc agtatggatc agatacaccg gcctgtttcc gtacctcagc | 5040 |
| aagctcggct ggctcaagcc agtactccat ggcaccatcc gcattgtgcc ggcgacgaaa | 5100 |
| ccggtgaacg ctgccttccg gcacccggcc agccatgtgc ttgagcaggt ggtcaaggag | 5160 |
| gccggtgtcg ccgatgtgct tgcgggcttc ctcccgcagc acctgccgca tcaccggtgc | 5220 |
| gccgaaccgt gcgtctcggg agcgcatgat gttgagcagg ctcttctctg ctgcggcgta | 5280 |
| gcgctcggct gaccaccggt ccttgccgtg cccgagggtc accgtccttg gattc | 5335 |

<210> SEQ ID NO 53
<211> LENGTH: 4862
<212> TYPE: DNA
<213> ORGANISM: Z. mays

<400> SEQUENCE: 53

| | |
|---|---|
| gcgcgcggcg tggttgctgc tcatgacgaa gcgctcgtct agttccggtc cggtgccggg | 60 |
| tgccgggtag gaggagaaga agctgcgcag cgcctgaagg gacgggaatt tcactgtgat | 120 |
| gtccaggttc gtgcactcgc tcacctaggt acaggccaga acttgctcaa acatatgcta | 180 |
| aacaaacaga ttaagaaatt gagagcagaa attgaatccc agaaagaaaa atctcacctt | 240 |
| aaccacccgt atggatttca gatggattgg ggatttaggg ggcaatttat cgtggtcgat | 300 |
| ctcgtagaaa gctcctgatg gaaatcgaac caatttacac aagtgtcaga tactcaggtg | 360 |
| ggcgtggcat gaataatagt agtgttaccg tgttgcatcg tatatgcccg tgctcaccag | 420 |
| cgtggtatgt ggggatggcg tcgaaggtca ggctctgtct gctcaggggc gacctgggtt | 480 |
| gaatcgtgga gtcgtggttg acatcatcct taccatttct gctatgacta ctgctcgtct | 540 |
| tcttcttgaa gtagtacttc ttcacctgtg gcttcttgtg atttgcaatg gtcacacaaa | 600 |
| caacgggtga gaccgagacg tgtatgattc ttggaaacaa aattatacac tgaaatggtc | 660 |
| aagttttttt ggagattgag agcgcgtgca tgtgcatggg agaactagtc tcgggaaaga | 720 |
| cagacaacag tcaacataat gtaccactgg accaacagaa atgaaaagag acatgcaaag | 780 |
| ggaacataca ggtactttt aacatgaaga ctgccggttc gttaccataa ataatcatca | 840 |
| cctatcctaa aatgggttaa caaaaataac gaacggctta acaattaata atatttatt | 900 |
| aagtcattta aggtgaatga tcattatctt gggtaacaaa tagtgttgtc tatatataca | 960 |
| cacaaattaa aattgaggtg tatatatata tatatagccc aaagacaaag tcaacttgaa | 1020 |
| atgttcaacg ataatggcaa gtggactaca gtatacaaag ggacaaattg tatagctatc | 1080 |

```
taggaccttt ttaaaaaaat aaataaaaag caagcactat aaccatgcta attatagtgc      1140
gtgggttgat tcaaacaac ccaacatcac gtcttcgtga aaaaaaaga ataataacac        1200 tgatccagct agtggcacga atgtctagag ttcaattgca caagaatcc caaataaaca       1260 aaagagagag agaaaaagat gcattatcca ttgtctgtag aaattagcac ataaaactca     1320
acatgcctag ggtgtttaat tagtttaaca acaatgaacc tgtttggaaa caccatagtt    1380 tttttaaaa atgttttcta tattcagttt gtagaatgaa actggtttgt aaaaaaaact     1440
aagtgtgcat gtttggaagc cagttttttt aaaacaatt tctaccattt ctgatacaca    1500
gagtaattga ttatattatc cccttttat ttgttgccat atataaataa tataggttaa    1560
actcatattt ttaattcaaa attttcaaat aattaaccat tcaaatccga tagagcagac   1620
atcgagatga tcgcatgcat aggtctggag cggtggcaat caccataatt tccacaaaac   1680
caactaagaa cagtacgaaa tttgcgaggc aaaaaaccgg ttttaaatag aaaaggctag   1740
cttcctggtt tattagaagc tgggaatcca gttttttgaa actggagcaa aaaaattggc   1800
atgtttgaaa gcaccctagt ttctataatc tattttttca aagctgggtg tgcttccaaa   1860
cagaccctat taattgttac tccctccgtt tcgttttagt tgtcgctgga tagtacaaaa   1920
ttgaactatc cagcgacaac taaaaagaaa cggatggagt attcttttaa cagccatgtt   1980
ccctcatcag ctaccaatgc acgtataatt aactgaacaa actagtagta cgttgtactg   2040
tcctctagta gagtccatat ataggcaaca ctatagaaag tacactattc caaatcaagc   2100
aacggttcag caattttcaa aatgccgcac ttaatgtgct cagcagattt taacaaggct   2160
cacgttggag aaatgaccat gccttgctgt tttcacacta actattttg tcaacctata    2220 tatagcattc atgcacttgt attaaaataa gcaagatcag tctaacaagt tgaacccatc   2280
agcggctctt gagtccagat aactaccacg gacaataaac tacttgcgag agcatcaaat   2340
caaaggatat atcgactaca gtacatctca gtaactatac atctcaaatt aaacatcgat   2400
ccagcgaaat atcgaattaa tcacccaaaa agcaactaat aaagcggcgc acaatatcct   2460
atatcattgt aactgaccgc gcgcagccgc agcagtaggt cagtggaaag agaaaccaac   2520
agatcaccac cataccccaga tcacagaaag caaaaggtaa taatcgaact ggcaaaagtc   2580
gcagctagcg tctacgacgt gtagcaagac cggactggcc cgacacgtac gtaccggcga   2640
tgcctgcagc tgcagatgag ccgcgagcgc aggacccgcc tgcaccgtct ctacgtccat   2700
ctgcatgcgg gtcctcagag ttttttttgg gtctcctgca aaagcaaacg ggcaaacaaa   2760
cccaccgatc aagacaagta tatatatata gttcaaaaag agttaagcaa gaaggacaga   2820
gaccctccga tgatcgaaat gataacaaat tttcgaaacc catccaaatt gacccgcata   2880
tagatgaact aataataatg cgcactggca ttttccgacc aaactggcga gatttataaa   2940
ttgtaagttc gaagaaaaaa cattcaaaac tctagttccc aaaccaaagc accaaaaggc   3000
aggcaacaaa agtcaccaaa ctgagtctga ggttgaacgc ttcaagggga aaagagagcg   3060
cgcctcatct cgtctcgtct agcagcagcg cgttatgtgg caaaagtcgc ttgtacgaag   3120
aacctgcaag ctgcttttctg ctgctagcgg caagccgcaa ccgcacggat cgatcgaagc   3180
aaaagcaagc gaggcccgag gaaacagcga caaggcagca gagatcggaa aggaaaaacg   3240
agctgctttt gcgatcgaag tatagaacca gcgagctttt tggcactgcc gcggaatcgc   3300
gcagcgcggt aggaagtggt ccgcgtcgcg ggcttcctcg tgcccggagc ctctctagca   3360
aaaaacccaa cagcatcaga cacctatagc agcagtgcag tacacccgta caacagttcg   3420
```

```
ttttgatcaa gcgggtttta ggtcacgccc ttttcgcatc aaattgagag aagggaacga  3480
accagatgga gaaaaatggc ccggatcaga acgaagaaga atgagagacc ggatgaacac  3540
acactgctac cagcagggcg cggttagaaa tagatcgcag aagaataccc acgacgcata  3600
catatgccag agcaattagg ccactactca cctgtgtggt atttacttgc tgctgctgct  3660
gcttctggga tcggggtggg atcgaatcaa aaagaaaagt agaggcaggc cgaaatgtgg  3720
cgagaaaatt gggtcgctag acaattctag tggagtgctt attctctgat cgatgtacct  3780
ggggacgatc gatcccgaaa ggcgggggga gctttgggga ggcgatcgag ctagttcatg  3840
gtggggagta gtggagtgga ggcaggcgcc gtgggtcggg aggtggggcg ctagggtttt  3900
tgttgttccg tgatcgatcg gcgtcggggg gctgggctc cgcctcttct cccccggctg  3960
cctcacctcg ttgatcaccg tgtccgcctc gtcgtgcggg gagccgggga ctagatagtg  4020
ccgtggagga gaatcctttt tctagagaga ggagtggggt ggcagggtgc agcgcgtgtg  4080
tgatgctgat gccgttgtag agagagaaaa atctaggaca gccaggctcg tcgcagaggg  4140
cagcaagcag caacctcctc acggaacggc ccgcacctgg tctgccgggg gatcgagcct  4200
atgacacgtg ggcccgctct gcccgcggac cagacgtgtc tgcaggcagc ccggcacggc  4260
agacgggtgg gtgttgtgcg ggcgacgacg atatatgcgg tgcccaagta gcggtggcga  4320
agcgcgcgag accttgtgga ccccatctgt cgggcgagag cgcgcggcgc accattacaa  4380
ggacgacgct tgcgaaacga tggcgcgggc gcgccggcac acgcgcatgg gggagtttgg  4440
gttgacattg tggcacttgg gatcggggcg gggtccgccg ggggctgtga tgatgatgag  4500
gcggaggcgg gcggagcaaa gcagagaaga aaccaattgc ttgcagttgc aggcacaggc  4560
cgtactaata aataaatgtg ggtacgctgg caacgctgcc actgttagct actagtagta  4620
gctacagatg cacggcccgg acgcaggcgt gcatgggatg atctctccac acgcgctctt  4680
ggtgcgtgcg tgtgcgagga ttctgtctac ggtttgcttg catgcacgct tgcggaggca  4740
gaggtagtca cgtcgtcaag cgtgaagccg tgaatcgatc cacgcacgca gcaatgcact  4800
ccccgtttct cctttacgg atctaataat aattataata atacattata aatattattg  4860
tt                                                                4862
```

<210> SEQ ID NO 54
<211> LENGTH: 469
<212> TYPE: PRT
<213> ORGANISM: Z. maize

<400> SEQUENCE: 54

```
Glu Ser Lys Asp Gly Asp Pro Arg His Gly Lys Asp Arg Trp Ser Ala
1               5                   10                  15

Glu Arg Tyr Ala Ala Ala Glu Lys Ser Leu Leu Asn Ile Met Arg Ser
            20                  25                  30

Arg Asp Ala Arg Phe Gly Ala Pro Val Met Arg Gln Val Leu Arg Glu
        35                  40                  45

Glu Ala Arg Lys His Ile Gly Asp Thr Gly Leu Leu Asp His Leu Leu
    50                  55                  60

Lys His Met Ala Gly Arg Val Pro Glu Gly Ser Val His Arg Phe Arg
65                  70                  75                  80

Arg Arg His Asn Ala Asp Gly Ala Met Glu Tyr Trp Leu Glu Pro Ala
                85                  90                  95

Glu Leu Ala Glu Val Arg Lys Gln Ala Gly Val Ser Asp Pro Tyr Trp
            100                 105                 110
```

```
Val Pro Pro Gly Trp Lys Pro Gly Asp Asp Val Ser Leu Val Ala
            115                 120                 125
Gly Asp Ile Leu Val Lys Arg Gln Val Glu Glu Leu Thr Glu Val
130                 135                 140
Asn Gly Val Lys Arg Tyr Ile Glu Gln Leu Leu Cys Lys Asp Asp Gly
145                 150                 155                 160
Asp Phe Gly Ala Glu Arg Asp Tyr Ser Ser Leu Lys Glu Lys Tyr Gln
                165                 170                 175
Arg Ala Val Arg Ala Asn Glu Lys Leu Glu Lys Gln Val Leu Cys Leu
            180                 185                 190
Lys Asp Met Cys Glu Asn Val Val Gln Met Asn Gly Glu Leu Lys Lys
        195                 200                 205
Glu Val Ser Ser Phe Lys Glu Lys Tyr Glu His Ile Ala Asp Lys Asn
    210                 215                 220
Asp Lys Leu Glu Glu Gln Val Thr Tyr Leu Ser Ser Phe Leu Ser
225                 230                 235                 240
Phe Lys Asp Gln Leu Val Val Ala Leu Lys Leu Glu Leu Ala Pro Ser
                245                 250                 255
Glu Ala Val Pro Arg Thr Ala Leu Phe Val Ala Ser Gly Gln Met
            260                 265                 270
Thr Gly Thr Val Ile Gln Gly Gly Gln Asp Arg Ala Glu Arg Lys Ser
        275                 280                 285
Ser Phe Arg Val Cys Lys Pro Gln Gly Lys Phe Leu Leu Pro Ser Met
    290                 295                 300
Ala Ser Gly Met Thr Ile Gly Arg Gly Ala Ser Ser Thr Cys Pro Ala
305                 310                 315                 320
Ala Ala Thr Pro Gly Pro Gly Ile Pro Arg Ser Thr Ser Phe Pro Ser
                325                 330                 335
Met Pro Gly Leu Pro Arg Ser Ser Arg Gly Pro Val Glu Val Val Ala
            340                 345                 350
Ala Ala Ser Gly Leu Asp Glu His Val Met Phe Gly Ala His Phe Ser
        355                 360                 365
Thr Pro Pro Ser Ala Ser Ser Thr Asn Asp Ala Ala Lys Leu Gln Leu
    370                 375                 380
Ser Leu Pro Ser Pro Arg Ser Pro Leu Gln Pro Gln Lys Leu Phe Asp
385                 390                 395                 400
Thr Val Thr Ala Ala Ala Ser Gly Phe Ser Pro Gln Lys Leu Met His
                405                 410                 415
Phe Ser Gly Leu Thr Arg Arg Asp Val Asp Thr Ser Ser Ser Ser
            420                 425                 430
Gly Ala Cys Gly Ser Gly Leu Leu Glu Gly Lys Arg Val Leu Phe Asp
        435                 440                 445
Ala Asp Ala Gly Gly Ile Ser Ala Val Gly Thr Glu Leu Ala Leu Ala
    450                 455                 460
Thr Pro Ser Tyr Cys
465

<210> SEQ ID NO 55
<211> LENGTH: 132
<212> TYPE: PRT
<213> ORGANISM: Z. mays

<400> SEQUENCE: 55

Met Ser Leu Phe Ile Ser Lys Pro Gln Val Lys Lys Tyr Tyr Phe Lys
1               5                   10                  15
```

```
Lys Lys Thr Ser Ser His Ser Arg Asn Gly Lys Asp Asp Val Asn
            20              25              30

His Asp Ser Thr Ile Gln Pro Arg Ser Pro Leu Ser Arg Gln Ser Leu
        35              40              45

Thr Phe Asp Ala Ile Pro Thr Tyr His Ala Gly Ala Phe Tyr Glu Ile
    50              55              60

Asp His Asp Lys Leu Pro Pro Lys Ser Pro Ile His Leu Lys Ser Ile
65              70              75              80

Arg Val Val Lys Val Ser Glu Cys Thr Asn Leu Asp Ile Thr Val Lys
            85              90              95

Phe Pro Ser Leu Gln Ala Leu Arg Ser Phe Phe Ser Ser Tyr Pro Ala
            100             105             110

Pro Gly Thr Gly Pro Glu Leu Asp Glu Arg Phe Val Met Ser Ser Asn
        115             120             125

His Ala Ala Arg
        130
```